(12) United States Patent
Ral et al.

(10) Patent No.: US 10,100,324 B2
(45) Date of Patent: Oct. 16, 2018

(54) PLANTS WITH MODIFIED STARCH METABOLISM

(75) Inventors: Jean-Philippe Francois Michel Ral, Giralang (AU); Zhongyi Li, Kaleen (AU); Matthew Kennedy Morell, Aranda (AU)

(73) Assignees: COMMONWEALTH SCIENTIFIC AND INDUSTRIAL RESEARCH ORGANISATION, Campbell (AU); GRAINS RESEARCH AND DEVELOPMENT CORPORATION, Barton (AU)

( * ) Notice: Subject to any disclaimer, the term of this patent is extended or adjusted under 35 U.S.C. 154(b) by 909 days.

(21) Appl. No.: 12/745,237

(22) PCT Filed: Nov. 27, 2008

(86) PCT No.: PCT/AU2008/001759
§ 371 (c)(1),
(2), (4) Date: May 27, 2010

(87) PCT Pub. No.: WO2009/067751
PCT Pub. Date: Jun. 4, 2009

(65) Prior Publication Data
US 2011/0045127 A1    Feb. 24, 2011

(30) Foreign Application Priority Data

Nov. 27, 2007 (AU) ................. 2007906467

(51) Int. Cl.
| | | |
|---|---|---|
| *C12N 15/82* | (2006.01) | |
| *C12N 9/12* | (2006.01) | |
| *A01H 5/10* | (2018.01) | |
| *C07K 14/415* | (2006.01) | |

(52) U.S. Cl.
CPC ........ *C12N 15/8245* (2013.01); *C07K 14/415* (2013.01); *C12N 9/1294* (2013.01); *C12N 15/8234* (2013.01); *C12N 15/8261* (2013.01); *C12Y 207/09004* (2013.01)

(58) Field of Classification Search
CPC .............. C12N 9/1294; C12N 15/8261; C12N 15/8245
See application file for complete search history.

(56) References Cited

U.S. PATENT DOCUMENTS

| | | |
|---|---|---|
| 6,207,880 B1 | 3/2001 | Kossmann et al. |
| 6,353,154 B1 | 3/2002 | Kossmann et al. |
| 6,462,256 B1 | 10/2002 | Abel et al. |
| 6,504,085 B1 | 1/2003 | Howard |
| 6,521,816 B1 * | 2/2003 | Frohberg ............ C07K 14/415 435/101 |
| 6,620,987 B1 | 9/2003 | Allen et al. |
| 6,734,340 B2 | 5/2004 | Schewe et al. |
| 6,951,969 B1 | 10/2005 | Loerz et al. |
| 7,001,771 B1 | 2/2006 | Morell et al. |
| 7,122,727 B2 * | 10/2006 | Abel et al. ................. 800/320.3 |
| 7,176,190 B2 | 2/2007 | Kossmann et al. |
| 7,521,593 B2 | 4/2009 | Regina et al. |
| 7,569,744 B2 | 8/2009 | Kossmann et al. |
| 7,667,114 B2 | 2/2010 | Morell et al. |
| 7,700,139 B2 | 4/2010 | Bird et al. |
| 7,700,826 B2 | 4/2010 | Morell et al. |
| 7,790,955 B2 | 9/2010 | Li et al. |

(Continued)

FOREIGN PATENT DOCUMENTS

| | | |
|---|---|---|
| WO | WO1990/012876 | 11/1990 |
| WO | WO1998/027212 | 6/1998 |

(Continued)

OTHER PUBLICATIONS

Ritte et al (PNAS 2002, (99)10 p. 7166-7171).*
Hood (Molecular Breeding 3: 291-306, 1997).*
Stanley et al (Biologia, Bratislava, 60/Suppl. 16: 65-71, 2005).*
Rajagopalan et al (Genes & Development 20: 3407-3425)).*
Kötting et al (Plant Physiology, 2005 vol. 137 p. 242-252).*
Stanley (Biologia, Bratislava, 60/Suppl. 16: 65-71, 2005).*
International Preliminary Report on Patentability, dated Jun. 2, 2010 in connection with PCT International Application No. PCT/AU2008/001759, of which the subject application is a §371(c) national stage entry.

(Continued)

*Primary Examiner* — Lee A Visone
(74) *Attorney, Agent, or Firm* — John P. White; Cooper & Dunham LLP

(57) ABSTRACT

The specification provides methods of obtaining a genetically modified plant which has increased production potential compared to a control plant, the method comprising the steps of i) obtaining a plurality of plants at least one of which comprises in its genome a heterologous polynucleotide, ii) identifying from the plurality of plants a plant which has increased production potential relative to the control plant and comprises the heterologous polynucleotide, and iii) selecting the genetically modified plant, wherein the polynucleotide comprises a transcriptional control sequence operably linked to a nucleic acid sequence which encodes an agent that modifies endogenous starch phosphorylation and/or starch degradation in the plant. In some embodiments, the plant has increased endogenous glycosylase or increased digestibility compared to a control plant. In some specific embodiments, the endogenous starch phosphorylation and/or starch degradation is modified by modifying expression or activity of one or more enzymes selected from the group consisting of α-amylase (EC 3.2.1.1), β-amylase (EC 3.2.1.2), glucoamylase (EC 3.2.1.3), starch phosphorylase (EC 2.4.1.1), glycosylase (EC 3.1.33), sucrase-isomaltase (EC 3.2.10), amylomaltase (EC 2.4.1.25), maltase (EC 3.2.1.20), isoamylase, and α-glucan, water dikinase (GWD, EC 2.7.9.4).

30 Claims, 9 Drawing Sheets

Specification includes a Sequence Listing.

(56) References Cited

U.S. PATENT DOCUMENTS

| | | | |
|---|---|---|---|
| 7,791,010 B2 | 9/2010 | Abadeer | |
| 7,812,221 B2 | 10/2010 | Regina et al. | |
| 7,888,499 B2 | 2/2011 | Morell et al. | |
| 7,919,132 B2 | 4/2011 | Regina et al. | |
| 7,919,682 B2 | 4/2011 | Frohberg et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 8,501,262 B2 | 8/2013 | Bird et al. | |
| 2003/0066108 A1* | 4/2003 | Jilka | C07K 14/415 800/288 |
| 2003/0167529 A1 | 9/2003 | Landschutze et al. | |
| 2004/0123343 A1 | 6/2004 | La Rosa et al. | |
| 2004/0172684 A1 | 9/2004 | Kovalic et al. | |
| 2006/0015965 A1 | 1/2006 | Rahman et al. | |
| 2006/0150278 A1 | 7/2006 | Frohberg et al. | |
| 2009/0106863 A1 | 4/2009 | Frohberg et al. | |
| 2009/0119800 A1 | 5/2009 | Lanahan et al. | |
| 2011/0010807 A1 | 1/2011 | Morell et al. | |
| 2011/0281818 A1 | 11/2011 | Jenkins et al. | |
| 2012/0074247 A1 | 3/2012 | Regina et al. | |
| 2012/0114770 A1 | 5/2012 | Regina et al. | |
| 2012/0129805 A1 | 5/2012 | Li et al. | |
| 2012/0266267 A1 | 10/2012 | Li et al. | |
| 2013/0115362 A1 | 5/2013 | Regina et al. | |
| 2013/0156924 A1 | 6/2013 | Morell et al. | |

FOREIGN PATENT DOCUMENTS

| | | |
|---|---|---|
| WO | WO1999/53072 | 10/1999 |
| WO | WO2000/28052 | 5/2000 |
| WO | WO2000/077165 | 12/2000 |
| WO | WO2000/077229 | 12/2000 |
| WO | WO2002/101059 | 12/2002 |
| WO | WO2003/018766 | 3/2003 |
| WO | WO2003/071860 | 9/2003 |
| WO | WO2003/072791 | 9/2003 |
| WO | WO2005/002359 | 1/2005 |
| WO | WO2005/096804 | 10/2005 |
| WO | WO2007/009823 | 1/2007 |
| WO | WO2007/018770 | 2/2007 |
| WO | WO2008/017518 | 2/2008 |
| WO | WO2008/150880 | 12/2008 |
| WO | WO2009/000557 | 12/2008 |
| WO | WO2009/061720 | 5/2009 |

OTHER PUBLICATIONS

Written Opinion of the International Searching Authority, dated Feb. 25, 2009 in connection with PCT International Application No. PCT/AU2008/001759, of which the subject application is a §371(c) national stage entry.
European Supplemental Search Report, dated Jul. 25, 2011 by the European Patent Office in connection with corresponding European Patent Application No. 08853342.7.
GenBank Accession No. CF074015, Jul. 21, 2003.
GenBank Accession No. EH406623, Nov. 20, 2007.
GenBank Accession No. 00423248, Jun. 2, 2003.
GenBank Accession No. 31245998, Jul. 17, 2001.
Asatsuma et al., "Involvement of alpha-amylase I-1 in starch degradation in rice chloroplasts ." Plant Cell Physiology, (2005); 46(6):858-869.
Blennow et al., "The molecular deposition of transgenically modified starch in the starch granule as imaged by functional microscopy." Journal of Structural Biology, (2003); 143(3):229-241.
Kozlov et al., "Structural and thermodynamic properties of starches extracted from GBSS and GWD suppressed potato lines." International Journal of Biological Macromolecules, (2007) 40(5):449-460.

Lorberth et al., "Inhibition of a starch-granule-bound protein leads to modified starch and repression of cold sweetening." Nature Biotechnology, (1998); 16(1):473-477.
Mikkelsen et al., "A novel type carbohydrate-binding module identified in alpha-glucan, water dikinases is specific for regulated plastidial starch metabolism." Biochemistry, (2006); 45(14):4674-4682.
Abel et al., (1996) "Cloning and functional analysis of a cDNA encoding a novel 139 kDa starch synthase from potato (*Solanum tuberosum* L.)" The Plant Journal 10: 981-99.
Baunsgaard et al., (2005) "A novel isoform of glucan, water dikinase phosphorylates pre-phosphorylated α-glucans and is involved in starch degradation in *Arabidopsis*" The Plant Journal 41, 595-605.
Blennow et al., (2000) "The distribution of covalently bound phosphate in the starch granule in relation to starch crystallinity" Int. Biol. Macromol. 27: 211-218.
Blennow et al., (2000) "Starch molecular structure and phosphorylation investigated by a combined chromatographic and chemometric approach" Carbohydr. Polym. 41: 163-174.
Blennow et al., (2002) "Starch phosphorylation: a new front line in starch research" Trends in Plant Science 7: 445-450.
Ekman and Jager, (1993) "Quantification of Subnanomolar amounds of Phosphate Bound to Seryl and Threonyl Residues in Phosphoproteins Using alkaline Hydrolysis and Malachite Green" Anal Biochem 214: 138-141.
Jobling et al., (1999) "A minor form of starch branching enzyme in potato (*Solanum tuberosum* L.) tubers has a major effect on starch structure: cloning and characterization of multiple forms of SBE A" Plant Journal 18: 163-171.
Ral et al., (2012) "Down-regulation of Glucan, Water-Dikinase activity in wheat endosperm increases vegetative biomass and yield" Plant Biotechnology Journal 10, pp. 871-882.
Ral et al., (2013) Corrigendum "Down-regulation of Glucan, Water-Dikinase activity in wheat endosperm increases vegetative biomass and yield" Plant Biotechnology Journal pp. 1-2.
Ritte et al., (2006) "Phosphorylation of C6- and C3-positions of glucosyl residues in starch is catalysed by distinct dikinases" FEBS pp. 4872-4876.
Schwall et al., (2000) "Production of very-high-amylose potato starch by inhibition of SBE A and B" Nature Biotechnol. 18: 551-554.
Vikso-Nielsen et al., (2001) "Structural, Physicochemical, and Pasting Properties of Starches from Potato Plants with Repressed r1-Gene" Biomacromolecules 3: 836-841.
Vikso-Nielsen et al., (2001) "Production of highly phosphorylated glycopolymers by expression of R1 in *Escherichia coli*" Carbohydr. Res. 337, pp. 327-333.
Yu et al., (2001) "The *Arabidopsis* sex1 Mutant is Defective in the R1 Protein, a General Regulator of Starch Degradation in Plants, and Not in the Chloroplast Hexose Transporter" Plant Cell 13: 1907-1918.
Zeeman et al., (1998) "A starch-accumulating mutant of *Arabidopsis thaliana* deficient in a chloroplastic starch-hydrolysing enzyme" Plant Journal 15: 357-365.
Zeeman et al., (2004) "The Breakdown of Starch in Leaves" New Phytologist 163: 247-261.
Oct. 24, 2012 First Examination Report issued in connection with corresponding Australian Application No. 2008329557.
Nov. 27, 2012 Communication issued in connection with corresponding European Patent Application No. 08853342.7.
Jan. 27, 2011 Examination Report issued in connection with corresponding New Zealand Patent Application No. 586458.
Jul. 31, 2012 Examination Report issued in connection with corresponding New Zealand Patent Application No. 586458.
English Language Translation of Oct. 31, 2012 First Office Action issued in connection with corresponding Chinese Patent Application No. 200680125629.2.
English Language Translation of Aug. 20, 2012 First Office Action issued in connection with corresponding Eurasian Patent Application No. 201000873.

* cited by examiner

Parent line (■); Wild-type segregates (▨); Mutants (▨)

PLANTS WITH MODIFIED STARCH METABOLISM

This Application is the National Phase Under 35 U.S.C. § 371 of PCT International Application No, PCT/AU2008/001759 which has an International filing date of Nov. 27, 2008, which claims priority to Australian Application No. 2007906467 filed on Nov. 27, 2007. The entire contents of all applications listed above are hereby incorporated by reference.

FIELD

The specification describes methods for increasing the production potential of an organism. More particularly, the specification considers starch metabolism in plants and provides plants including Graminaceous plants such as wheat and barley having modified starch metabolism and production potential. The specification describes various methods for producing plants having modified production potential such as increased yield, growth, biomass, vigour, etc., and methods for producing products of interest from the modified plants.

BACKGROUND

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Plants are the primary source of reusable energy and methods for enhancing the production potential of a given plant are highly sought after. Starch is the major carbohydrate reserve in plants and also the major energy-providing component in human diets. The importance of starch functionality on end product quality, for example in foods, has recently gained increased recognition. Starch textural properties are also important in industrial (non-food) applications where the starch is used as a gelling agent, bulking agent, water retention agent or adhesive, for example.

In cereals, starch makes up approximately 45-65% of the weight of the mature grain. Starch is composed only of glucosidic residues but is found as two types of molecules, amylose and amylopectin, which can be distinguished on the basis of molecular size or other properties. Amylose molecules are essentially linear polymers composed of α-1,4 linked glucosidic units, while amylopectin is a highly branched molecule with α-1,6 glucosidic bonds linking many linear chains of α-1,4 linked glucosidic units. Amylopectin is made of large molecules ranging in size between several tens of thousands to hundreds of thousands of glucose units with around 5 percent α-1,6 branches. Amylose on the other hand is composed of molecules ranging in size between several hundreds to several thousand glucosidic residues with less than one percent branches (for review see Buleon et al., 1998). Wild-type cereal starches typically contain 20-30% amylose while the remainder is amylopectin.

Starch is initially synthesized in plants in chloroplasts of photosynthesizing tissues such as leaves in the form of transitory starch. This is mobilized during subsequent dark periods to supply carbon for export to sink organs and energy metabolism, or for storage in organs such as seeds or tubers. Synthesis and long-term storage of starch occurs in the amyloplasts of the storage organs, where the starch is deposited as semicrystalline granules up to 100 μm in diameter. Granules contain both amylose and amylopectin, the former typically as amorphous material in the native starch granule while the latter is semicrystalline through stacking of the linear glucosidic chains.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and adenosine triphosphate (ATP). Secondly, the activated glucosyl donor, ADP-glucose, is transferred to the non-reducing end of a pre-existing α-1,4 linkage by starch synthases. Thirdly, starch branching enzymes introduce branch points through the cleavage of a region of α-1,4 linked glucan followed by transfer of the cleaved chain to an acceptor chain, forming a new α-1,6 linkage. Starch branching enzymes are the only enzymes that can introduce the α-1,6 linkages into α-polyglucans and therefore play an essential role in the formation of amylopectin. Finally, starch debranching enzymes remove some of the branch linkages although the mechanism through which they act is unresolved.

While it is clear that at least these four activities are required for normal starch granule synthesis in higher plants, multiple isoforms of each of the four activities are found in the endosperm of higher plants and specific roles have been proposed for individual isoforms on the basis of mutational analysis or through the modification of gene expression levels using transgenic approaches (Abel et al., 1996, Jobling et al., 1999, Schwall et al., 2000). However, the precise contributions of each isoform of each activity to starch biosynthesis are still not known, and these contributions may differ markedly between species. In the cereal endosperm, two isoforms of ADP-glucose pyrophosphorylase are present, one form within the amyloplast, and one form in the cytoplasm (Denyer et al., 1996, Thorbjornsen et al., 1996). Four classes of starch synthase are found in the cereal endosperm, an isoform exclusively localized within the starch granule, granule-bound starch synthase (GBSS) which is essential for amylose synthesis, two forms that are partitioned between the granule and the soluble fraction (SSI, Li et al., 1999a, SSII, Li et al., 1999b) and a fourth form that is entirely located in the soluble fraction, SSIII (Cao et al, 2000, Li et al., 1999b, Li et al, 2000). Mutations in SSII and SSIII have been shown to alter amylopectin structure (Gao et al, 1998, Craig et al., 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, 1982, Boyer and Preiss, 1978, Mizuno et al., 1992, Sun et al., 1997). Genomic and cDNA sequences have been characterized for rice (Nakamura and Yamanouchi, 1992), maize (Baba et al., 1991; Fisher et al., 1993; Gao et al., 1997) and wheat (Repellin et al., 1997; Nair et al., 1997; Rahman et al., 1997). Sequence alignment reveals a high degree of sequence similarity at both the nucleotide and amino acid levels and allows the grouping into the SBEI, SBEIIa and SBEIIb classes. SBEIIa and SBEIIb generally exhibit around 80% sequence identity to each other, particularly in the central regions of the genes.

Two types of debranching enzymes are present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (James et al., 1995; Kubo et al., 1999) however the causal mutation maps to the same location as the isoamylase-type debranching enzyme gene.

Starches extracted from almost all plant species are phosphorylated to some extent. The extent of phosphorylation is usually in the range of 0.1-0.4% of the glucosidic residues, which are phosphorylated at the carbone 3 or the carbone 6 of glucosyl units as phosphate monoesters (Blennow et al, 2000a). Typically, about 80% of the phosphate groups are bound at the C-6 positions, and about 20% at C-3. However, the degree of phosphorylation varies considerably with the botanical source. Starch from potato tuber displays an average of 25 nmoles of glucose-6-phosphate per mg starch while cereal starches display only ¹/₁₀th of this amount of glucose-6-phosphate in reserve starch. The presence of phosphate groups in starch affects the water absorption capacity of starch pastes after gelatinization and viscosity properties.

Starch phosphorylation is catalyzed by a group of enzymes belonging to the dikinase family. Two enzymes that carry out starch phosphorylation have been identified in potato and *Arabidopsis*, namely α-Glucan, Water-Dikinase (GWD; EC 2.7.9.4, otherwise known as the R1 protein or OK1), and Phosphoglucan, Water Dikinase (PWD; EC 2.7.9.5). The former catalyses the transfer of the β-phosphate of ATP to either the C-3 or C-6 position of the glucosyl residue and the γ-phosphate to a water molecule, releasing orthophosphate, while the latter catalyses transfer of phosphates to phosphoglucan (already phosphorylated by GWD) and to water (Baunsgaard et al., 2005; Kotting et al., 2005). More recently Ritte et al. suggested that the phosphorylation in position 3 or 6 of glucosyl residues in starch is catalyzed by the PWD and the GWD respectively (Ritte G. et al., 2006).

Antisense repression of a gene encoding GWD in potatoes reduced starch bound phosphate content by 80% (Viksø-Nielsen et al., 2001). Furthermore, a mutation in a gene designated Sex1 (Starch Excess phenotype) in *Arabidopsis thaliana* abolished starch phosphorylation, confirming the involvement of GWD as the enzyme responsible (Zeeman and Rees, 1999). In addition both the *Arabidopsis* mutant and the transgenic antisense potatoes displayed a starch excess phenotype in the leaves, demonstrating a role of GWD in the degradation of transitory starch. Aside from the suppression of starch phosphorylation, no modification of the starch structure was observed in those plants. However, the GWD antisense potatoes showed a reduction in the "cold sweetening" phenotype in tubers as well as the starch excess phenotype in the leaves (Lorberth et al., 1998). The potato plants also showed an increase in tuber number associated with a decrease of individual tuber weight, but did not show any other effect on starch accumulation in the tuber. The *Arabidopsis* sex1 mutants which were affected in their transitory starch metabolism also had altered carbohydrate metabolism, grew slowly and flowered late (Yu et al., 2001).

The relationship between starch degradation and starch phosphate content remains unclear. The starch produced by the antisense lines from potato displayed a high resistance to β-amylase degradation, suggesting that starch phosphorylation may be a prerequisite for degradation by β-amylase. Phosphorylated residues could be a targeting signal for this enzyme in order to degrade starch during the night period. Some studies have suggested an association of α-amylase and the R1 (GWD) protein with the starch granule before the degradation initiated.

Starch degradation and phosphorylation in germinating cereal seeds such as wheat is less understood and is a highly specialized system involving tissue deterioration and induction of hydrolytic enzymes as well as starch degradation.

Wheat is a staple food in many countries and supplies approximately 20% of the food kilojoules for the total world population. The processing characteristics of wheat make it the preferred base for most cereal-based processed products such as bread, pasta and noodles. Wheat consumption is increasing world-wide with increasing affluence. Breadwheat (*Triticum aestivum*) is a hexaploid having three different genomes, A, B and D, and most of the known genes in wheat are present in triplicate, one on each genome. The hexaploid nature of the breadwheat genome makes finding and combining gene mutations in each of the three genomes a challenge. The presence of three genomes has a buffering effect by masking mutations in individual genomes, in contrast to the more readily identified mutations in diploid species. Known variation in wheat starch structure has been limited relative to the variation available in maize or rice. Another contributing factor to this is that the transformation efficiency of wheat has lagged behind that for other cereals. It is believed that genes involved in starch phosphorylation in wheat and their effects have not been studied previously, and it is unknown whether effects observed on starch phosphorylation in potato and *Arabidopsis*, both dicots, could be similarly replicated in monocot species such as wheat.

SUMMARY

The present invention is predicated, in part, on the discovery that modification of endogenous starch phosphorylation and/or degradation in plants alters the production capacity of the plant. In some embodiments, this leads to increased production potential as seen in attributes such as, without limitation, increased or improved biomass, vigour, germination, seedling vigour, growth rate, height, total leaf area, photosynthetic rate per leaf area, number of leaves per plant, number of heads per plant, number of tillers per plant, number of seeds per plant, number of seeds per head, average seed weight, total seed weight per plant, starch content or composition of seeds or tubers, stem thickness, number of internodes, number of branches, number of flowers, flower size or shape, flower colour, number of pods per plant, pod size, number of seeds per pod, number of fruit per plant, fruit set, fruit size, fruit shape, fruit colour, fruit quality, disease resistance, root mass, number of roots, length of roots, and/or yield and/or delayed senescence compared to a control plant. In other embodiments, plants have increased endogenous glycosylase and/or digestibility compared to a control plant.

Accordingly, in one embodiment, the specification describes methods of improving the production potential of plants by modifying endogenous starch phosphorylation and/or starch degradation in the plant. In some embodiments, the methods comprise obtaining a genetically modified plant which has increased production potential compared to a control plant. In some embodiments, the method comprises the steps of i) obtaining a plurality of plants at least one of which comprises in its genome a heterologous polynucleotide, ii) identifying from the plurality of plants a plant which has increased production potential relative to the control plant and comprises the heterologous polynucleotide. In some embodiments, the method comprises iii)

selecting the genetically modified plant, wherein the polynucleotide comprises a transcriptional control sequence operably linked to a nucleic acid sequence which encodes an agent that modifies endogenous starch phosphorylation and/or starch degradation in the plant.

In another embodiment, the specification describes a method of obtaining a genetically modified plant which has increased endogenous glycosylase compared to a control plant. In some embodiments, the method comprises the steps of i) obtaining a plurality of plants at least one of which comprises in its genome a heterologous polynucleotide, ii) identifying from the plurality of plants a plant which has increased endogenous glycosylase relative to the control plant and comprises the heterologous polynucleotide. In some embodiments, the method comprises iii) selecting the genetically modified plant, wherein the polynucleotide comprises a transcriptional control sequence operably linked to a nucleic acid sequence which encodes an agent that modifies endogenous starch phosphorylation and/or starch degradation in the plant.

In another embodiment, the specification describes a method of obtaining a genetically modified plant which has increased digestibility of at least one of its parts compared to a control plant, the method comprising the steps of i) obtaining a plurality of plants at least one of which comprises in its genome a heterologous polynucleotide, ii) identifying from the plurality of plants a genetically modified plant which has increased digestibility of at least one of its parts relative to the control plant and comprises the heterologous polynucleotide. In some embodiments, the method comprises iii) selecting the genetically modified plant, wherein the polynucleotide comprises a transcriptional control sequence operably linked to a nucleic acid sequence which encodes an agent that modifies endogenous starch phosphorylation and/or starch degradation in the plant.

In a further related embodiment, the specification describes a method of determining whether a genetically modified plant has increased production potential, increased endogenous glycosylase, or increased digestibility of at least one of its parts, compared to a control plant, the method comprising the steps of i) obtaining one or more plants which comprise in their genomes a heterologous polynucleotide, and ii) determining whether the one or more plants have an increased production potential, increased endogenous glycosylase or increased digestibility, of at least one of its parts relative to the control plant, and wherein the polynucleotide comprises a transcriptional control sequence operably linked to a nucleic acid sequence which encodes an agent that modifies endogenous starch phosphorylation and/or starch degradation in the plant.

Preferably, step ii) directed to identifying or determining increased production potential, increased endogenous glycosylase activity or increased digestibility comprises evaluating a phenotype which is, and/or identifying a plant which has, modified starch content or composition such as the level of starch phosphorylation, increased production potential, increased endogenous glycosylase in at least some of its cells or organs, or increased digestibility of at least one of its parts relative to the control plant.

The specification also describes a method of identifying a gene involved in increased production potential in a plant compared to a control plant, the method comprising the steps of i) obtaining a plurality of plants each of which comprises in its genome a heterologous polynucleotide, ii) measuring the production potential of each plant and optionally whether they have increased endogenous glycosylase or increased digestibility of at least one of its parts relative to the control plant, iii) identifying a plant having increased production potential, and iv) identifying the heterologous polynucleotide therein, thereby identifying the gene wherein the polynucleotide comprises a transcriptional control sequence operably linked to a nucleic acid sequence which encodes an agent that modifies endogenous starch phosphorylation and/or starch degradation in the plant.

The specification further describes a method of identifying a polynucleotide which is capable of increasing production potential of a plant, increasing endogenous glycosylase in a plant, or increased digestibility of at least one part of a plant compared to a control plant, the method comprising the steps of i) obtaining one or more heterologous polynucleotides each comprising a transcriptional control sequence operably linked to a nucleic acid sequence which encodes an agent that modifies endogenous starch phosphorylation and/or starch degradation in the plant, ii) introducing the heterologous polynucleotide(s) into progenitor cells, tissues, organs, seeds or plants, iii) generating a plurality of plants therefrom, iv) determining whether at least one plant comprising a heterologous polynucleotide has an increased production potential, increased endogenous glycosylase or increased digestibility of at least one of its parts relative to the control plant, and v) selecting the polynucleotide.

In an embodiment, the specification provides a method of producing a genetically modified plant which has increased production potential, increased endogenous glycosylase, or increased digestibility of at least one of its parts, compared to a control plant. In some embodiments, the method comprises the steps of i) obtaining a heterologous polynucleotide comprising a transcriptional control sequence operably linked to a nucleic acid sequence which encodes an agent that modifies endogenous starch phosphorylation and/or starch degradation in the plant, ii) introducing the heterologous polynucleotide into progenitor cells, tissues, organs, seeds or plants, iii) obtaining a plurality of plants therefrom at least one of which comprises in its genome the heterologous polynucleotide, iv) identifying a plant from the plurality of plants which has an increased production potential, increased endogenous glycosylase or increased digestibility of at least one of its parts relative to the control plant and comprises the heterologous polynucleotide, and v) selecting the plant, thereby producing the genetically modified plant. In another embodiment, the method comprises the steps of i) mutagenesis of progenitor cells, tissues, organs, seeds or plants, ii) obtaining a plurality of plants therefrom at least one of which comprises in its genome a heterologous polynucleotide comprising a transcriptional control sequence operably linked to a nucleic acid sequence that modifies endogenous starch phosphorylation and/or starch degradation in the plant, and iii) identifying a plant from the plurality of plants which has an increased production potential, increased endogenous glycosylase or increased digestibility of at least one of its parts relative to the control plant.

The subject heterologous polynucleotide may be introduced into the plant by any suitable method. In some embodiments, the methods comprise the step of introducing the heterologous polynucleotide into progenitor cells, tissues, organs, seeds or plants, and generating the plurality of plants therefrom. In other embodiments, the step comprises transformation and/or mutagenesis of a progenitor cell, tissue, organ, seed or plant.

In some embodiments, the subject agent down regulates the expression of a gene encoding an enzyme involved in endogenous starch phosphorylation and/or starch degradation or the functional activity thereof. In particular embodiments, the agent down regulates endogenous starch phosphorylation in the plant.

In some embodiments, the present methods further comprises testing a nucleic acid sample from the plant for a mutation in a gene encoding a polypeptide involved in starch degradation and/or starch phosphorylation.

In some embodiments, endogenous starch phosphorylation and/or starch degradation is modified by modifying expression or activity of one or more enzymes or regulatory proteins involved in starch degradation and/or starch phosphorylation. Exemplary enzymes are selected from the group consisting of α-amylase (EC 3.2.1.1), β-amylase (EC 3.2.1.2), glucoamylase (EC 3.2.1.3), starch phosphorylase (EC2.4.1.1), glycosylase (EC 3.1.33), sucrase-isomaltase (EC 3.2.10), amylomaltase (EC 2.4.1.25), maltase (EC 3.2.1.20), isoamylase, and α-glucan, water dikinase (GWD, EC 2.7.9.4). In particular embodiments, endogenous starch phosphorylation and/or starch degradation is modified by increasing the expression or activity of α-amylase or β-amylase, and/or decreasing the expression or activity of GWD. In some embodiments, the subject methods further comprise decreasing the expression or activity of phosphoglycan, water dikinase (PWD, EC 2.7.9.5). In preferred embodiments, the regulatory protein is not the protein encoded by the sex1 and/or sex4 genes in *Arabidopsis* and/or potato.

In some embodiments, the subject agent is expressed in a storage organ of the plant, such as developing seed, root, tuber or stem. In particular embodiments, the agent is expressed in photosynthetically active tissue of the plant. In further particular embodiments, the endogenous starch phosphorylation and/or starch degradation is of transitory starch.

In some exemplary embodiments pertaining to increased endogenous glycosylase, the glycosylase is α-amylase, β-amylase, glucoamylase or glycosylase or combinations thereof.

The methods described in this specification are not limited to a particular plant type. Reference to a plant includes a plant selected from grasses, vegetables, cereals, legumes and fruit- or flower-bearing plants. In some embodiments, the cereal is wheat, corn (maize), barley, rice, rye, oats, millet, sorghum, triticale, buckwheat, fonio, quinoa, spelt, durum wheat, breadwheat, einkorn, amaranth, wild rice or teff.

In some embodiments of the above described methods, the subject genetically modified plants further comprise a heterologous polynucleotide which encodes an agent that down regulates α-amylase or β-amylase expression or activity, operably connected to a transcriptional control sequence, or a mutation in a gene encoding α-amylase or β-amylase. In some embodiments, a plant is selected which has reduced α-amylase or β-amylase expression or activity in at least one organ of the plant. In some embodiments, the agent is expressed in a storage organ or the gene encoding α-amylase or β-amylase is expressed in a storage organ. In other embodiments, the agent is an RNA molecule which down-regulates expression of a di-kinase enzyme. In some embodiments combinations of glycoylases are down regulated such as α-amylase and β-amylase.

In another aspect, the present invention provides plants, plant parts and plant products produced by the methods of the invention, uses thereof and processes for using the plants, parts or products. The plants or plant parts may be modified according to any of the features described herein in the context of the methods, or any combination thereof. Accordingly, the present invention provides genetically modified plants obtained, produced or identified by the herein disclosed methods. Reference to a plant or a part of a plant includes a plant part that is a seed, leaf, stem, root, tuber, flower, fruit, pod or cutting obtained from the plant.

More specifically, the specification describes a genetically modified plant comprising in its genome a heterologous polynucleotide comprising a transcriptional control sequence operably linked to a nucleic acid sequence which encodes an agent that modifies endogenous starch phosphorylation and/or starch degradation in the plant, wherein the plant is characterized by having modified starch phosphorylation and/or starch degradation and additionally having increased production potential, increased endogenous glycosylase, and/or increased digestibility of at least one of its parts, compared to a control plant.

Accordingly, in some embodiments the specification provides a genetically modified plant comprising in its genome an introduced mutation in a gene which encodes an endogenous starch phosphorylation polypeptide and/or starch degradative enzyme, wherein the plant is characterized by having modified starch phosphorylation and/or starch degradation and additionally having increased production potential, increased endogenous glycosylase, and/or increased digestibility of at least one of its parts, compared to a control plant.

In other embodiments, the specification provides a genetically modified plant comprising in its genome one or more heterologous polynucleotides each comprising a transcriptional control sequence operably linked to a nucleic acid sequence which encodes an agent that modifies endogenous starch phosphorylation and/or starch degradation in the plant, wherein the plant is characterized by having reduced starch phosphorylation and/or starch degradation in at least one part of the plant, increased or reduced glycosylase, preferably amylase, expression and/or activity in the mature seed of the plant, and increased production potential, compared to a control plant. In other embodiments, the plants exhibit a decreased level of a targeted starch phosphorylation polypeptide and/or starch degradative enzyme in at least a first organ of the plant and optionally an increased level of a starch phosphorylation polypeptide and/or starch degradative enzyme in at least a second organ of the plant, wherein the first and second organs are the same or different organs. In some embodiments, the targeted polypeptide or enzyme is selected from the group consisting of α-amylase, β-amylase, glucoamylase, starch phosphorylase, glycosylase, sucrase-isomaltase, amylomaltase, maltase, isoamylase and α-glucan, water dikinase.

In an exemplary embodiment, the agent down regulates the expression or functional activity of an enzyme involved in endogenous starch phosphorylation and/or starch degradation. In some embodiments, the agent down regulates the level or functional activity of a dikinase. In some embodiments, the di-kinase is GWD or GWD and PWD.

In some embodiments, the agent is expressed in a storage organ of the plant. In other embodiments, the agent is expressed in photosynthetically active tissue of the plant. In an exemplary embodiment, the starch phosphorylation and/or starch degradation is of transitory starch.

The invention also provides cereal grain with reduced starch phosphorylation in the leaves and/or grain and increased glycosylase in the grain. The combination of these two features provides particular advantages for the use of the grain, optionally in addition to increased plant productivity. The reduction in starch phosphorylation in the combination is by at least 50%, preferably at least 70%, at least 80%, at least 90% or at least 95% relative to a corresponding control plant. The increased glycosylase, preferably α-amylase, in the combination is increased by at least 100%, preferably at least 200%, at least 300% or more preferably at least 500% relative to the corresponding control plant.

The plant compositions described in this specification are not limited to a particular plant type. Reference to a plant includes a plant selected from angiosperms, monocotyledonous plants, dicotyledonous plants, grasses, vegetables, cereals, legumes and fruit- or flower-bearing plants, or any combination of these classifications to form a sub-class. In some embodiments, modified dicotyledonous plants are improved. In particular embodiments, graminaceous monocotyledonous plants are improved such as cereal crops, sugar cane, sugar beet, sorghum, *secale*, etc.

In some embodiments, the cereal is wheat, corn (maize), barley, rice, rye, oats, millet, sorghum, buckwheat, fonio, quinoa, spelt, durum wheat, breadwheat, einkorn, amaranth, wild rice or teff. The wheat may be breadwheat (hexaploid wheat), durum wheat or triticale. The corn is preferably dent corn and may be white corn or yellow corn. In some embodiments, the plant is a plant other than *Arabidopsis thaliana* and/or maize.

In some embodiments, the transcription control sequence preferentially directs expression of the polynucleotide in a storage organ and/or in plant tissue that is photosynthetically active.

In other embodiments, the plant further comprises a polynucleotide operably connected to a transcriptional control sequence which encodes an agent that down regulates amylase activity.

In other embodiments, the plant part is characterized in having a modified starch content or composition, increased production potential, increased endogenous glycosylase or increased digestibility, relative to the corresponding part of a control plant.

In a particular embodiment, the specification provides a seed, comprising starch, wherein the level of glucose-6-phosphate in the starch of the seed is less than 10 ng/mg starch and the level of amylase activity in flour obtained from the seed is at least 4 units/g flour.

The present specification contemplates a product of the herein described genetically modified plant.

In one embodiment, the specification provides a product which is processed grain, flour, wholemeal or at least partly purified starch, wherein the product has a modified starch content or total starch composition relative to the corresponding product from a control plant.

The specification discloses a process of producing such a product, comprising growing the plant and/or harvesting the plant or a part of the subject genetically modified plant. In some embodiments, the process is for producing processed grain, flour, wholemeal or at least partly purified starch and comprises processing a plant part, such as grain, from the herein disclosed genetically modified plants.

In other embodiments, the specification provides a process of producing a food product, comprising mixing the herein described plant or part of the plant or the herein described product of the herein described plant with another food ingredient and optionally cooking, baking, frying, steaming, boiling, extruding or otherwise processing the mixture.

In another embodiment, the product is a product of fermentation and the specification describes a process comprising fermenting a product which is a processed grain, flour, wholemeal or at least partly purified starch and wherein the product has a modified starch content or modified total starch composition relative to the corresponding product from a control plant, or the flour or starch produced by processing a plant part, such as grain, from the herein disclosed genetically modified plants. In some embodiments, the fermentation product is ethanol.

In yet another embodiment, the specification provides a process of feeding a human or animal, comprising providing the herein or hereinabove described genetically modified plant, plant part, product, or product produced by the process to the human or animal. In some embodiments, the specification provides a product produced by an above or herein described process.

In another aspect, the subject specification discloses the use of a heterologous polynucleotide to produce a plant characterized by increased production potential, increased endogenous glycosylase, or increased digestibility of its seed or of at least one of its organs, compared to a control plant, wherein the polynucleotide comprises a transcriptional control sequence operably linked to a nucleic acid sequence encoding an agent which modifies endogenous starch phosphorylation and/or starch degradation in the plant.

In another embodiment, the specification provides for the use of the herein or hereinabove described genetically modified plant or a part thereof comprising starch, for the production of a food product or a non-food product, or as animal feed for enhancing the growth or health of animals. In some embodiments, the product is ethanol.

In another embodiment, the specification discloses the use of a plant or part thereof for the manufacture of a food substance for human consumption, wherein the plant or part thereof is genetically modified by the introduction of at least two heterologous polynucleotides, wherein the plant is characterized by the increased production potential, reduced starch phosphorylation and/or starch degradation in the leaves of the plant and reduced endogenous glycosylase in the seed of the plant, wherein each heterologous polynucleotide comprises a transcriptional control sequence operably linked to a nucleic acid sequence which encodes an agent that modifies endogenous starch phosphorylation and/or starch degradation in the plant.

In another embodiment, the specification provides a method of identifying or using a molecular marker of plant production potential, increased endogenous glycosylase, or increased digestibility of seed or at least one other part of a plant compared to a control plant, the method comprising obtaining a sample of nucleic acid from a plant and treating the sample to identify a polymorphism in, or genetically linked to, a gene encoding GWD in the plant.

In another embodiment, the specification provides a method of evaluating a plant, comprising obtaining a sample of nucleic acid from a plant and treating the sample to determine the identity of selected nucleotides in a GWD gene; and associating any identified nucleotide with an attribute related to production potential in the plant.

The present specification provides novel nucleic acid molecules. In one embodiment, the specification describes an isolated or chimeric nucleic acid molecule comprising a nucleotide sequence encoding or complementary to a sequence encoding an α-glucan, water dikinase polypeptide comprising the amino acid sequence of SEQ ID NO: 3 or a biologically active portion thereof or a variant thereof having at least 90% sequence identity to SEQ ID NO: 3.

In another embodiment, the specification provides an isolated or chimeric nucleic acid molecule comprising a nucleotide sequence that corresponds to or is complementary to SEQ ID NO: 2 or SEQ ID NO: 5 or SEQ ID NO: 8, SEQ ID NO: 9 or SEQ ID NO: 10 (rice GWD) or to SEQ ID NO: 11, 12, 13 or 14 (sorghum GWD) or to a protein encoding or a biologically active portion thereof, or to a variant thereof having at least 90% sequence identity to SEQ ID NO: 2 (wheat GWD) or SEQ ID NO: 5 (wheat GWD) or SEQ ID NO: 8, 9 or 10 (rice GWD) or to SEQ ID NO: 11, SEQ ID NO: 12, SEQ ID NO: 13 or SEQ ID NO: 14 (sorghum GWD) or protein encoding region thereof.

In some embodiment, the specification describes an isolated or chimeric nucleic acid molecule comprising a nucleotide sequence that hybridizes under high stringency conditions to SEQ ID NO: 2 or SEQ ID NO: 5 or SEQ ID NO: 8, 9 or 10 or to a protein encoding or biologically active portion thereof, or to a variant thereof having at least 90% sequence identity to SEQ ID NO: 2 (wheat GWD) or SEQ ID NO: 5 (wheat GWD) or SEQ ID NO: 8, SEQ ID NO: 9 or SEQ ID NO: 10 (rice GWD) or to SEQ ID NO: 11, SEQ ID NO: 12, SEQ ID NO: 13 or SEQ ID NO: 14 (sorghum GWD) or protein encoding region thereof.

In some embodiments, the specification provides a chimeric nucleic acid construct comprising a nucleic acid molecule as herein described operably linked to transcriptional control sequence. In some embodiments, the specification provides an isolated or chimeric nucleic acid molecule capable of reducing the expression of a gene encoding a polypeptide having GWD activity in a cereal plant. In some embodiments, the nucleic acid is or encodes an RNA which is an antisense RNA, cosuppression RNA, duplex RNA, hairpin RNA or ribozyme.

In some embodiments the specification describes the use of an isolated or chimeric nucleic acid molecule to reduce the expression of a gene encoding a polypeptide having GWD activity in a cereal plant.

In another embodiment, the specification provides a single stranded nucleic acid probe comprising 20 consecutive nucleotides, wherein the nucleotide sequence of the 20 nucleotides is identical to the complement of a nucleotide sequence of a nucleic acid molecule comprising a nucleotide sequence of SEQ ID NO: 2 or SEQ ID NO: 5 or SEQ ID NO: 8, 9 or 10 (rice PWD) or to SEQ ID NO: 11, SEQ ID NO: 12, SEQ ID NO: 13 or SEQ ID NO: 14 (sorghum GWD) or to a protein encoding or a biologically active portion thereof, or to a variant thereof having at least 90% sequence identity to SEQ ID NO: 2 (wheat GWD) or SEQ ID NO: 5 (wheat GWD) or SEQ ID NO: 8, SEQ ID NO: 9 or SEQ ID NO: 10 (rice PWD) or to SEQ ID NO: 11, SEQ ID NO: 12, SEQ ID NO: 13 or SEQ ID NO: 14 (sorghum GWD) or protein encoding region thereof.

In another embodiment, the specification provides a single stranded nucleic acid probe comprising 20 consecutive nucleotides, wherein the nucleotide sequence of the 20 nucleotides is identical a nucleotide sequence of nucleic acid molecule comprising a nucleotide sequence that hybridizes under high stringency conditions to SEQ ID NO: 2 or SEQ ID NO: 5 or SEQ ID NO: 8, SEQ ID NO: 9 or SEQ ID NO: 10 (rice PWD) or to SEQ ID NO: 11, SEQ ID NO: 12, SEQ ID NO: 13 or SEQ ID NO: 14 (sorghum GWD) or to a protein encoding or biologically active portion thereof, or to a variant thereof having at least 90% sequence identity to SEQ ID NO: 2 (wheat GWD) or SEQ ID NO: 5 (wheat GWD) or SEQ ID NO: 8, SEQ ID NO: 9 or SEQ ID NO: 10 (rice PWD) or to SEQ ID NO: 11, SEQ ID NO: 12, SEQ ID NO: 13 or SEQ ID NO: 14 (sorghum GWD) or protein encoding region thereof.

In another embodiment, the specification provides a single stranded nucleic acid probe comprising 20 consecutive nucleotides, wherein the nucleotide sequence of the 20 nucleotides is identical to the complement of a nucleotide sequence of a nucleic acid comprising a nucleotide sequence encoding an α-glucan, water dikinase polypeptide comprising the amino acid sequence of SEQ ID NO: 3 or a biologically active portion thereof or a variant thereof having at least 90% sequence identity to SEQ ID NO: 3.

In another embodiment, the present specification provides an array of nucleic acid molecules attached to a solid support, the array comprising a oligonucleotide which will selectively hybridize to a nucleic acid molecule comprising a gene encoding a polypeptide having GWD activity in a cereal plant.

In another embodiment, the specification provides an expression vector, host cell, plant cell, plant part, plant or seed comprising the above described isolated or chimeric nucleic acid molecule, or a construct comprising said nucleic acid molecule operably linked to a transcriptional control sequence. In some embodiments the construct is expressed in a host cell, plant cell, plant, plant part or seed and the specification provides a method of producing a cereal GWD polypeptide or variant thereof, or a method of producing a biologically active fragment or a variant thereof is provides, said method comprising expressing the construct in a host cell, plant cell, plant, plant part or seed.

Accordingly, in some embodiments, the specification provides methods of improving plants, the method comprising the steps of i) obtaining a plurality of plants at least one of which comprises in its genome a heterologous polynucleotide, ii) identifying from the plurality of plants a modified plant which has increased production potential relative to the control plant and comprises the heterologous polynucleotide, and iii) selecting the genetically modified plant, wherein the polynucleotide comprises a transcriptional control sequence operably linked to a nucleic acid sequence which encodes an agent that modifies endogenous starch phosphorylation and/or starch degradation in the plant wherein the genetically modified plant has increased production potential relative to a control plant.

In another related embodiment, the specification describes a method of improving a plant, the method comprising the steps of i) obtaining a plurality of plants at least one of which comprises in its genome a heterologous polynucleotide, ii) identifying from the plurality of plants a genetically modified plant which has increased endogenous glycosylase relative to the control plant and comprises the heterologous polynucleotide, and iii) selecting the genetically modified plant, wherein the polynucleotide comprises a transcriptional control sequence operably linked to a nucleic acid sequence which encodes an agent that modifies endogenous starch phosphorylation and/or starch degradation in the plant, wherein the genetically modified plant has increased endogenous glycosylase compared to a control plant.

In yet another embodiment, the specification describes a method of improving plants, said method comprising the steps of i) obtaining a plurality of plants at least one of which comprises in its genome a heterologous polynucleotide, ii) identifying from the plurality of plants a genetically modified plant which has increased digestibility of at least one of its parts relative to the control plant and comprises the heterologous polynucleotide, and iii) selecting the genetically modified plant, wherein the polynucleotide comprises a transcriptional control sequence operably linked to a nucleic acid sequence which encodes an agent that modifies endogenous starch phosphorylation and/or starch degradation in the plant, wherein the genetically modified plant has increased digestibility of at least one of its parts compared to a control plant.

In a further embodiment, the specification describes a method of improving plants, said method comprising the steps of i) obtaining one or more plants which comprise in their genomes a heterologous polynucleotide, and ii) determining whether the one or more plants have an increased production potential, increased endogenous glycosylase or increased digestibility of at least one of its parts relative to the control plant, wherein the polynucleotide comprises a transcriptional control sequence operably linked to a nucleic acid sequence which encodes an agent that modifies endogenous starch phosphorylation and/or starch degradation in the plant, wherein thegenetically modified plant has increased production potential, increased endogenous glycosylase, or increased digestibility of at least one of its parts, compared to a control plant, In a further embodiment, the specification describes a method of improving plants, said method comprising the steps of i) obtaining a heterologous polynucleotide comprising a transcriptional control sequence operably linked to a nucleic acid sequence which encodes an agent that modifies endogenous starch phosphorylation and/or starch degradation in the plant, ii) introducing the heterologous polynucleotide into progenitor cells, tissues, organs, seeds or plants, iii) obtaining a plurality of plants therefrom at least one of which comprises in its genome the heterologous polynucleotide, iv) identifying a plant from the plurality of plants which has an increased production potential, increased endogenous glycosylase or increased digestibility of at least one of its parts relative to the control plant and comprises the heterologous polynucleotide, and v) selecting the plant, thereby producing the genetically modified plant, wherein the genetically modified plant has increased production potential, increased endogenous glycosylase, or increased digestibility of at least one of its parts, compared to a control plant.

In a further embodiment, the specification describes a method of improving plants, said method comprising the steps of i) mutagenesis of progenitor cells, tissues, organs, seeds or plants, ii) obtaining a plurality of plants therefrom at least one of which comprises in its genome a heterologous polynucleotide comprising a transcriptional control sequence operably linked to a nucleic acid sequence, which encodes an agent that modifies endogenous starch phosphorylation and/or starch degradation in the plant, and iii) identifying a plant from the plurality of plants which has an increased production potential, increased endogenous glycosylase or increased digestibility of at least one of its parts relative to the control plant, wherein the genetically modified plant has increased production potential, increased endogenous glycosylase, or increased digestibility of at least one of its parts, compared to a control plant.

BRIEF DESCRIPTION OF THE TABLES

Figure 1:
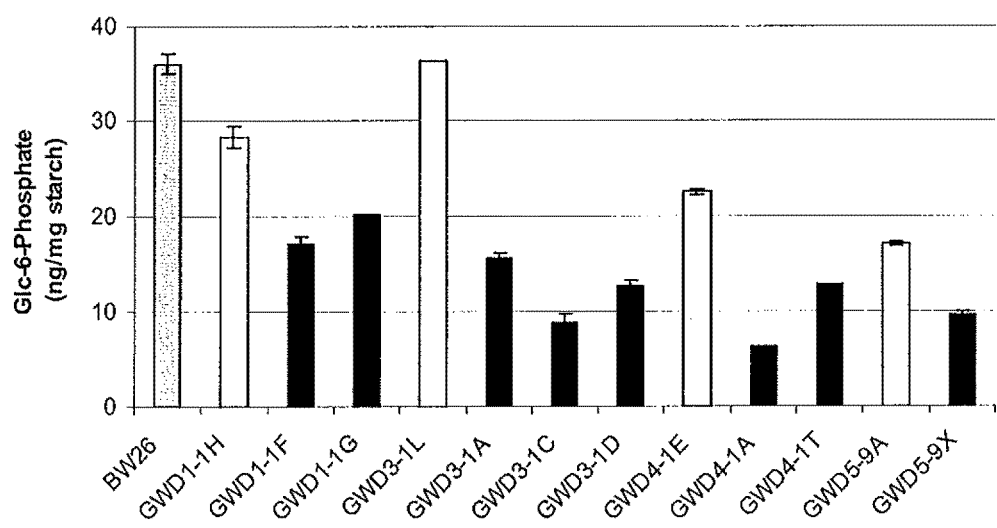
FIG. 1 is a graphical representation of Glucose-6-phosphate G6P content in grain starch of rsGWD transgenic wheat lines.

Table 1 provides a description of the SEQ ID NOs provided herein.

Table 2 provides an amino acid sub-classification.

Table 3 provides exemplary amino acid substitutions.

Table 4 provides the pasting values for rsGWD transgenic wheat.

Table 5 provides the results of growth analyses (seed weight, seed production) for rsGWD transgenic wheat.

Table 6 provides the results of growth analyses (leaf area, fillers, heads) for rsGWD transgenic wheat.

Table 7 provides the exon/intron structure of wheat compared to rice GWD.

DETAILED DESCRIPTION OF THE PREFERRED EMBODIMENTS

Throughout this specification and the claims which follow, unless the context requires otherwise, the word "comprise", and variations such as "comprises" and "comprising", will be understood to denote the inclusion of a stated integer or step or group of integers or steps but not the exclusion of any other integer or step or group of integers or steps. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Each embodiment in this specification is to be applied mutatis mutandis to every other embodiment unless expressly stated otherwise.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO: 2), etc. A summary of sequence identifiers is provided in Table 1 after the Examples. A sequence listing is provided after the claims.

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" is used herein to refer to a quantity, level, value, dimension, length, position, size, or amount that varies by as much as 30%, preferably by as much as 20% and more preferably by as much as 10% to the length of a reference quantity, level, value, dimension, length, position, size, or amount stage.

Starch

The present invention is based on the observation that modifying expression of a gene involved in starch phosphorylation and starch degradation in plants, in particular in the leaves, was associated with surprising effects in production parameters of the plant such as grain yield. This was surprising since previous studies have shown that modifying starch synthesis or storage led to reductions in yield. It was not expected that reduction in transitory starch phosphorylation or degradation in the leaves, which is involved in mobilizing fixed carbon to other parts of the plant, would result in yield increases.

"Starch" is defined herein as polysaccharide made up essentially of α-glucopyranose units. Starch is the major storage carbohydrate in plants such as, for example, cereals including wheat. Starch is synthesized in the amyloplasts and formed and stored in granules in the developing storage organ such as grain; it is referred to herein as "storage starch". It includes amylose, an essentially linear (<0.1% branchpoints) α-1,4-D-glucopyranose polymer, and amylopectin, which has short chains of α-D-glucopyranose units primarily linked by α-1,4 bonds with α-1,6 linked branches. Cereal starch from wild-type plants comprises up to about 20%-30% of amylose and about 70%-80% of amylopectin. A further significant difference between amylose and amylopectin is in the molecular weight of the polymers. Amylose has a helical conformation with a molecular weight of $10^4$-$10^6$ daltons while amylopectin has a molecular weight of about $10^7$ to $10^8$ daltons. Recent studies have shown that up to about 0.1% of α-1,6-glycosidic branching sites may occur in amylose, therefore it is described as "essentially linear". "Amylose" is defined herein as including essentially linear molecules of α-1,4 linked glucosidic (glucopyranose) units and amylose-like long-chain amylopectin (sometimes referred to as "intermediate material" or "amylose-like amylopectin", Takeda et al., 1993b; Fergason, 1994). The proportion of amylose in the starch as defined herein is on a weight/weight (w/w) basis, i.e. the weight of amylose as a percentage of the weight of total starch from the grain. Amylose content may be determined by any of the methods known in the art including size exclusion HPLC, for example in 90% (w/v) DMSO, concanavalin A methods (Megazyme Int, Ireland), or preferably by iodometric methods, for example as described in Example 1. The HPLC method may involve debranching of the starch (Batey and Curtin, 1996) or not involve debranching.

Starch is initially synthesized and accumulated in the leaves and other green tissues of a plant as a product of photosynthesis. This starch is referred, to herein as "transitory starch" or the like because, in contrast to seed or tuber starch, it accumulates in the plastids of the photosynthetic tissues during the day and is degraded at least during the night. Therefore, both synthetic and degradative enzymes are present in the cell at the same time, and the system is subject to diurnal regulation. At night, transitory starch is hydrolysed to sugars which are transported, primarily as sucrose, from the source tissues to sink tissues for use in growth of the plant, as an energy source for metabolism or for storage in tissues as storage starch. Transitory starch breakdown in leaves has been reviewed recently by Zeeman et al., 2004. The breakdown occurs by function of enzymes such as amylases, debranching enzymes, α-glucan phosphorylases and glucanotransferases.

Almost all plant starches are phosphorylated to some extent at C3 and C6 hydroxyl groups of amylopectin, but the extent of the phosphorylation varies considerably depending on the plant species. Potato tuber starch typically has 25 nmoles of glucose-6-phosphate per mg starch, with a range of 0.2-0.4% (w/w). Most of the phosphate groups in potato starch are linked to amylopectin, very little to amylose. In contrast to potato starch, cereal grain starch contains only 0.02-0.04% phosphate. As used herein, "phosphorylated starch" refers to starch which has phosphate groups bound as monoesters at C-3 and/or C-6 positions of glucose units. The level of phosphate groups in starch samples may be readily measured by methods known in the art, preferably by the Malachite Green method as described in Example 1, and is conveniently expressed as mmoles per mg of starch. The level of glucosyl-6-phosphate residues in starch samples may be readily measured by an amyloglucosidase assay as described in Example 1.

Starch Degradation

The initial step of starch degradation in both leaves and germinating seeds involves the enzyme endoamylase (α-amylase, EC 3.2.1.1), which in the germinating seed is secreted from the aleurone layer but in leaves is present in the chloroplasts. This enzyme attacks the starch at specific sites on the starch granule, causing pitting of the granule surface. Further attack on the starch molecules occurs by α-glucan phosphorylase (EC2.4.1.1) which produces glucose-1-phosphate from the non-reducing end of α-1,4 glucan chains, and debranching enzymes such as isoamylase (EC3.2.1.68) and pullulanase (EC3.2.2.142) which remove the α-1,6 branch points. Other enzymes involved are the exo-amylase β-amylase (EC3.2.1.2) which releases maltose from the non-reducing end of glucan chains, disproportionating enzyme (D-enzyme, EC2.4.1.25) and α-glucosidase (maltase, EC3.2.1.20) or maltose phosphorylase (EC2.4.1.8) which can act on the linear chains. In *Arabidopsis* and other dicots, β-amylase activity exceeds the other glucan-metabolising enzymes by about an order of magnitude and appears to be present both inside and outside the chloroplasts.

Glucan, water dikinase (GWD, EC2.7.9.4) appears to regulate the extent to which other enzymes attack the starch granules. GWD transfers the β-phosphate of ATP to either the C6 or C3 positions of glycosyl units in amylopectin, and the presence of such phosphates may be a signal for degradation to proceed. It is thought that the presence of the phosphate groups may change electrostatic interactions between the glucan chains, or with interacting proteins, to allow initiation of the process. GWD becomes bound to leaf starch granules during starch breakdown (Ritte et al, 2000) and may be more active during this time. GWD activity itself appears to be regulated at least in some plants in a circadian pattern through the day/night cycles.

Antisense experiments to reduce expression of GWD (also called R1 protein or OK1) in potatoes reduced starch bound phosphate by up to 90% (Viksø-Nielsen et al., 2001). A mutation in a homologous gene in *Arabidopsis thaliana* (called sex1 for starch excess phenotype) was associated with suppression of starch phosphate content and confirmed the involvement of GWD in starch phosphorylation (Zeeman and Rees, 1999). In addition, both the *Arabidopsis* mutant and potato suppressed lines displayed a "starch excess" phenotype where starch accumulated beyond normal levels in leaves, confirming the role of GWD in transitory starch degradation. No modification of the starch structure in these plants was observed in those studies. The reduced starch phosphate content in the potato tubers was accompanied by a reduction in "cold sweetening" of the potato tubers (Lorberth et al., 1998) which suggested a reduction in amylase or other hydrolase activity. The *Arabidopsis* sex1 mutants affected in their transitory starch metabolism also had altered carbohydrate metabolism, grow slowly and flowered late (Yu et al., 2001).

In 2005, Baunsgaard et al. defined a new class of water dikinase, the Phospho-glucose water dikinase (PWD). This enzyme, similar to but distinct from GWD, was active in further phosphorylating pre-phosphorylated starch (Kotting et al., 2005). Ritte et al. suggested that the phosphorylations in positions C3 or C6 of glucosyl residues in starch were catalyzed by PWD and GWD, respectively (Ritte G. et al., 2006).

Starch degradation and phosphorylation in germinating cereal seeds is partially understood but this is a highly specialized system involving tissue deterioration and induction of hydrolytic enzyme.

In some embodiments, the present invention provides for improvements in plant productivity or utilization by modification of starch phosphorylation and for degradation in plants, and is based on the observations of an association between the two. The modification of starch phosphorylation and/or degradation may be in transitory starch, for example in the leaves of the plant, in the storage starch, for example in the grain, or in both. The modification of a plant, preferably a cereal plant, according to the invention includes without limitation one or more alterations in the activity or amount of starch phosphorylation and/or degradation (breakdown) enzymes in the leaves and/or endosperm.

As used herein, "modifying" means a change in the material or its function, which may be an increase or decrease in amount, activity, rate of production, rate of inactivation, rate of breakdown, delay of onset, earlier onset, addition or removal of material, mutation, or any combination of these, so long as there is a change in function as a consequence. As used herein, "modulation of functional level" or similar term means either an increase or decrease in the functional level of a gene or protein of interest. "Functional level" should be understood to refer to the level of active protein, in casu the level of protein capable of performing the starch phosphorylation or starch degradation. The functional level is a combination of the actual level of protein present in the host cell and the specific activity of the protein. Accordingly, the functional level may e.g. be modified by increasing or decreasing the actual protein concentration in the host cell, which may readily be achieved by altering expression of a gene encoding the protein. The functional level may also be modified by modulating the specific activity of the protein. Such increase or decrease of the specific activity may be achieved by expressing a variant protein with higher or lower specific activity or by replacing the endogenous gene encoding the relevant protein with an allele encoding such a variant. Increase or decrease of the specific activity may also be achieved by expression of an effector molecule. In certain embodiments, the expression level of an appropriate coding sequence or activity or amount of an enzyme is chosen such that it is at least about 10%, at least 20%, at least 30%, at least 40%; at least 50%, at least 60%, at least 80% or even at least about 100%, at least 200%, at least 500%, or at least 1000% higher, or at least about 10%, at least 20%, at least 30%, at least 40%, at least 50%, at least 60%, at least 70%, at least 80%, at least 90%, at least 92%, at least 94%, at least 96%, at least 97%, at least 98% or at least 99% lower than a reference expression level, or reduced to an undetectable level.

As used herein, the terms "modifying", "altering", "increasing", "increased", "reducing", "reduced", "inhibited", "mutant" or the like are considered relative terms, i.e. in comparison with the wild-type or unaltered state. A wild-type plant is also referred to herein as a "control plant" and the terms are interchangeable. The "level of a protein" refers to the amount of a particular protein, for example GWD, which may be measured by any means known in the art such as, for example, Western blot analysis or other immunological means. The "level of an enzyme activity" refers to the amount of a particular enzyme measured in an enzyme assay. It would be appreciated that the level of activity of an enzyme might be altered in a mutant if a more or less active protein is produced, but not the expression level (amount) of the protein itself. Conversely, the amount of protein might be altered but the activity (per unit protein) remain the same. Reductions in both amount and activity are also possible such as, for example, when the expression of a gene encoding the enzyme is reduced transcriptionally or post-transcriptionally. In certain embodiments, the reduction in the level of protein or activity such as, for example, GWD, is by at least 40% or by at least 60% compared to the level of protein or activity in the leaf or the endosperm of unmodified cereal, for example wheat, or by at least 75%, at least 90% or at least 95%. The reduction in the level of the protein or enzyme activity or gene expression may occur at any stage in the development of the leaf, seed or grain, particularly during the daytime when photosynthesis is occurring, or during the grain filling stage while starch is being synthesized in the developing endosperm, or at all stages of grain development through to maturity. The term "wild-type" as used herein has its normal meaning in the field of genetics and includes plant, preferably cereal, cultivars or genotypes which are not modified as taught herein. Preferred "wild-type" varieties which are readily available to the public are: for breadwheat, cv. Bob White; for maize (*Zea mays*), Roundup Ready Corn 2; for rice; Nipponbare; for sorghum (*Sorghum bicolor*), cv. Sumac.

In one embodiment, the alteration comprises a reduction in the amount and/or activity of GWD in the plant leaves or endosperm, which was observed to result in a decreased phosphate content in the starch of the leaves and/or mature seed, for example cereal grain. In another embodiment, the modification comprises reduction in PWD as well as GWD activity. In a further embodiment, the modification comprises reduction in GWD and increase in amylase activity in the cereal grain, preferably α-amylase. Other starch degradative enzymes that may be altered in combination with any of the above include β-amylase, phosphorylase or starch debranching enzymes such as isoamylase or pullulanase. The alterations may be, for example, increased activity, decreased activity, altered localization or timing of activity. When alterations in some of these enzymes are combined, characteristics of the starch other than the phosphate content may also be altered. In an embodiment, the modified plant, preferably cereal plant, comprises alterations in the activity of multiple starch degradative enzymes in endosperm, preferably including a reduction in the activity of GWD such that the phosphate content in the starch of the grain is decreased. In a further embodiment, the activity of one or more starch degradative enzymes is altered in the plant in tissues other than endosperm or leaves, for example the activity of GWD may be increased in endosperm to compensate for some loss of activity caused by a transgene encoding an GWD-inhibitory molecule intended primarily for expression in the leaves, or the activity of amylase, preferably α-amylase, may be reduced in endosperm. The alteration in an enzyme activity may be an increase or reduction in amount or an alteration in the timing of expression. Starch synthesis may be further improved by the overexpression of one or more starch biosynthetic enzymes in combination with a reduction in GWD. Genes encoding such enzymes may be from any of a variety of sources known in the art, for example from bacteria, cereals or other sources, and may be modified to alter the catalytic properties, for example alteration of the temperature dependence of the enzymes (for example, see WO 94/09144).

The modified phenotype may be achieved by partial or full inhibition of the expression of a GWD gene, or the GWD and PWD genes. A "low starch phosphate content" phenotype or the like as used herein refers to total starch obtained from the plant or a plant part, for example leaf or grain, having a starch phosphate content of less than 0.02%, or alternatively reduced by at least 50% relative to a corresponding control starch. The extent to which the gene or genes are inhibited will in some degree determine the characteristics of the starch made in the wheat grain. Any of a range of gel electrophoresis techniques carried out on the proteins extracted from the modified wheat endosperm will reveal the nature and extent of modification to the GWD and/or PWD activity. Modification may occur as a reduction in GWD activity, complete abolition of enzyme activity, or an alteration in the distribution of the GWD or other enzymes within the leaf or endosperm. For example, GWD or other activity may be reduced by affecting the distribution of the enzymes within the endosperm, such as reducing the level of enzyme that is starch granule-bound. To carry out these tests, starch may be extracted from the wheat endosperm and the proteins therein analyzed, for example as outlined in Rahman et al., 1995. Techniques well known in the art such as SDS-PAGE and immunoblotting are carried out on the soluble and the starch granule fractions and the results used to identify the plants or grain where modifications have occurred to the GWD or other enzymes.

Alteration of the starch phosphorylation or degradation enzyme activities may be achieved by the introduction of one or more genetic variations into the cereal, preferably wheat, plant. That is, the genetic variations lead, directly or indirectly, to the alteration in enzyme activity in the plant part during growth or development and consequently to the starch modifications described herein. The genetic variation may be a heterologous polynucleotide which is introduced into the plant or a progenitor cell, for example by transformation or mutagenesis. The genetic variation may subsequently be introduced into different genetic backgrounds by crossing, as known in the art of plant breeding.

The amount or the activity of enzymes such as GWD or amylases in tissues or plant parts may be measured using any method known in the art such as, for example, by enzymatic assay, immunodetection methods, Western blotting or ELISA assays, or the level of its corresponding mRNA may measured by methods such as Northern blot hybridization analysis or reverse transcription polymerase chain reaction (RT-PCR). The level of starch phosphorylation may also be measured to indicate enzyme levels during synthesis of the starch. A cereal plant or grain having an altered level of a particular protein or enzyme activity in its endosperm may be screened or selected based on a reduced level of the protein or enzyme (direct assay), or it may be based on the phenotype of the grain of the wheat plant such as an increased or decreased level of phosphate, or a visual phenotype of the plant or plant part, for example shrunken grain or altered starch granule properties or altered plant morphology. The wheat plant with the altered starch properties as used herein may be identified using any of the methods known in the art, either directly determining the starch properties or indirectly, for example, detecting the presence of a genetic variation in the plant or its grain. The plant may be a plant in a population of wheat plants, such as, for example, in wheat breeding.

Production Potential

The invention provides plants with increased production characteristics. Exemplary enhanced production properties include, but are not limited to, traits that are beneficial to the grower such growth, yield, biomass and vigour as well as related properties such as, stress, drought, pest or disease resistance or improved aesthetic qualities such as flower or leaf characteristics, traits that are beneficial to the consumer of the horticultural produce harvested from the plant such as improved nutritive or taste content in human food or drink or animal feed, or beneficial to the food or industrial processor such as improved processing traits. In such uses, the plants are generally grown for the use of their grain, fruit and other plant parts, including leaves, stalks, husks, vegetative parts, and the like in human or animal foods or drinks including use as part of animal silage or for ornamental purposes. In an embodiment, the plant material of the invention has improved use as silage for animal feed such as, for example, as described in US Patent Application Publication No US2006/0150278, herein incorporated by reference. In this embodiment, it is preferred that the heterologous polynucleotide is expressed from a transcriptional control sequence that is expressed preferentially in the vegetative parts of the plant, preferably the leaves or stems, and even more preferably that the heterologous polynucleotide is expressed at low levels or not detectably in the seed of the plant.

The increased production potential may be measured by any method known in the art, according to the parameter of interest.

As described in the Examples, plants having reduced starch phosphorylation as a result of down regulating the production of GWD also showed enhanced levels of α-amylase. Thus, in some embodiments, the specification provides a method of producing a genetically modified plant which has a reduced level of starch phosphorylation and increased endogenous glycosylases compared to a control plant, the method comprising selecting from a plurality of plants which comprise in their genome a heterologous polynucleotide operably connected to a transcriptional control sequence and that encodes an agent that down regulates endogenous starch phosphorylation, a plant that down regulates the activity of starch phosphorylation and wherein the level of endogenous glycosylase is increased relative to the control plant. Alternatively, the heterologous polynucleotide may be a mutated gene, for example comprising an induced mutation, the corresponding wild-type gene encoding an enzyme or regulatory protein involved in starch phosphorylation, where the result of the mutation is reduced starch phosphorylation. As used herein, a "plurality of plants" refers to at least two plants, preferably at least 10 plants, and even more preferably at least 50, 100 or 200 plants. Typically, the plurality of plants each contain a transgene or induced mutation but do not all show the same extent of modification, showing a range in the extent of the effect. Therefore, the methods of the invention may include a selection or identification step, in which a plant having optimal levels of modification is identified and chosen.

In some embodiments, starch degradation or the level or functional activity of an enzyme involved in starch degradation, or starch phosphorylation is down regulated to a level less than about 80%, 70%, 60%, 50%, 40%, 30%, 20% or 15%, and suitably less than about 10%, 9%, 8%, 7%, 6%, 5%, 4%, 3%, 2% or 1% relative to a corresponding control plant to achieve an increase in production potential. In an embodiment, the reduction in starch degradation or the level or functional activity of an enzyme involved in starch degradation, or starch phosphorylation is down regulated in photosynthetic tissue such as, for example, leaves, to achieve an increase in production potential, or alternatively in a storage organ for starch, preferably a seed. Preferably, in this embodiment, this reduction results in a substantial enhancement of a production potential which is generally at least about 20%, 25% or 30% but especially at least about 40%, 45%, 50% or 55% and more especially at least about 60%, 65%, 70%, 75%, 80%, 85%, 90%, 95% or greater increase in production potential relative to a corresponding control plant grown under the same environmental conditions. The amount of reduced starch degradation or reduced starch phosphorylation required may depend upon other factors such as the plant species or strain and the level, location or timing of starch degradation or starch phosphorylation enzyme activity and/or the level or activity of their substrates and/or ancillary molecules or co-factors in the starch degradative pathway. However, it is considered that any optimisation, which may be required in such an event is achievable using routine methods including those described herein.

Reduced starch degradation may be accomplished in tissues throughout the plant, for example using a constitutive promoter to drive expression of a heterologous polynucleotide that down regulates starch degradation. Alternatively, it may be accomplished in source tissues (leaves), in transport tissues or in sink tissues (endosperm) using a tissue-specific or developmentally regulated promoter. "Sink cell" and "sink tissue" as used herein, refer to cells, tissues or organs which comprise a net inflow of organic carbon that has entered the cells in a form other than fixation of carbon dioxide ie. as sugars or other carbohydrates. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

In another embodiment, the level of endogenous starch phosphorylation is modulated by using starch phosphorylation enzymes of different functional activities. This may arise from differences in the specific activities or stabilities of the enzymes in the cellular compartment where the starch degradation is accomplished. In certain embodiments, the activity of a starch-degrading enzyme that is used for the degradation of endogenous starch is increased at least about 10%, 20%, 30%, 40%, 50%, 60%, 70%, 80% or 90%, or even at least about 100%, 200%, 300%, 400%, 500%, 600%, 700%, 800%, 900% or 1000% higher, or reduced by at least about 10%, 20%, 30% 40%, 50%, 60%, 70%, 80%, 90%, 92%, 94%, 96%, 97%, 98% or 99%, or even at least about 99.5%, or 99.9% relative to the level of a reference enzyme in a control plant. Starch degrading enzymes of different activities may be naturally occurring or may be obtained by synthetic or recombinant means, for example, by modification of the catalytic site or any other site (e.g., substrate-binding site, co-factor binding site) of a reference or parent enzyme. Typically, the modification is achieved by the substitution, addition or deletion of at least one amino acid in the sequence of parent enzyme using for example rational or established methods of mutagenesis or combinatorial chemistries, as are known in the art. Variant starch degradation enzymes may comprise conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in a parent enzyme is suitably replaced with another amino acid residue from the same side chain family. Alternatively, in another embodiment, mutations can be introduced randomly along all or part of a polynucleotide that codes for the reference enzyme, such as by saturation mutagenesis, and the resultant mutants can be screened for enzyme activity to identify mutants with a different activity than the parent enzyme.

In other embodiments, the level of and location of degradation of endogenous starch is modulated by using a starch degrading enzyme directed into different functional subcellular compartments. In illustrative examples, the activity is modified in the leaf and/or seed. This may be achieved by expression of a nuclear gene, resulting in the synthesis within the cytosol of a form of the enzyme with no signal sequences for transport to other cellular compartments. In other illustrative examples, the activity is directed to a storage compartment such as a amyloplast or vacuole, or to a storage and transport compartment such as the extracellular (apoplasmic) space, by including within the sequence of the enzyme a signal for transport of the enzyme from the cytosol to the desired cellular compartment. Certain signal sequences can result in the distribution of enzyme activity between two or more cellular compartments.

These methods include analysis of plants or plantlets by methods such as electrophoresis, chromatography (including paper chromatography, thin layer chromatography, gas chromatography, gas-liquid chromatography and high-performance liquid chromatography) techniques. Separated components are typically identified by comparison of separation profiles with standards of known identity, or by analytical techniques such as mass spectrometry and nuclear magnetic resonance spectroscopy. For example, reference may be made to Example 9, Robinson, *The Organic Constituents of Higher Plants*, Cordus Press, North Amherst, USA, 1980; Adams et al., Anal. Biochem., 266:77-84, 1999; Veronese et al., Enz. Microbial Tech., 24:263-269, 1999; Hendrix et al., J. Insect Physiol., 47:423-432, 2001; Thompson et al., Carbohydrate Res., 331:149-161, 2001; and references cited therein. Carbohydrates can be assayed using standard protocols known to persons skilled in the art.

Genes

The present invention involves modification of gene activity and the construction and use of chimeric genes. As used herein, the term "gene" includes any deoxyribonucleotide sequence which includes a protein coding region of a structural gene or which is transcribed in a cell but not translated, as well as associated non-coding and regulatory regions. Such associated regions are typically located adjacent to the coding region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The "wheat GWD gene" or the like as used herein refers to a nucleotide sequence encoding GWD in wheat, which can readily be distinguished from PWD or other proteins by those skilled in the art. Wheat GWD genes include the naturally occurring variants existing in wheat, including those encoded by the A, B and D genomes of breadwheat, as well as non-naturally occurring variants which may be produced by those skilled in the art of gene modification. In a preferred embodiment, a wheat GWD gene refers to a nucleic acid molecule, which may be present in or isolated from wheat or derived therefrom, comprising nucleotides having a sequence having at least 80% identity to the coding region of the GWD gene shown in SEQ ID NO: 2.

In analogous fashion, the "wheat PWD gene" or the like as used herein refers to a nucleotide sequence encoding PWD in wheat, which can readily be distinguished from other di-kinases or other proteins by those skilled in the art. This includes the naturally occurring variants of the genes existing in wheat, including those encoded by the A, B and D genomes of breadwheat, as well as non-naturally occurring variants which may be produced by those skilled in the art of gene modification.

A genomic form or clone of a gene containing the coding region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes found in nature that are inserted into a non-native organism, native genes introduced into a new location within the native host, or chimeric genes. A "transgene" is a gene that has been introduced into the genome by a transformation procedure. The term "genetically modified" includes introducing genes into cells, mutating genes in cells and altering or modulating the regulation of a gene in a cell or organisms to which these acts have been done or their progeny.

Polynucleotides

The present invention refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein. Nucleotides of the polymer may be modified according to methods known in the art, for example, analogs of phosphodiester linkages include: phosphorothioate, phosphorodithioate, phosphoroselenoate, phosphorodiselenoate, phosphoroanilothioate, phosphoranilidate, phosphoramidate, but the polynucleotides are preferably unmodified or modified only as occurs in a cell. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing along part of their lengths, or along the full length of one or both. The term "polynucleotide" is used interchangeably herein with the term "nucleic acid".

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention refers to use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Polynucleotides used as a probe are typically conjugated with a detectable label such as a radioisotope, an enzyme, biotin, a fluorescent molecule or a chemiluminescent molecule. Oligonucleotides of the invention are useful in methods of detecting an allele of a GWD or other gene linked to a trait of interest, for example modified starch. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridizing, for example, to the wheat genome close to that of, the specific oligonucleotide molecules defined herein. For example, variants may comprise additional nucleotides (such as 1, 2, 3, 4, or more), or less nucleotides as long as they still hybridize to the target region. Furthermore, a few nucleotides may be substituted without influencing the ability of the oligonucleotide to hybridize the target region. In addition, variants may readily be designed which hybridize close (for example, but not limited to, within 50 nucleotides) to the region of the plant genome where the specific oligonucleotides defined herein hybridize.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridizing agents. The terms "polynucleotide variant" and "variant" also include naturally occurring allelic variants.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, 500 or 600 nucleotides in each case. Reference also may be made to the BLAST family of programs as for example disclosed by Altschul et al., Nucl. Acids Res. 25:3389, 1997. A detailed discussion of sequence analysis can be found in Unit 19.3 of Ausubel et al., "*Current Protocols in Molecular Biology*", John Wiley & Sons Inc, 1994-1998, Chapter 15.

Nucleotide or amino acid sequences are indicated as "essentially similar" when such sequences have a sequence identity of at least about 75%, particularly at least about 80%, more particularly at least about 85%, quite particularly about 90%, especially about 95%, more especially about 100%, quite especially are identical. It is clear than when RNA sequences are described as essentially similar to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, a polynucleotide of the invention which encodes a polypeptide with GWD activity is greater than 400, more preferably greater than 500, more preferably greater than 600, more preferably greater than 700, more preferably greater than 800, more preferably greater than 900, and even more preferably greater than 1,000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization. The higher the stringency, the higher will be the degree of complementarity between a target nucleotide sequence and the labelled polynucleotide sequence. "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. As used herein, the term "hybridizes under low stringency, medium stringency, high stringency, or very high stringency conditions" describes conditions for hybridization and washing. Specific hybridization conditions referred to herein are as follows: 1) low stringency hybridization conditions in 6× sodium chloride/sodium citrate (SSC) at about 45° C., followed by two washes in 0.2×SSC, 0.1% SDS at 50-55° C.; 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogous and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 60% free, more preferably at least 75% free, and more preferably at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

The % identity of a polypeptide relative to another polypeptide can be determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment is a portion of a polypeptide of the invention which maintains a defined activity of the full-length polypeptide. In a particularly preferred embodiment, the biologically active fragment is able to phosphorylate starch to produce C6 phosphorylated starch. Biologically active fragments can be any size as long as they maintain the defined activity, but are preferably at least 100 or 200 amino acid residues long.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes related to those of the present invention, such as GWD genes from plant species other than wheat or barley, and/or include different genes from the same plant encoding similar proteins (such as the wheat GWD genes). Products derived from mutated/altered DNA can readily be screened using techniques described herein to determine if they possess, for example, GWD activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 3 under the heading of "exemplary substitutions".

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention, or serve as a ligand for binding of another molecule.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" is used herein in its broadest sense and includes a region of a gene, generally upstream (5') of the RNA encoding region, which controls the initiation and level of transcription. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In one embodiment, a promoter is expressed in all photosynthetic tissue, which may correspond to all aerial parts of the plant, for example a promoter that is involved in expressing a gene required for photosynthesis such as rubisco small subunit promoters. The term may also refer to expression at specific developmental stages in an organ, such as in early or late embryogenesis or different stages of maturity; or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the cytosol, vacuole, or apoplastic space may be achieved by the inclusion in the structure of the gene product of appropriate signals for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter for high molecular weight (HMW) glutenin gene, Bx17. By "sink tissue-specific promoter" is meant a promoter that preferentially directs expression of an operably linked transcribable sequence in the sink tissue of a plant (e.g., endosperm, fruit tissues, root tissue, tuber tissue, seed tissue, culm tissue or sink leaf tissue) as compared to expression in other tissues of the plant, including source tissues (e.g., leaf).

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters; promoters from plants, such as ubiquitin promoters such as the Ubi promoter from the maize ubi-1 gene, Christensen et al., (1996) (see, e.g., U.S. Pat. No. 4,962,028) or actin promoters; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, (1983), Salomon et al., (1984), Garfinkel et al., (1983); Barker et al., (1983); including various promoters isolated from plants and viruses such as the cauliflower mosaic virus promoter (CaMV 35S, 19S). Many tissue specific promoter regions are known, such as the Rubisco small subunit promoter which preferentially is expressed in leaf tissue. Other transcriptional initiation regions which preferentially provide for transcription in certain tissues or under certain growth conditions, include those from napin, seed or leaf ACP, zein, and the like. Fruit specific promoters are also known, one such promoter is the E8 promoter, described by Deikman et al. (1988) and DellaPenna et al. (1989). Non-limiting methods for assessing promoter activity are disclosed by Medberry et al. (1992, 1993), Sambrook et al. 1989, and McPherson et al. (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. In this latter embodiment, the transcriptional control element is suitably a developmentally regulated promoter to control the timing of expression. The promoter selection may allow for specific expression of an introduced polynucleotide timed to take advantage of fluctuating starch levels. The promoters sequences may include cis-acting sequences which regulate transcription, where the regulation involves, for example, chemical or physical repression or induction (e.g., regulation based on metabolites, light, or other physicochemical factors) or regulation based on cell differentiation (such as associated with leaves, roots, seed, or the like in plants; see, e.g., U.S. Pat. No. 5,459,252 disclosing a root-specific promoter). Thus, the promoter region, or the regulatory portion of such region, is obtained from an appropriate gene that is so regulated. For example, the 1,5-ribulose biphosphate carboxylase gene is light-induced and may be used for transcriptional initiation. Other genes are known which are induced by stress, temperature, wounding, pathogen effects, etc.

Other cis-acting sequences which may be employed include transcriptional and/or translational enhancers. Enhancer regions are well known to persons skilled in the art, and can include an ATG translational initiation codon and adjacent sequences. The initiation codon must be in phase with the reading frame of the coding sequence relating to the foreign or exogenous polynucleotide to ensure translation of the entire sequence. The translation control signals and initiation codons can be of a variety of origins, both natural and synthetic. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

Examples of transcriptional enhancers include, but are not restricted to, elements from the CaMV 35S promoter and octopine synthase genes as for example described by Last et al. (U.S. Pat. No. 5,290,924, which is incorporated herein by reference).

The nucleic acid construct of the present invention typically comprises a 3' non-translated sequence from about 50 to 1,000 nucleotide base pairs which may include a transcription termination sequence. A 3' non-translated sequence may contain a transcription termination and/or polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. Examples of suitable 3' non-translated sequences are the 3' transcribed non-translated regions containing a polyadenylation signal from the nopaline synthase (nos) gene of *Agrobacterium tumefaciens* (Bevan et al., 1983) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the small subunit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An (Methods in Enzymology, 153:292, 1987), which is incorporated herein by reference.

As the DNA sequence inserted between the transcription initiation site and the start of the coding sequence, i.e., the untranslated 5' leader sequence (5'UTR), can influence gene expression, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide.

Vectors

The present invention makes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants. Examples of such resistance genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can select based on resistance to a selective agent (e.g., a herbicide, antibiotic, radiation, heat, or other treatment damaging to untransformed cells). A screenable marker gene (or reporter gene) confers a trait that one can identify through observation or testing, i.e., by screening (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (npt) gene conferring resistance to kanamycin, paromomycin, G418 and the like as, for example, described by Potrykus et al. (Mol. Gen. Genet., 199:183, 1985); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces* viridochromogenes conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (Biotech., 6:915, 1988), a bar gene conferring resistance against bialaphos as, for example, described in WO91/02071; a nitrilase gene such as bxn from *Klebsiella ozaenae* which confers resistance to bromoxynil (Stalker et al., Science, 242:419, 1988); a dihydrofolate reductase (DHFR) gene conferring resistance to methotrexate (Thillet et al., J. Biol. Chem., 263:12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995); a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

In some embodiments, the level of endogenous starch phosphorylation and/or degradation is modulated by increasing the level of expression of a nucleotide sequence that codes for a polypeptide for these activities in a plant cell, or decreasing the level of expression of genes encoding proteins involved in these activities in the plant. By way of example, this can be achieved at the level of transcription by using promoters of different strengths or inducible promoters, which are capable of controlling the level of transcript expressed from the coding sequence. In some embodiments, heterologous sequences are introduced which encode transcription factors that modulate or enhance expression of genes whose products down regulate starch phosphorylation. The level of expression of the gene may be modulated by altering the copy number per cell of a construct comprising the coding sequence and a transcriptional control element that is operably connected thereto and that is functional in the cell. Alternatively, a plurality of transformants may be selected, and screened for those with a favourable level and/or specificity of transgene expression arising from influences of endogenous sequences in the vicinity of the transgene integration site. A favourable level and pattern of transgene expression is one which results in a substantial increase in plant production potential such as yield or biomass or a significant decrease in starch degradation in cells of a plant. This may be detected by simple testing of transformants at different developmental stages.

Reducing gene expression may be achieved through introduction and transcription of a "gene-silencing chimeric gene" introduced into the host cell. The gene-silencing chimeric gene may be introduced stably into the host cell's genome, preferably nuclear genome, or it may be introduced transiently, for example on a viral vector. As used herein "gene-silencing effect" refers to the reduction of expression of a target nucleic acid in a host cell, preferably a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing should not necessarily be interpreted as an abolishing of the expression of the target nucleic acid or gene. It is sufficient that the level expression of the target nucleic acid in the presence of the silencing RNA is lower that in the absence thereof. The level of expression may be reduced by at least about 10% or at least about 15% or at least about 20% or at least about 25% or at least about 30% or at least about 35% or at least about 40% or at least about 45% or at least about 50% or at least about 55% or at least about 60% or at least about 65% or at least about 70% or at least about 75% or at least about 80% or at least about 85% or at least about 90% or at least about 95% or at least about 100%. Target nucleic acids may include endogenous genes, transgenes or viral genes or genes introduced by viral vectors. Target nucleic acid may further include genes which are stably introduced in the host's cell genome, preferably the host cell's nuclear genome.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Bourque, 1995 lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 states that antisense methods are now a very well established technique for manipulating gene expression.

As used herein, the term "an antisense polynucleotide which hybridizes under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell.

Ribozymes

The term "ribozyme" refers to an RNA molecule which specifically recognizes a distinct substrate RNA and catalyzes its cleavage. Typically, the ribozyme contains an antisense sequence for specific recognition of a target nucleic acid, and an enzymatic region referred to herein as the "catalytic domain". The types of ribozymes that are particularly useful in this invention are the hammerhead ribozyme (Haseloff and Gerlach, 1988, Perriman et al., 1992) and the hairpin ribozyme (Shippy et al., 1999). DNA encoding the ribozymes can be chemically synthesized using methods well known in the art. Accordingly, also provided by this invention is a nucleic acid molecule coding for a ribozyme of the invention. Typically, the DNA encoding the ribozyme can be inserted into an expression cassette or transcription cassette. Specific ribozyme cleavage sites within any potential RNA target are identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. When employed, ribozymes may be selected from the group consisting of hammerhead ribozymes, axehead ribozymes, newt satellite ribozymes, Tetrahymena ribozymes and RNAse P, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should also be capable of hybridizing a target nucleic acid molecule (for example an mRNA encoding a polypeptide provided as SEQ ID NO: 2, SEQ ID NO: 5) under "physiological conditions", namely those conditions within a cell, especially conditions in a plant cell such as a wheat or barley cell.

RNA Interference/Duplex RNA

As used herein, "artificially introduced dsRNA molecule" refers to the direct introduction of dsRNA molecule, which may e.g. occur endogenously by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al. (1998) have provided a model for the mechanism by which dsRNA can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with the unrelated sequence forming a loop structure, so the hairpin RNA comprises a stem-loop structure. The design and production of suitable dsRNA molecules for the present invention is well within the capacity of a person skilled in the art, particularly considering Waterhouse et al., 1998; Smith et al., 2000; WO 99/32619; WO 99/53050; WO 99/49029; and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The dsRNA may be classified as long hpRNA, having long, sense and antisense regions which can be largely complementary, but need not be entirely complementary (typically larger than about 200 bp, ranging between 200-1000 bp). hpRNA can also be rather small with the double-stranded portion ranging in size from about 30 to about 42 bp, but not much longer than 94 bp (see WO04/073390, herein incorporated by reference). The presence of the double stranded RNA region is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridize should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Examples of dsRNA molecules that may be used to down-regulate the production of a polypeptide with GWD activity are provided in Examples 7 and 10.

Other silencing RNA may be "unpolyadenylated RNA" comprising at least 20 consecutive nucleotides having at least 95% sequence identity to the complement of a nucleotide sequence of an RNA transcript of the target gene, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having at least 95% sequence identity to the sequence of the target nucleic acid or the complement thereof, and further comprising a largely-double stranded region as described in WO03/076619. Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other. The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference).

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the random or site-directed integration, or stable maintenance in a replicable non-integrated form, of an introduced foreign or exogenous gene or sequence. By "transgene" is meant a foreign or exogenous gene or sequence that is introduced into a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, a seed, or a plant piece such as, for example from an embryo, scutellum, protoplast, callus, or other tissue.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch (1997).

In principle, both dicotyledonous and monocotyledonous plants that are amenable to transformation, can be modified by introducing a nucleic acid construct according to the invention into a recipient cell and growing a new plant that harbors and expresses a polynucleotide according to the invention.

Introduction and expression of foreign or exogenous polynucleotides in dicotyledonous plants such as tobacco, potato and legumes such as, for example, alfalfa has been shown to be possible using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond (Biotechnology, 1:262, 1983) and Hoekema et al. (Nature, 303:179, 1983). Such a binary system is preferred inter alia because it does not require integration into the Ti plasmid in *Agrobacterium*.

Methods involving the use of *Agrobacterium* include, but are not limited to: (a) co-cultivation of *Agrobacterium* with cultured isolated protoplasts; (b) transformation of plant cells or tissues with *Agrobacterium*; (c) transformation of seeds, apices or meristems with *Agrobacterium*, or (d) inoculation in planta such as the floral-dip method as described by Bechtold et al. (1993). This approach is based on the vacuum infiltration of a suspension of *Agrobacterium* cells. Alternatively, the chimeric construct may be introduced using root-inducing (Ri) plasmids of *Agrobacterium* as vectors.

Methods for transformation of cereal plants such as wheat and barley or other monocots such as sugarcane for introducing genetic variation into the plant by introduction of an exogenous nucleic acid and for regeneration of plants from protoplasts or immature plant embryos are well known in the art, see for example, Wan and Lemaux (1994), Tingay et al., (1997), Canadian Patent Application No. 2,092,588, Australian Patent Application No 61781/94, Australian Patent No 667939, U.S. Pat. No. 6,100,447, International Patent Application PCT/US97/10621, U.S. Pat. No. 5,589,617, U.S. Pat. No. 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

The genetic construct can also be introduced into plant cells by electroporation as, for example, described by Fromm et al. (Proc. Natl. Acad. Sci., U.S.A, 82:5824, 1985) and Shimamoto et al. (Nature 338:274-276, 1989). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus.

Another method for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al. (Nature 327:70, 1987). Although typically only a single introduction of a new nucleic acid sequence is required, this method particularly provides for multiple introductions.

Alternatively, the nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

There are a variety of methods known currently for transformation of monocotyledonous plants. Presently, methods for transformation of monocots are microprojectile bombardment of explants or suspension cells, *Agrobacterium*-mediated gene transfer, and direct DNA uptake or electroporation as, for example, described by Shimamoto et al., 1989. Transgenic maize plants have been obtained by introducing the *Streptomyces hygroscopicus* bar gene into embryogenic cells of a maize suspension culture by microprojectile bombardment (Gordon-Kamm, 1990). Wheat plants have been regenerated from embryogenic suspension culture by selecting only the aged compact and nodular embryogenic callus tissues for the establishment of the embryogenic suspension cultures (Vasil, 1990). The combination with transformation systems for these crops enables the application of the present invention to monocots. Transgenic sugarcane plants have been regenerated from embryogenic callus as, for example, described by Bower et al. (1996).

Alternatively, a combination of different techniques may be employed to enhance the efficiency of the transformation process, e.g., bombardment with *Agrobacterium* coated microparticles (EP-A-486234) or microprojectile bombardment to induce wounding followed by co-cultivation with *Agrobacterium* (EP-A-486233).

Preferred plants for the present invention are species grown or harvested for their yield of valuable substances including starch, which are used for example as foods, feeds, fermentation or industrial feedstocks among other uses.

Mutagenesis

The plants of the invention can be produced and identified after mutagenesis. This may provide a plant which is non-transgenic, which is desirable in some markets.

Mutants can be either naturally occurring (that is to say, isolated from a natural source) or synthetic (for example, by performing site-directed mutagenesis on the nucleic acid) or induced. Generally, a progenitor plant cell, tissue, seed or plant may be subjected to mutagenesis to produce single or multiple mutations, such as nucleotide substitutions, deletions, additions and/or codon modification. In the context of this application, an "induced mutation" is an artificially induced genetic variation which may be the result of chemical, radiation or biologically-based mutagenesis, for example transposon or T-DNA insertion. Preferred mutations are null mutations such as nonsense mutations, frameshift mutations, insertional mutations or splice-site variants which completely inactivate the gene. Nucleotide insertional derivatives include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletional variants are characterised by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or most preferably only one nucleotide. Such a substitution may be "silent" in that the substitution does not change the amino acid defined by the codon. Alternatively, conservative substituents are designed to alter one amino acid for another similar acting amino acid. Typical conservative substitutions are those made in accordance with the table above "Exemplary substitutions".

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

In a preferred embodiment, the plant comprises a deletion of at least part of a GWD gene. As is understood in the art, hexaploid wheats such as bread wheat comprise three genomes which are commonly designated the A, B and D genomes, while tetrapolid wheats such as durum wheat comprise two genomes commonly designated the A and B genomes. Each genome comprises 7 pairs of chromosomes which may be observed by cytological methods during meiosis and thus identified, as is well known in the art.

Mutagenesis can be achieved by chemical or radiation means, for example EMS or sodium azide (Zwar and Chandler, 1995) treatment of seed, or gamma irradiation, well know in the art. Isolation of mutants may be achieved by screening mutagenised plants or seed. For example, a mutagenized population of wheat may be screened for low phosphate content in the leaf or grain starch, mutation of the GWD gene by a PCR or heteroduplex based assay, or loss of the GWD protein by ELISA. In a polyploid plant, screening is preferably done in a genotype that already lacks one or two of the GWD activities, for example in a wheat plant already mutant in the GWD genes on two of the three genomes, so that a mutant entirely lacking the functional activity is sought. Alternatively, the mutation may be identified using techniques such as "tilling" in a population mutagenised with an agent such as EMS (Slade et al, 2005). Such mutations may then be introduced into desirable genetic backgrounds by crossing the mutant with a plant of the desired genetic background and performing a suitable number of backcrosses to cross out the originally undesired parent background.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama, 1998. These DNA shuffling techniques may include genes related to those of the present invention, such as GWD genes from plant species other than wheat or barley, and/or include different genes from the same plant encoding similar proteins. Products derived from mutated/altered DNA can readily be screened using techniques described herein to determine if they possess, for example, GWD activity.

The mutation may have been introduced into the plant directly by mutagenesis or indirectly by crossing of two parental plants, one of which comprised the introduced mutation. The modified plants such as wheat plants may be transgenic or non-transgenic. Using mutagenesis, a non-transgenic plant lacking the function of interest may be produced. The invention also extends to the grain or other plant parts produced from the plants and any propagating material of the plants that can be used to produce the plants with the desired characteristics, such as cultured tissue or cells. The invention clearly extends to methods of producing or identifying such plants or the grain produced by such plants.

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cereal plant such as wheat. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes in wheat are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al., 2001; Langridge et al., 2001; Sharp et al., 2001).

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Any molecular biological technique known in the art which is capable of detecting alleles of an GWD or other gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) an GWD gene which confers altered starch phosphorylation and/or degradation. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., 2001.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells expressing an ABA 8'-hydroxylase gene. However, it will generally be easier if PCR is performed on genomic DNA isolated from a plant.

A primer is an oligonucleotide sequence that is capable of hybridizing in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. and Sambrook et al. Sequencing can be carried out by any suitable method, for example, dideoxy sequencing, chemical sequencing or variations thereof. Direct sequencing has the advantage of determining variation in any base pair of a particular sequence.

Plants

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a whole plant and which comprises starch. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are endosperm, scutellum, aleurone layer and embryo.

As used herein, the term "grain" generally refers to mature, harvested seed of a plant but can also refer to grain after imbibition or germination, according to the context. Mature cereal grain such as wheat commonly has a moisture content of less than about 18-20%.

A "transgenic plant" as used herein refers to a plant that contains a gene construct not found in a wild-type plant of the same species, variety or cultivar. That is, transgenic plants (transformed plants) contain genetic material that they did not contain prior to the transformation. A "transgene" as referred to herein has the normal meaning in the art of biotechnology and refers to a genetic sequence which has been produced or altered by recombinant DNA or RNA technology and which has been introduced into the plant cell. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of reduced phosphate content of the starch produced from the seed of the plant, or related phenotype such as increased production potential.

As used herein, "germination" refers to the emergence of the root tip from the seed coat after imbibition. "Germination rate" refers to the percentage of seeds in a population which have germinated over a period of time, for example 7 or 10 days, after imbibition. A population of seeds can be assessed daily over several days to determine the germination percentage over time.

With regard to seeds of the present invention, as used herein the term "germination rate which is substantially the same" means that the germination rate of the transgenic seeds is at least 90%, that of isogenic non-transgenic seeds. Germination rates can be calculated using techniques known in the art.

Plants provided by or contemplated for use in the practice of the present invention include angiosperms and gymnosperms, and within the angiosperms, both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit.

In some embodiments, the transgenic plant is a cereal plant. Examples of cereal plants include, but are not limited to, wheat, barley, rice, maize (corn), sorghum, oats, and rye. More preferably, the cereal plant is wheat, barley, maize or sorghum. Illustrative examples include wheat, rice and sorghum.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present invention may belong to, but is not limited to, any of the above-listed species. Also encompassed are plants that are produced by conventional techniques using *Triticum* sp. as a parent in a sexual cross with a non-Triticum species (such as rye [*Secale cereale*]), including but not limited to Triticale. Preferably, the wheat plant is suitable for commercial production of grain, such as commercial varieties of hexaploid wheat or durum wheat, having suitable agronomic characteristics which are known to those skilled in the art.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Food Production

The invention provides improved plants having enhanced production potential. In some embodiments this is useful in plants that are harvested for food.

Clearly, food plants include fruits, nuts or vegetables harvested for leaves, stems, fruit, tubers, seeds and pods.

In another aspect, the invention provides cereal plants and grain, preferably of wheat, that is useful for food or feed production, the grain having starch comprising a modified phosphate content and optionally a modified level of starch degradative enzymes. Preferably the plant from which the grain is obtained has a reduced level of GWD activity in the endosperm during development. The plant of the present invention is useful for food production and in particular for commercial food production. Such food production might include the making of flour, dough or other products that might be an ingredient in commercial food production. In an embodiment which is desirable for use in, food production, the seed or grain of the plant has a phosphate content that is essentially the same as, or increased, relative to the wild-type plant, and a level of activity of degradative enzymes, particularly of one or more amylases such as α-amylase or β-amylase, which is reduced by the presence of a transgene or an introduced mutation which reduces expression of a gene encoding such a degradative enzyme in the grain. Flour or dough from such grain has desirable properties for baking or other food production based on a modified viscosity of the starch and/or reduced amylase level. In an alternative embodiment which is desirable for animal feed or for industrial uses such as bioethanol production, the seed or grain of the plant has a phosphate content that is reduced relative to the wild-type plant, and a level of activity of degradative enzymes, particularly of one or more amylases such as α-amylase or β-amylase, which is increased in association with the reduced phosphate content, as exemplified herein. Such grain or starch products obtained therefrom have increased digestibility when used as feed or increased rate or efficiency of conversion when used for ethanol production.

The desired genetic background of the plant will include considerations of agronomic yield and other characteristics. Such characteristics might include whether it is desired to have a winter or spring types, agronomic performance, disease resistance and abiotic stress resistance. For Australian use, one might want to cross the altered starch trait of a wheat plant into wheat cultivars such as Baxter, Kennedy, Janz, Frame, Rosella, Cadoux, Diamondbird or other commonly grown varieties. Other varieties will be suited for other growing regions. It is preferred that the plant, preferably wheat, variety of the invention provide a yield not less than 105% of the corresponding wild-type variety in at least some growing regions, more preferably not less than 110% and even more preferably not less than 115%. The yield can readily be measured in controlled field trials.

In further embodiments, the starch content of the grain is at least about 25%, 35%, 45%, or 55% to 65% (w/w) and preferably is increased relative to the wild-type. Wild-type wheat grown commercially has a starch content usually in the range 55-65%, depending somewhat on the cultivar grown. Alternatively, the seed or grain of the invention has a starch content of at least 90% relative to that of grain from a wild-type plant, and preferably at least 95%, 100%, 102% or 105%. Other desirable characteristics include the capacity to mill the grain, in particular the grain hardness. Another aspect that might make a wheat plant of higher value is the degree of starch extraction from the grain, the higher extraction rates being more useful. Grain shape is also another feature that can impact on the commercial usefulness of a plant, thus grain shape can have an impact on the ease or otherwise with which the grain can be milled.

Starch is readily isolated from grain of the invention such as wheat grain using standard methods, for example the method of Schulman et al. (1991). On an industrial scale, wet or dry milling can be used. Starch granule size is important in the starch processing industry where there is separation of the larger A granules from the smaller B granules.

Food Products

The invention also encompasses foods, beverages or pharmaceutical preparations produced with products, preferably those comprising starch, obtained from the plants or grain of the invention. Such food production might include the making of flour, dough or other products that might be an ingredient in commercial food production. The grain of the invention or products derived therefrom containing starch may be used in a variety of food applications for human consumption. As used herein, "humans" refers to *Homo sapiens*.

The grain derived from the altered wheat plant can be used readily in food processing procedures and therefore the invention includes milled, ground, kibbled, pearled or rolled grain or products obtained from the processed or whole grain of the plants of the invention, including flour. These products may be then used in various food products, for example farinaceous products such as breads, cakes, biscuits and the like or food additives such as thickeners or binding agents or to make drinks, noodles, pasta or quick soups. The grain or products derived from the grain of the invention are particularly desired in breakfast cereals or as extruded products. The starches of the invention can also be used to form high strength gels that are useful in the confectionery industry or allow lower molding and curing times. They may also be used as a coating, for example, to reduce oil absorption in deep-fried potato or other foods. The starch may be incorporated into fat or oil products such as margarine or shortening, salad dressing, egg products such as mayonnaise, dairy products such as icecream, yoghurt or cheese, cereal products such as corn or wheat flour, fruit juices, other foods or food materials, or the altered starch may be processed into beverages or foods such as bread, cake, biscuits, breakfast cereals, pasta, noodles or sauces.

In bread, the starch products in the form of flour or wholemeal may substitute for 10% (w/w) or more of unaltered flour or wholemeal, preferably substituting at least 30% and even more preferably at least 50% of the unaltered flour or wholemeal. The formulation might therefore be, for example, flour 90 parts, altered wheat starch 10 parts, fat 2 parts, salt 2 parts, improver 1 part, yeast 2.5 parts. The production of the bread may be by a rapid dough technique or other techniques as is known by those skilled in the art.

Alternatively, the starch product of the invention may be incorporated into a farinaceous based pasta product. The amount of starch of the invention employed in the pasta composition may be in the range of 10-100% (w/w) based on the total weight of farinaceous material more particularly in the range of 10 to 80%. Suitable other farinaceous materials will readily be chosen by a person skilled in the art. Other material may also be added to the composition for example dry or liquid eggs (yolks, whites, or both) or high protein substances such as milk protein or fish protein. Vitamins, minerals, calcium salts, amino acids, buffering agents such as disodium hydrogen phosphate, seasoning, gum, gluten or glyceryl monostearate may also be added.

Other parts of the plants of the invention that are edible may be used as foods for human consumption or as feed for animal use. For example, leaves, stems, roots, tubers, fruit, pods or extracts or parts of these comprising cells of the invention from any of these may be used for human or animal consumption. Use of plants as fresh or processed fruit or vegetables is well known in the art, and such uses are encompassed by the invention. Increased digestibility of the plants of the invention and parts thereof may provide advantages for use of these materials as animal feed such as, for example, as feed for pigs, cattle, horses, poultry such as chickens and other animals. In particular, advantages are expected from increased starch digestibility of the products for efficiency of conversion of the animal feed and consequently increased growth rates.

The food or beverage or pharmaceutical preparation may be packaged ready for sale or in bulk form. The invention also provides methods of preparing the food, beverage or pharmaceutical preparation of the invention, and recipes or instructions for preparing such foods or beverages. The methods may comprise the steps of harvesting the plant or plant part, separating grain from other plant parts, crushing, extracting, milling, ginning, cooking, canning, packaging or other processing steps known in the art. The methods or recipes or instructions may include the steps of processing the plant product of the invention and/or admixing it with other food ingredients, such as heating or baking the mixture or the product to, for example, at least 100° C. The method may include the step of packaging the product so that it is ready for sale.

Feeds and Animal Use

The plants of the invention and products obtained or produced therefrom, preferably a harvested product such as, for example, grain, has advantages as feed for animals. Without being limited to this theory, it is thought that this is due to increased digestibility and bioavailability of the starch in the product. In a preferred embodiment, this is associated with an increased level of amylases in the product. Although a reduction in starch phosphate content by itself in the product may reduce digestibility, this was counteracted by the increased level of amylases, particularly α-amylases, and the net effect was for increased digestibility. This has particular benefit for the efficiency of conversion of the feed into animal product, which may thereby be increased by at least 2%, preferably at least 5% or at least 7%, relative to the unmodified corresponding wild-type product. This benefit may be seen for either young animals such as chickens, calves or lambs, or with older animals growing into full size. The efficiency of feed conversion can be readily measured using methods known in the art.

Industrial Use

The plant products, preferably grain, have particular advantages in production of industrial products such as, for example, ethanol. The association of increased production parameters such as yield with increased conversion of the starches to sugars observed as described herein provides particular benefits. For example, use of the products of the invention in conversion of starch to sugars for fermentation requires less exogenous amylase to be added, and allows operation at lower temperatures, so reducing energy costs.

The present invention is further described by the following non-limiting Examples.

EXAMPLE 1

Materials and Methods

Extraction of Starch from Grain

Mature seeds were milled using a MicroMill from Metefem (Prototype) and the ground material passed through a 0.5 mm screen. The resultant wholemeal was weighed and water equivalent to 50% of the weight added to soften the tissue. A dough was made by mechanically mixing the water and flour. Water in excess was added to extract starch from the gluten and then the starch suspension was filtered through a 100 μm filter to remove debris. The extraction was repeated 4 times or until there was no starch left in the dough. The starch was pelleted by centrifugation (5,000 rpm, 10 minutes at 4° C.). The protein cap was removed and the starch was resuspended in excess water. The wash was repeated 3 times. The extracted starch was freeze dried in a FTS Freeze Drier (Model No. FD-3-55D-MP). By this method, 10 g of grain yielded approximately 6 g flour and then 3 g starch.

Extraction of Starch from Leaf Material

Starch was extracted from plant leaves using the method described in Delvalle et al., (2005). Leaf samples were freeze dried, then ground in 15-25 ml Extraction Buffer (MOPS100 mM, pH7.2, EDTA 5 mM, Ethylene glycol 10% (w/v)) with a Polytron blender while keeping the samples chilled on ice. The mixture was filtered through a two-layer Miracloth filter and centrifuged, retaining the pellet comprising the starch. The starch was then purified through a 90% Percoll gradient by centrifugation at 4,000 rpm for 40 minutes at 4° C.

Measurement of Phosphate and Glucose-6-Phosphate Levels in Starch Samples

Total phosphate content in starch was determined using a Malachite Green method adapted from Ekman and Jager, (1993). 10 mg of dry starch was solubilised by resuspending it in 500 μL of 10% DMSO solution and boiled the mixture for 10 minutes. 200 μl of solution was mixed with 200 μL of Clark and Lub Buffer (0.054M KCl, 0.145M HCl); 120 μL $H_2O$; 80 μL of HCl 4M and 200 μL of Malachite Green solution 3:1 (Malachite Green 0.2% solution: $(NH_4)_6Mo_7O_{24}(4H_2O)$ 10% solution in 4M HCl). The acid hydrolyses the phosphate groups from C6 and C3 and the free phosphate is measured by the Malachite Green assay. A spectrophotometer was used to measure the optical density at 660 nm. A standard curve was also prepared using standards of a G1P solution from 0.01 to 5 mM, treated as for the starch samples. The phosphate content was usually determined on triplicate samples and the average expressed as mmoles per mg of starch:

Glucose-6-Phosphate (G6P) levels were measured by an amyloglucosidase assay method adapted from Delrue et al., (1992). Glucose-6-Phosphate dehydrogenase was used specifically in this assay, as follows. 5 mg dried starch was dissolved in 500 μL 10% DMSO in water and boiled 10 minutes to dissolve the starch. Dilution series were made in duplicate. Starch in each sample was degraded by the action of 70 μL of AmyloGlucosidase solution (AGS, Starch assay kit from Enzytec) for 2 hours at 55° C. The reaction was stopped by adding 350 μL of water and 350 μL of solution 1 (TEA Buffer pH 7.6, NADP, ATP (from Starch assay kit from Enzytec)). The OD at 340 nm was measured (designated as $OD_0$) before adding the following reagent. For the first series to measure the amount of starch, 5 μL of solution mix (Hexokinase and G6PdH (200 U/100 U per 0.7 mL, from Starch assay kit from Enzytec) was added. For the second series to measure the amount of G6P, 5 μL of G6PdH was added without hexokinase (G7877-2KU, Sigma, 18 units/mL). The mixtures were incubated at 25° C. for 15 minutes and the OD was measured at 340 nm. The measurement was repeated every 10 minutes until stabilization of the OD (designated ODf).

The amount of starch or the amount of G6P was calculated using the equation:

$$[\text{Starch or } G6P][\text{mg} \cdot \text{mL}^{-1}] = (ODf - ODo) \times 1.069/\text{dilution factor}$$

The first series measured the concentration and the amount of starch in each sample, while the second series measured the amount of G6P present in the starch.

Starch Granule Size Distribution

The granule size distribution of isolated starch samples, prepared as starch slurries in water was determined using a laser diffraction particle size analyser (Model 2600c Droplet and Particle Sizer, Malvern Instruments, Malvern, UK). "A granules" were defined as larger than 10 µm in diameter as determined by the analyser, "B granules" as less than 10 µm in diameter. The granule size distribution as defined herein was expressed as the frequency of B granules expressed as a percentage of the total volume of starch granules (Stoddard, 1999).

Starch Properties

The distribution of chain lengths in the starch was analysed after debranching of the starch samples with isoamylase to release glucosidic chains from the amylopectin in the samples. Fluorophore assisted carbohydrate electrophoresis (FACE) was carried out as described by O'Shea et al., (1998) using a P/ACE 5510 capillary electrophoresis system (Beckman) with argon-LW detection.

The gelatinisation temperature profile of each starch sample was measured in a Pyris 1 differential scanning calorimeter (Perkin Elmer, Norwalk Conn., USA). The analysis directly measures the energy required to gelatinise the starch. Samples were prepared by premixing the starch in water at a ratio of 1:2 (dry starch:water). The DSC pan was filled with the mixture and hermetically sealed. The reference used was an empty pan. Four measurements were made for each of the 2 endotherms (gelatinisation and amylose-lipid dissociation): initial (onset) temperature, peak temperature, final temperature and enthalpy.

The viscosity of starch solutions was measured on a Rapid-Visco-Analyser (RVA, Newport Scientific Pty Ltd, Warriewood, Sydney), for example using conditions as reported by Batey et al., 1997. The parameters that were measured included peak viscosity (the maximum hot paste viscosity), holding strength, final viscosity and pasting temperature.

The swelling volume of flour or starch was determined according to the method of Konik-Rose et al (2001). The uptake of water was measured by weighing the sample prior to and after mixing the flour or starch sample with water at 90° C. and following collection of the gelatinized material.

Fractionation of Starch by Gel Permeation Chromatography

Gel permeation chromatography on Sepharose columns was used to separate starch into amylopectin (larger molecules) and amylose (smaller molecules) fractions. An amount of 1 to 2.5 mg starch dissolved in 500 µL of 10 mM NaOH was applied to a Sepharose CL2B column (0.5 cm internal diameter×65 cm long) equilibrated with 10 mM NaOH and chromatographed using this solution. Fractions of 250 to 300 µL were collected at a rate of 1 fraction/1.5 min. Glucans in each fraction were detected through the iodine-polysaccharide interaction according to Banks et al. (Starch/die Starke, 23:118-124, 1971) or by glucose assay (Enzytec).

The amylose content of starch samples was also determined by the colorimetric (iodometric) method of Morrison and Laignelet (1983) with slight modifications as follows. Approximately 2 mg of starch was weighed accurately (accurate to 0.1 mg) into a 2 ml screw-capped tube fitted with a rubber washer in the lid. To remove lipid, 1 ml of 85% (v/v) methanol was mixed with the starch and the tube heated in a 65° C. water bath for 1 hour with occasional vortexing. After centrifugation at 13,000 g for 5 min, the supernatant was carefully removed and the extraction steps repeated. The starch was then dried at 65° C. for 1 hour and dissolved in urea-dimethyl sulphoxide solution (UDMSO; 9 volumes of dimethyl sulphoxide to 1 volume of 6 M urea), using 1 ml of UDMSO per 2 mg of starch (weighed as above). The mixture was immediately vortexed vigorously and incubated in a 95° C. water bath for 1 hour with intermittent vortexing for complete dissolution of the starch. An aliquot of the starch-UDMSO solution (50 µl) was treated with 20 µl of $I_2$-KI reagent that contained 2 mg iodine and 20 mg potassium iodide per ml of water. The mixture was made up to 1 ml with water. The absorbance of the mixture at 650 nm was measured by transferring 200 µl to microplate and reading the absorbance using an Emax Precision Microplate Reader (Molecular Devices, USA). Standard samples containing from 0 to 100% amylose and 100% to 0% amylopectin were made from potato amylose and corn (or potato) amylopectin (Sigma) and treated as for the test samples. The amylose content (percentage amylose) was determined from the absorbance values using a regression equation derived from the absorbances for the standard samples.

Alpha-amylase Enzyme Assay

Alpha amylase activity in flour or wholemeal samples was determined using the Ceralph Amylase assay kit from Megazyme International Ireland Ltd, as recommended by the manufacturer. On hydrolysis of the oligosaccharide added from the reagent mix by endoacting alpha amylases, the excess quantities of alpha-glucosidases present in the mixture gave quantitative hydrolysis of the oligosaccharide to produce glucose and free p-nitrophenol. Essentially, an aliquot of cereal extract was incubated with substrate mixture at 40° C. for 20 minutes, and the reaction was terminated and colour developed by addition of a weak alkaline solution. The absorbance at 400 nm was measured, which related directly to the level of alpha-amylases in the sample analysed. The results were expressed in CU (ceralpha unit) per g flour or extract.

Wheat Transformation by Particle Bombardment of Immature Embryos of Wheat

Gold particles were coated with purified DNA of two plasmids: 2 mg of plasmid DNA encoding a selectable marker gene (npt), in this instance pCMneoSTLS2 (Maas et al., Mol Breeding, 3: 15-28, 1997), and 2 µg of plasmid DNA encoding the gene of interest, in this instance pBx17-GWD_IR, by $CaCl_2$/spermidine precipitation as previously described by Cao et al. (Plant Cell Reporter, 11:586-591, 1992). The gold particle/DNA mixture contained 30 mg/ml gold particles with an average size of 1.5-3.0 µm. For bombardment, 50 immature embryos, 12 days after anthesis and approximately 1.5-2 mm long, were isolated and the embryonic axes removed. These were placed in the centre of an agar plate containing high-osmotic medium MSM, which was MS medium containing 150 g/L maltose and 0.1 g/L Myo-inositol, to form a target area of about 3 cm in diameter. The target embryos were incubated (pretreated) on the MSM plates for 4 hours as described by Vain et al. (Plant Cell Reporter, 12: 84-88, 1993) and then bombarded with 5 µl of the coated gold particle mixture under partial vacuum (ca. 85 kPa), using a PDS-1000/He biolistic delivery system. The distance between the loaded DNA and the target embryos was 9 cm and the pressure used was 900 kPa.

Regeneration/Selection of Transformants

Twenty-four hours after bombardment with the mixture of the plasmids, the embryos were transferred onto MSR medium (MS medium, pH5.9 containing 30 g/L sucrose; 0.1 g/L Myo-inositol and 2.5 mg/L 2,4-D) and incubated for 14 days in the dark at 24° C. for the somatic embryo induction. The cultures were then transferred onto the selection medium MSWG50 (MS medium, pH 5.9 containing 30 g/L sucrose, 0.1 g/L Myo-inositol) with 50 mg/L geneticin (G418) as selective agent and maintained in a 16 h light (approx. 25 µE m$^{-2}$s$^{-1}$) and 8 h dark regime. They were then transferred to new plates of the selection medium MSWG50 every 3 weeks. The plantlets that formed were subcultured once onto fresh MSWG50 for further growth. Plantlets about 10 to 15 cm high were transplanted into soil on a misting bench for 2 weeks and then transferred to a glasshouse with a temperature regime of 24° C. (day) and 18° C. (night). The presence of the transgene in the regenerated plants was confirmed by extracting DNA from tissue samples and carrying out PCR reactions using transgene-specific promers.

Extraction of RNA from Plant Samples and Quantitative RT-PCR.

Total RNA was extracted from leaf samples using an RNeasy Plant Mini Kit (QIAGEN, Hilden, Germany) following the supplier's instructions. cDNA synthesis was performed using the Invitrogen first strand synthesis kit with an oligodT Primer. Specific amplifications were detected by using the Brilliant SYBR Green QPCR MasterMix (STRATAGENE). The specific fluorescence was detected at 520 nm and analyzed with the MX4000 analysis software by comparison with specific standard curves. One-step RT-PCRs were also performed using the Qiagen one-step RT-PCR kit (QIAGEN, Hilden, Germany).

EXAMPLE 2

Identification of GWD and PWD Genes in Wheat and Other Cereals

The amino acid sequences for the R1 protein sequences from potato (Accession No. AAK11735) and the PWD protein of *Arabidopsis* (NP_194176) were used as query sequences to interrogate wheat EST sequences in the NCBI database using the BLASTN program. 17 ESTs were identified (listed below) which could be aligned together and assembled into a 2273 basepair sequence (SEQ ID NO: 1).
Dbj|CJ626658.1| CJ626658 Y. Ogihara unpublished cDNA library.
gb|CV773056.1| FGAS067452 *Triticum aestivum* FGAS library.
dbj|CJ694861.1| CJ694861 Y. Ogihara unpublished cDNA library.
gb|CA743865.1| wrils.pk006.k23 wrils *Triticum aestivum* cDNA.
gb|BQ240991.1| TaE05010D07R TaE05 *Triticum aestivum* cDNA.
dbj|CJ696711.1| CJ696711 Y. Ogihara unpublished cDNA library.
dbj|CJ730334.1| CJ730334 Y. Ogihara unpublished cDNA library.
dbj|BQ237936.1| TaE05010D07F TaE05 *Triticum aestivum* cDNA.
gb|CK197520.1| FGAS005996 *Triticum aestivum* FGAS library.
dbj|CJ650741.1| CJ650741 Y. Ogihara unpublished cDNA library.
dbj|CJ542660.1| CJ542660 Y. Ogihara unpublished cDNA library.
gb|CK197837.1| FGAS006317 *Triticum aestivum* FGAS library.
dbj|CJ590517.1| CJ590517 Y. Ogihara unpublished cDNA library.
gb|BE516396.1| WHE609_A08_A15ZA Wheat ABA-treated embryo.
gb|DY742247.1| EST0817 Cold treated wheat cDNA library.
dbi|CJ673389.1| CJ673389 Y. Ogihara unpublished cDNA library.
dhj|CJ566400.1| CJ566400 Y. Ogihara unpublished cDNA library.

This sequence was used to interrogate wheat sequences in the TIGr database (http://www.tigr.org/tdb/e2k1/tae1/). This yielded a 3677 base pair cDNA sequence (SEQ ID NO: 2) (TIGr Accession No. TA53350_4565) overlapping the 2273 base pair sequence. These two sequences displayed 99% identity in the overlapping region. When the predicted amino acid sequence (SEQ ID NO: 3) encoded by this 3677 nucleotide sequence was compared to protein sequences in the NCBI protein database, it was seen that it displayed high similarity with the R1 protein sequences from potato and *Arabidopsis*. (71% and 67% identity, respectively). The wheat sequence also displayed high degree of similarity to a sequence from the rice genome (Os06g0498400) which was presumed to be the homolog from rice. The wheat cDNA sequence was 87% identical to the rice nucleotide sequence, and the amino acid sequences were 88% identical. The wheat GWD nucleotide sequence is given as SEQ ID NO: 2 and the amino acid sequence as SEQ ID NO: 3.

When the wheat cDNA sequence was compared to the genomic sequence from rice (Os06g0498400), the exon/intron structure of the rice gene could be determined, and the presumed exon structure of the wheat cDNA was determined (Table 8).

Examination of barley EST sequences resulted in identification of barley EST BU993423 of 663 nucleotides (SEQ ID NO: 4) which showed similarity with the GWD sequences from wheat and rice in the region of exon 23 and 3', and that is thought to correspond to the homologous barley gene. Another wheat cDNA was identified, of 4302 nucleotides (SEQ ID NO: 5), which encoded a protein which had a starch binding domain similar to potato R1 protein.

The 3677 by wheat cDNA sequence contained an opening reading frame (ORF) of 3027 bp from nucleotide position 382 to 3409; it appeared to be full-length in that when the cDNA was aligned with the rice cDNA, the two sequences were similar over the full length of the rice cDNA. This ORF coded for a protein of 1009 amino acids sequence with a calculated molecular weight of 112.8 kD. The protein sequence contained 3 conserved domains with putative function: A starch binding domain from approximately amino acids 100 to 200, a phosphor-acceptor site from about amino acids 200 to 300, and a PEP/pyruvate Binding Domain from approximately amino acid 740 to the C-terminus, which domain is thought to reversibly catalyse the conversion of ATP to AMP.

Two other wheat ESTs, CA484881 and CO347457, were identified which had homology to the *Arabidopsis* sequence encoding PWD. These did not match the 2273 by sequence but encoded polypeptides which displayed homology with starch binding domains and the PWD protein from *Aradidopsis*. Specifically, these two PWD EST sequences displayed similarity with the amino acids 973-1153 (82% identity) and amino acids 1172 to 1196 (88% identity) of the gene ATGWD2/GWD3/PWD (PHOSPHOGLUCAN, WATER DIKINASE) [*Arabidopsis thaliana*] (NP_194176), respectively. They also displayed homology with PWD of rice (Os12g0297500). The full-length sequences for the wheat PWD gene can be isolated by 5'- and 3' RACE techniques using primers based on the EST sequences, or other methods known in the art.

Further searching identified four ESTs from sorghum which where homologous to the wheat GWD cDNA sequence (SEQ ID NO: 2) and therefore appeared to be part of the sorghum GWD gene. These were: Accession No: BI245998 (SEQ ID NO: 11) having a nucleotide sequence which was 83% identical to the wheat GWD sequence (SEQ ID NO: 2) from nucleotide position 2057 to 2542; Accession No: CF074015 having a sequence 89% identical to wheat GWD from nucleotide 874 to 1559; Accession No: EH406623 having a sequence 89% identical to wheat GWD from nucleotide 1323 to 1885; and accession No. CD423248 having a sequence 85% identical to the wheat GWD from nucleotide 2517 to 3434. The full-length sequence for the sorghum GWD gene can be isolated by 5'- and 3'-RACE techniques, using primers based on the above EST sequences, or other methods known in the art.

EXAMPLE 3

Production of Plants Transformed with Constructs to Inhibit GWD Gene Expression

In order to test the effect of inhibiting GWD gene expression, a gene construct was designed that would express a double-stranded RNA molecule for inhibition of the GWD homologous genes in wheat, targeting a conserved region corresponding to the starch binding domain.

The construct contained a promoter from a Bx17 HMW glutenin gene from wheat to express the dsRNA, this promoter was chosen as a tissue specific promoter that is preferentially expressed in the endosperm of cereals. It was therefore expected that the inhibition of gene expression would occur primarily in the endosperm.

The inhibitory gene construct was assembled in the pBx17IRcasNOT cloning vector as follows. The vector contained the following elements in order: the endosperm-specific promoter from the wheat HMWG Bx 17 gene comprising the first 1897 nucleotides of the Bx17 genomic sequence as reported in Reddy et al. (1993) a forward sequence of attR (1447 by including the ccdB negative selectable gene) with a BamHI site at its 5' end and an EcoRI site at 3' end, a rice starch branching enzyme I intron 4 (507 bp from nucleotide 6201 to nucleotide 6674 of Accession No. D10838) in reverse orientation with respect to the promoter, a rice branching enzyme I intron 9 (429 bp, from nucleotide 9112 to nucleotide 9605 of D10838) in forward direction, a reverse sequence of attR (1435 by including a second copy of ccdB) with a SpeI site at its 5' end and a KpnI site at its 3' end, and finally a nos3' transcription terminator sequence (267 bp, from pEmu, Chamberlain et al., 1994). The vector did not contain a selectable marker gene, rather a second plasmid comprising an npt gene was co-transformed to allow selection of transformed cells. The nucleotide sequences referred to by above-mentioned Accession Nos are incorporated herein by reference.

A PCR fragment corresponding to part of the wheat GWD gene was amplified from wheat endosperm cDNA under standard conditions using primers GWDF: 5'-AAAAGGATCCGGTACCGCCTTCTGGCTCAACA-GTTC-3' (SEQ ID NO: 6) and GWDR: 5'-AAAAGAAT-TCACTAGTATCACCTTCACCTCCACGAC-3' (SEQ ID NO: 7) and an annealing temperature of 62° C. The PCR reaction amplified a 597 by fragment of the wheat GWD cDNAs corresponding to nucleotide positions 581 to 1020 of SEQ ID NO: 2 for GWD. This region of the wheat gene, towards the 5' end of the transcribed sequence, corresponded to the part of the potato gene encoding amino acids 470 to 670 of Accession No AAK11735 (this Accession No. herein incorporated by reference). This region in the potato polypeptide was thought to correspond roughly to the starch binding domain of the GWD protein.

The PCR fragment was digested with SpeI and KpnI and ligated to vector pIRBx17casNOT DNA digested with the same pair of restriction enzymes, thereby forming an intermediate pBx17-GWD_R construct. Further DNA of the PCR fragment was then digested with BamI and EcoRI and ligated to pBx17-GWD_R DNA digested with the same enzymes, to form pBx17-GWD_IR.

DNA of this construct was used for biolistic-mediated transformation of wheat immature embryos (cv. Bob White) using gold particles as described in Example 1. About 1100 embryos were treated using the biolistics method, and 25 plantlets were regenerated from these. 18 plants survived to grow to maturity in the glasshouse. When these were tested for resistance to geneticin, indicating the presence of the selectable marker gene, or by PCR screening, 13 positive wheat transgenic plants (designated T0 generation, rsGWD lines) containing pBx17-GWD_IR were identified. The PCR screening was carried out on DNA isolated from leaf samples and used the primer ZLBx17pro located in the promoter of the construct and the GWDR primer 5'-AAAAGAATTCACTAGTATCACCTTCACCTCCAC-GAC-3' (SEQ ID NO: 7). The PCR amplified a 713 by fragment from plants transformed with pBx17-GWD_IR.

EXAMPLE 4

Dikinase Gene Down Regulated and Analysis of Transformed Wheat Plants

The T0 plants were grown in the greenhouse and allowed to self-fertilise to produce T1 seed. Individual T1 seeds of each transgenic line were sown to produce T1 progeny plants. T1 plants which were positive for the presence of the transgene were identified and self-fertilised to produce T2 seed. Such T1 plants were expected to be either homozygous or heterozygous for the transgene; these could be distinguished by analysing the T2 generation for each line. T1 plants which were negative for the presence of the transgene (segregants) were also retained and allowed to self-fertilise, to provide a T2 generation of plants lacking the transgene which could serve as a control (wild-type) for comparison of phenotypic properties.

Starch was isolated from dried T2 grain of transgenic lines as described in Example 1. The starch content of the transgenic grains appeared to be similar to that of the wild-type grain, no significant differences were observed in the starch content. The T2 starch samples were analysed for their glucose-6-phosphate (G6P) content using an adapted protocol from an Enzytec starch assay kit as described in Example 1. Starch samples from 12 rsGWD T1 lines were assayed. Of these lines, 8 contained the RNAi construct and 3 were null segregants which served as (wild-type) controls. Of the 8 transformed rsGWD lines, 7 displayed a clear reduction in the levels of G6P in the grain starch in comparison to the wild-type parent (cv. Bob White) and also in comparison to their wild-type segregates. (See FIG. 1). One line (GWD5-9X) showed a reduced level of G6P compared to Bob White, but was not significantly reduced in G6P level compared to the corresponding null segregant (rsGWD5-9A). These data demonstrated that the targeted gene encoded a functional GWD in wheat.

Structural and Molecular Analysis of the Starch.

Figure 2:
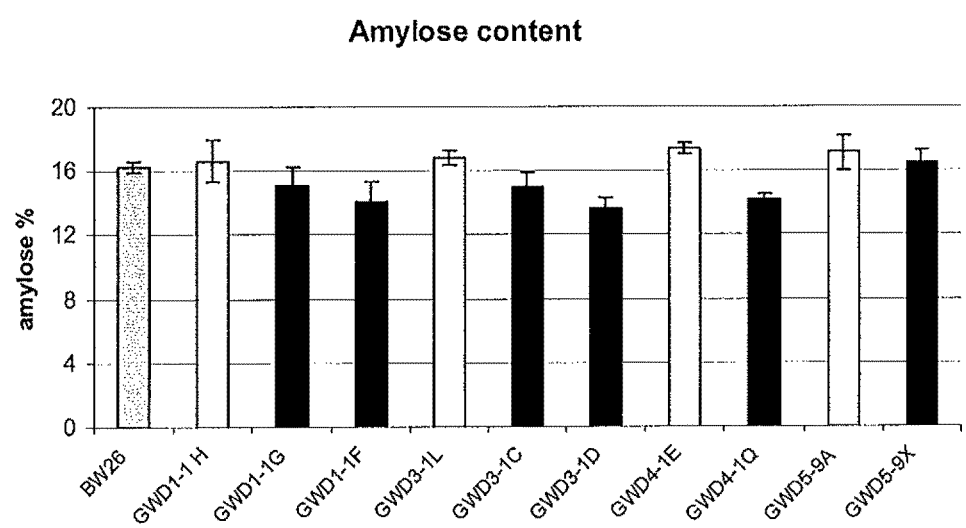
FIG. 2 is a graphical representation of amylose content in grain starch of rsGWD transgenic wheat.

Starch samples from grain of these transgenic lines was also analysed for their chain length distribution, amylose content and also the granule size distribution. The chain length distribution profiles were obtained by capillary electrophoresis after isoamylase debranching of the starch as described in Example 1. For the 12 lines analysed, no significant modifications of the chain length distribution were observed, with the position of the main peak arising at the same degree of polymerisation (DP) for each sample, and the curves virtually identical when superimposed. When the granule size distributions were compared, or the frequency (%) of B-granules in the grains, likewise no significant changes were observed between the transgenic and non-transgenic lines. The amylose content (expressed as a percentage of the total starch extracted from the grain) in the starch samples for most of the transgenic lines was slightly lower (2-3% lower) than the corresponding controls or parent line Bob White (FIG. 2). Transgenic line rsGWD5-9X had an amylose content which was not statistically different to its control.

Physiochemical Properties of the Starch.

The physicochemical properties of starch samples from the transgenic lines were investigated, including the pasting properties, viscosity and swelling index.

Figure 3:
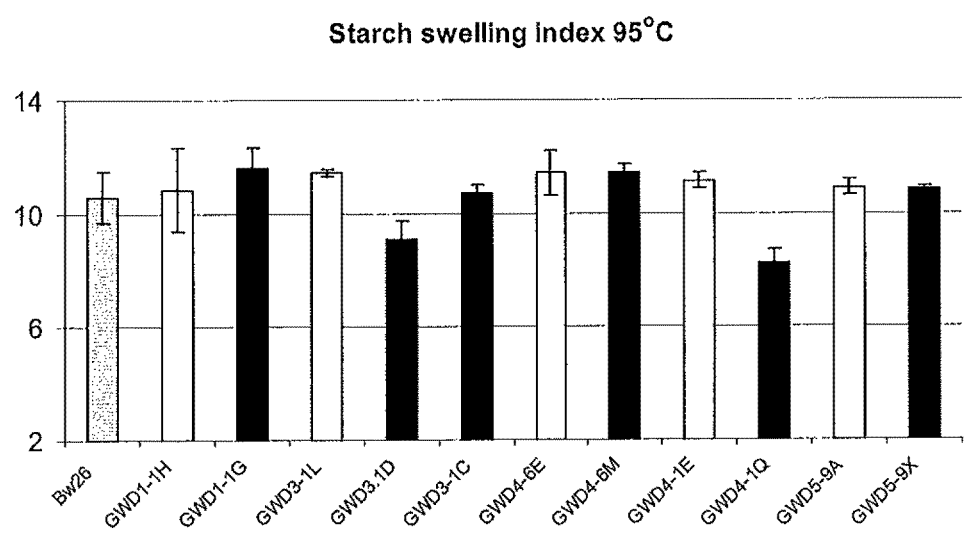
FIG. 3 is a graphical representation of data showing the swelling power of grain starch of rsGWD transgenic wheat.

The swelling power of starch from the transgenic lines was tested as described in Example 1, and the data compared to the data for control samples (FIG. 3). Starch from transgenic grain with the greatest reduction in starch bound G6P content, i.e. greatest extent of gene silencing at the phenotypic level, demonstrated a significant reduction (at least 20%) of their swelling index at 95° C. while no significant modification was observed for the other lines.

Figure 4:
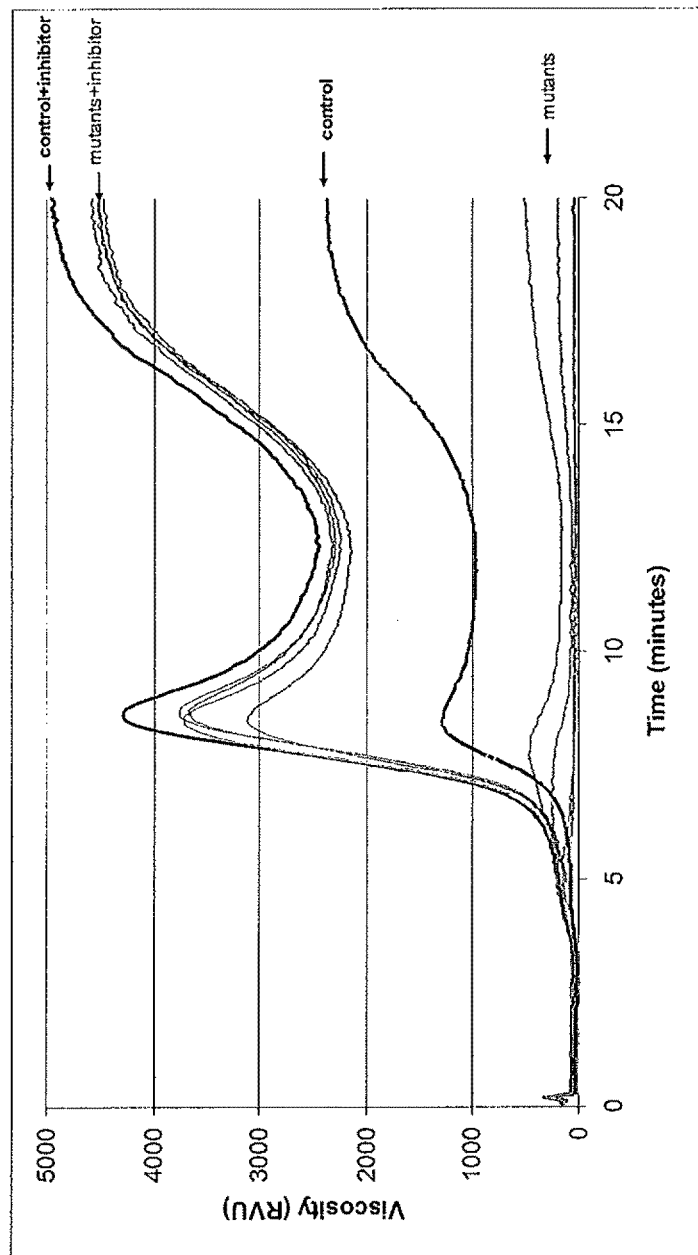
FIG. 4 is a graphical representation of data showing the pasting property (starch viscosity) of grain starch (either wholemeal without α-amylase inhibitor, or purified starch in the presence of α-amylase inhibitor) from rsGWD transgenic wheat.

The pasting properties of starch were analysed using 9% (w/v) starch suspensions, prepared using 3 g of starch and 25 mL of water, and a Rapid Visco Analyser (Newport Scientific, Sydney, Australia) in the presence of silver nitrate at a final concentration of 4 μg/mL as an α-amylase inhibitor, or in the absence of added inhibitor. Representative data are shown in FIG. 4 and Table 4 which display the viscograms for starch isolated from 5 selected transgenic lines and the control Bob White. The lines with the greatest extent of reduction of G6P also displayed the greatest reduction in the pasting values of the grain starch, in particular for the peak viscosity and peak time. However, transgenic lines with a lesser effect on G6P content showed only slight or no modification of their RVA profiles. The reduction in viscosity observed for the rsGWD4-1 line was at least 30%. In a similar fashion to the other grain starch analyses, starch from line rsGWD5-9X displayed the same viscosity profile as its control.

Analysis of Enzyme Activities Relating to Starch.

Unexpectedly, the same type of analysis carried out on wholemeal flour samples (in contrast to the use of purified starch, above) from the transgenic grain in absence of alpha-amylase inhibitor revealed a strong, particular phenotype (FIG. 4). The reason for adding amylase inhibitor in this experiment was to attempt to obtain a better resolution of the viscogram and to avoid any threshold due to amylolytic enzymes as was seen for the parent line (BW26). However, we were surprised to see that the RVA profile of the wholemeal flour produced from transgenic grain was completely collapsed with very low viscosity peak and final viscosity. The profile obtained for wholemeal flour from the parent line was restored by adding silver nitrate or EDTA as amylase inhibitors to the suspension before analysis, obtaining a similar shaped profile to the isolated starch RVA profile.

Figure 5:
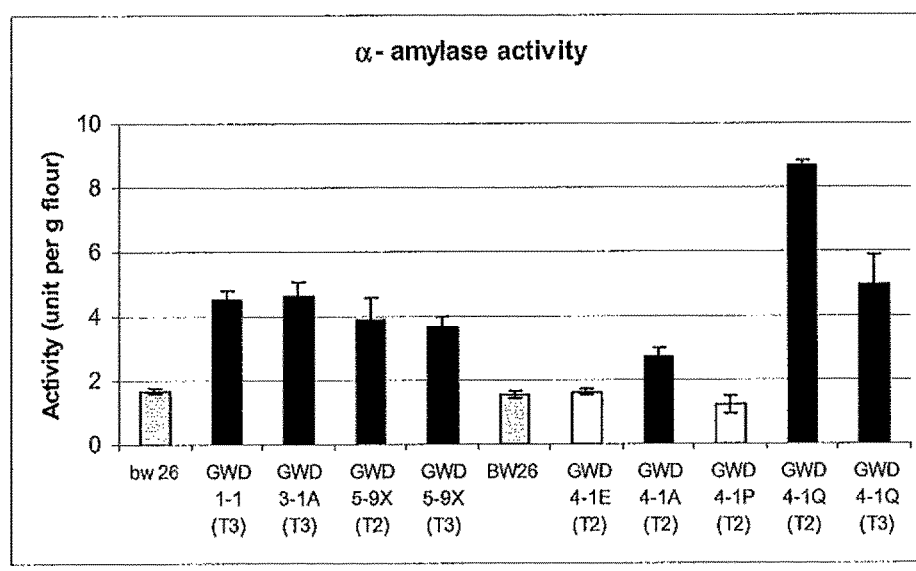
FIG. 5 is a representation of data showing the elevated α-amylase activity of rsGWD transgenic wheat seeds relative to controls.

This result suggested to us the presence of an increased pool of alpha-amylases in the transgenic grain. In order to test this hypothesis, the levels of alpha-amylase activity within the seeds were assayed as described in Example 1. Data for selected lines including the following (T3) generation of these lines is shown in FIG. 5. For the rsGWD lines analysed, the alpha-amylase activity appeared to be elevated at least about 2- to 5-fold compared to the parent line or the control lines. When β-amylase activity was measured, increases were observed of at least 20% in the flour compared to the non-transformed control. It was concluded that reduced GWD in the plant was associated with increased accumulation of amylases in the transgenic grains, both α-amylase and β-amylase.

The levels of other enzymes involved in starch degradation were also measured in the transgenic grain, using the protocols described by Zeeman et al., Plant Journal 15: 357-365 (1998). The enzymes α-glucosidase, β-glucanase, D-enzyme, cellulase, lichenase and xylenase were all present in similar amounts in the transgenic seed compared to the control seed, although some seeds showed slight increases in individual enzyme activities. It was concluded that the major effect on enzyme activity was on amylases, in particular α-amylase.

Dissection of developing seeds (25 DPA) and mature grain from transgenic and control plants to separate the aleurone and pericarp, endosperm and embryo tissues with subsequent measurement of amyalse activity on these tissues showed that the increased α-amylase activity was localised primarily in the aleurone and pericarp. Only low levels of activity were observed in the endosperm and very low activity in the embryos.

When aleurone layers were isolated and stained with propidium iodide, which is a fluorescent compound that cannot enter living cells having an intact cell membrane, or with carboxyfluorescein diacetate (CFDA), which can cross the cell membrane and enter the cells, it was observed that there were many more cells in the aleurone layers of the transgenic grain that were progressed in programmed cell death compared to the control aleurone layers.

Other Carbohydrates

Levels of several carbohydrates were analysed from leaves, heads and stems of the plants at 25DPA. Assays were performed in two independent experiments. The analyses showed that there were substantial increases in fructose, sucrose and glucose levels in stems of the transgenic plants compared to the wild-type Bob White plants. Starch levels were also increased, but fructan levels were decreased in the stems.

Altered Plant Phenotypes.

Figure 6:
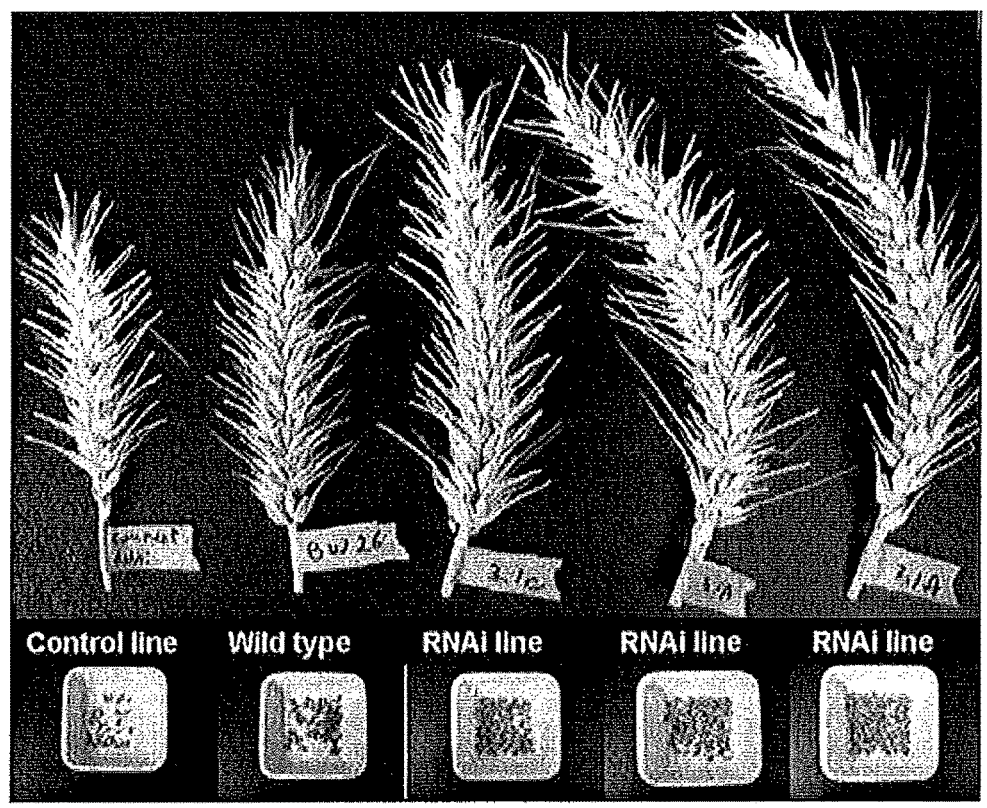
FIG. 6 is a photographic representation showing enhanced vigour, biomass and yield of rsGWD transgenic wheat.

Surprisingly and unexpectedly, it was also observed that the down-regulation of GWD gene expression in the transformed wheat lines resulted in major modifications of the plant morphology and development when grown in the greenhouse. Most importantly, when grown under the same environmental conditions including light, temperature and watering, the transgenic plants appeared more vigorous, healthier and produced more biomass including more leaves, heads and spikelets than the corresponding control plants. The amount of grain produced per plant was increased substantially by at least 50% compared to the parent or control plants, see data in Table 5 for seed production (in grams of seed per plant) and FIG. 6 which shows typical head sizes.

To confirm these observations, further growth studies were carried out on selected transgenic lines, controls and parent plants to allow statistical analysis. The parameters measured included germination rate, leaf area at various stages of growth, and the number of heads per plant. These analyses were carried out for 5 replicates of each plant line. The data are shown in the Table 6. It was concluded from the data that the biomass production of the transgenic plants was increased from an early stage after germination, for example at the 2-leaf stage, through to when the heads formed. Biomass increased by an average of 30% and in some plants by more than 40%. Leaf area increased by at least 50%, in some lines by more than 60%. The number of tillers per plant increased by more than 15%, sometimes by more than 20%. The number of heads per plant increased by at least 40%, in some cases by at least 50%. Typically, the seed production per plant was increased by at least 40% or at least 50% with a similar individual seed weight.

Even more surprisingly, growth and development of plants for transgenic line rsGWD5-9X was also substantially affected. As shown above, grain starch of this line was not significantly modified in its level of G6P or viscosity, so it was not immediately apparent why growth and development of this plant line should be affected. It was thought prior to these observations that the HMW glutenin promoter used to create the RNAi inhibitory construct would be limited in expression to the endosperm. However, the observed growth profile strongly suggested that the promoter expression was "leaky", in particular in leaves of the plant where transitory starch metabolism occurs following photosynthesis. In order to test this possibility of an effect of the RNAi construct on the transitory starch metabolism, the levels of starch G6P present in leaves from a selection of transgenic and control lines were measured at the end of the daylight period. This timepoint corresponded to the greatest activity of GWD and accumulation of transitory starch during the 24 hour period, and was chosen since the enzyme activity shows circadian variation.

Figure 7:
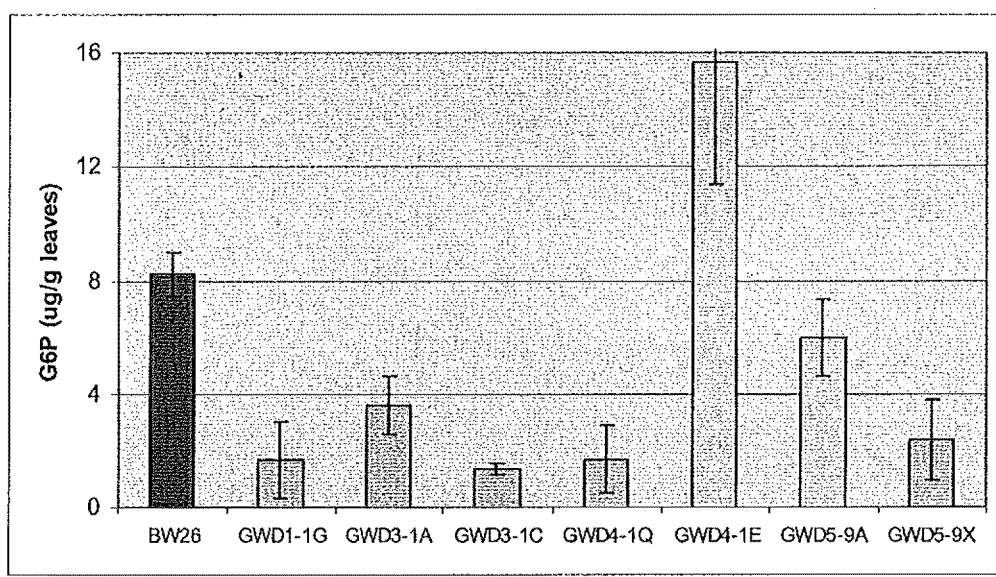
FIG. 7 is a graphical representation of data showing the decreased level of G6P content in transitory (leaf) starch of rsGWD transgenic wheat lines.

The data obtained are shown in FIG. 7. In keeping with the observations on growth and development of this line, the G6P levels present in the leaf starch decreased drastically in comparison to cv. Bob White or the control plants. This result confirmed that the RNAi construct must have been expressed at levels in leaves sufficient to perturb the regulation of GWD in leaves and thereby affect the transitory starch metabolism.

CONCLUSIONS

Decrease of the Glucose-Water-Dikinase activity by a construct that encoded an inhibitor of expression of the gene encoding GWD in transgenic wheat was shown to reduce glucose-6-phosphate content in reserve starch, in this case grain starch. This proved that the targeted gene encoded functional GWD. The reduction of monoesterified phosphate levels contributed to modification of the pasting properties and a reduction in the swelling index of the starch. In a novel and unexpected observation, the grain from these transgenic plants also displayed greatly increased levels of α-amylase and significant increases in levels of β-amylase, which also affected the natural pasting properties of the wholemeal flour. Both of these amylases are normally expressed primarily in the aleurone layer of the grain, and particularly after imbibition and during germination of the grain, so it was considered likely that most of the increased amylase would also be expressed in the aleurone layer. Such effects were only modest when purified starch was analysed, where proteins were removed. Such effects on the flour would be expected to have an impact on breadmaking and other food applications. However, the most unexpected observation was that the RNAi construct greatly influenced plant growth and development, leading to substantially increased biomass production and grain yield. The biomass and seed production was increased by 30 to 40% or more, associated with a reduction of the glucose-6-phosphate levels in transitory starch. Based on the results obtained with plants of transgenic line rsGWD5-9X, the effect on growth and yield was mediated primarily by modifying gene expression in green tissues such as the leaves, not in the developing grain. This was unexpected because the promoter used to drive the RNAi construct was chosen to be endosperm specific, with very low expression in other tissues. Moreover, the effects on plant development and morphology were observed long before seed development.

EXAMPLE 5

Effect of Inhibiting GWD Gene Expression in Different Genetic Backgrounds

Figure 8:
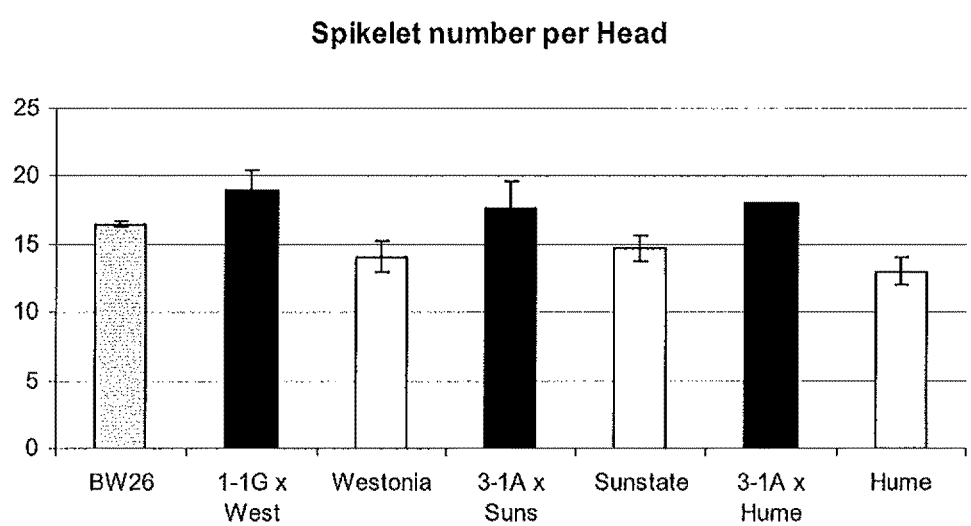
FIG. 8 is a graphical representation of data showing the increased number of spikes per plant in GWD transgenic wheat lines of different genetic backgrounds.
Figure 9:
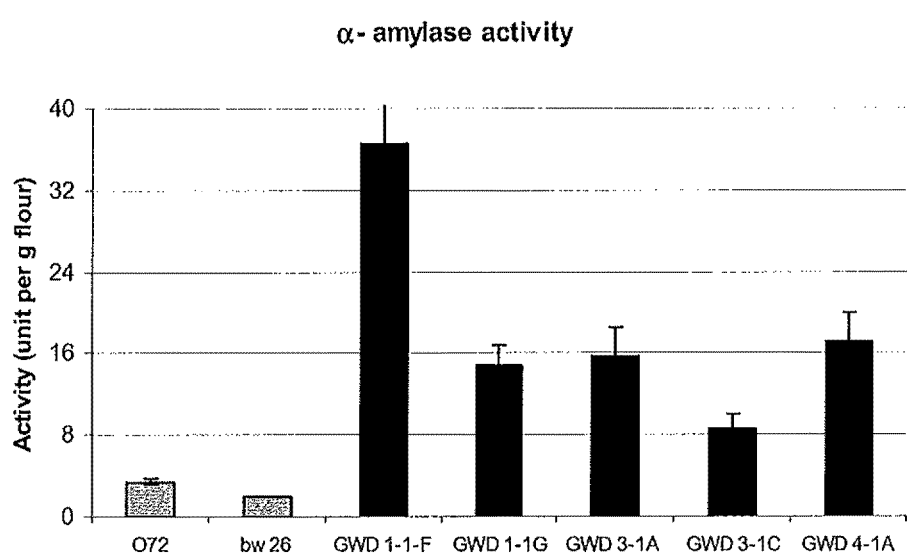
FIG. 9 is a representation of data showing the elevated α-amylase activity of rsGWD transgenic wheat seeds relative to controls.

To establish the effect of GWD gene down-regulation in different genetic backgrounds, transgenic plants containing the pBx17-GWD_IR construct were crossed with plants of the commercial breadwheat cultivars Westonia, Hume and Sunstate. Mature F1 seeds were obtained. When these seeds were sown in a greenhouse under controlled conditions, F1 plants from crosses with each of the three commercial cultivars showed an increased number of spikelets per plant, see for example the data in FIG. 8 for 4 or 5 plants for each line. It was concluded that the increased production parameters extended to different genetic backgrounds.

Plants obtained from these seeds and from further backcrosses will be further analysed in the manner as described above for growth and development as well as for starch properties. Germination of the seed and development of plants will be compared to the parental plants in order to confirm the phenotypes observed for the transgenic lines in the cv. Bob White background. Characteristics such as germination time, early stage growth rate and leaf area will be measured, in addition to tiller number, head number and yield. Field trials will also be carried out to evaluate performance in the field.

EXAMPLE 6

Modulating Expression of GWD

Overexpression of GWD.

Overexpression of GWD in wheat or other plants requires the use of a cDNA or genomic DNA encoding GWD. For this, the protein coding region of the full length wheat cDNA sequence (SEQ ID NO: 2) can be used, operably joined to a promoter, which may be a heterologous promoter with respect to the GWD coding region.

Expression Levels of Genes Encoding GWD and PWD in Different Tissues and through Plant Development Quantitative reverse transcription-PCR (RT-PCR) assays are carried out on mRNA samples isolated from different plant tissues, in particular leaf and endosperm, throughout plant development to measure expression patterns of the GWD and PWD genes. Expression levels in leaves are measured every 3 hours through a 24 hour period to account for the circadian rhythm in expression levels, as has been described for the *C. reinhardtii* model (Ral et al., 2005). Phosphate content, starch content variation and alpha-amylase activity will be also monitored in the leaves to analyse transitory carbohydrate metabolism.

Endosperms have been collected from wild-type plants at various stages of development, and are used for the isolation of RNA to study the expression of GWD and PWD through the endosperm development by quantitative RT-PCR.

Multiple genotypes with similar amylopectin/amylose ratios have been selected for their particular physico-chemical properties. Some cultivars are empirically known to be relevant for baking and noodle making (Chara). Some are known to be good for Asian steamed bread (Baxter) and others for their sponge and dough bread baking properties (AC Barrie and Alsen).

EXAMPLE 7

Modulating Expression of GWD and PWD

Mutation of PWD in Rice.

The amino acid sequence of the PWD protein from *Arabidopsis thaliana* (NP_194176) was used as a query sequence to interrogate the rice Tos17 Insertion Mutant Database. Three different Tos17 lines (NG0294, ND9050_0_701_1A and T29717T) were identified and seed of these lines obtained. The tagged rice genomic sequences (SEQ ID Nos: 8 to 10) associated with these three insertions each displayed homology (about 75% identity) with the *Arabidopsis* PWD sequence, indicating that the insertions were within a rice PWD gene.

NG0294

(SEQ ID NO:8)
TGCTGGAGCAGCAGTATATGATAGGTTAGAGAAAGTCCGCCATAATTTTT

GTAGTTTGCTCAAGAATTTATTTGGCATTACAACTAAGCTGACTGCTTGT

TTCAGTGTCCCTATGGATGAGGAAGATGAAGTCGTACTCGACTACACCAC

AGACCCCTCATTACAGATCAGGGATCCAAAAATCAATCCTCTCGAGCAT

TGCACGGGCTGGTCATGCCATTGAGGATTTCTATGGGTCACCACAGGGCA

CAGGATTTTGAGGGTGCAGTGAAGGAAGGGAAGCTATAAGTAGTACAGAC

AAGACCACAAATGTAATCTATATGTATATTTTATAGCCAAGTCAATCAGG

AAATGTTGTAGAGTAAGATATACGGGCCGTGGGACATGTATAACACGTTA

TGCTCCTTTTTTT

ND9050_0_701_1A (SEQ ID NO: 9)
TCTACAACTACAACTTTTTAGAATCTGGACCAAAAGCTGGACTGTTTGAG

GGAGCTTCTGATTCTGAGAGAAGCTGCAGCAGCTAGAAGCTCCCCCAAAC

AGGCCCTTAGGTAGCTGGTTACAAGTCTGATCACACTGTTTTAGGTTTGT

CTGTTGTTGTATATCAGATAGCTAAATGCATAGCTGTGAGCTAGAGTTGT

GATAAACTGGAAATAGGTCAGGGAACGTCTTTTTTTGCCAAAGTATGGGT

AAAGATAAACTTGGTGAGCTCAGCTGGGGACAAAATCATCAGATTTTGTA

TTCTCCCAGCAGAGCAAATAGGGATTTGCCTGTGAGTGCATGCCTGACTT

GTCTGTTGGTCTATGAAATGGGCCGTGAAGTGTGCTTCTATGGGCCTTGT

CACTACTNACCAGGCGGTATTGCAGAGCAGATTTCTTGGCCCATTTTGTC

CTTTTTCTCTCT

T29717T (SEQ ID NO: 10)
CTTGGGAAGACGGTGCGTGTTAGATTTGTGCTGAAGAGGGAATGCACGIT

CGGCCAGAGCTTCCACCTTGTCGGCGACGACCCGGCGCTCGGCCTCTGGG

ATCCGTCGAAGGCAGTGCCTTTGGATTGGTCAGAAGGACACGACTGGACT

GTGGAGAAAGTGAGCCTTGCATCGTGCGCATTGTTTGATGTACTCTCCTT

TTGAGGTAATCATCACCCCTTTTCTTCTGTACAGGACTTGCCAGCCAACA

AGTTGATTGAGTACAAGTTCGTGCTGCAAGATTTGTCGGGCAAGTTGCAT

TGGCAGAATGGTCGTAATAGAAGCGTACAGACAGGTGAAACTGCAAACAT

TCTAGTCGTATATGAAGATTGGGGTAATGCAAATAGTCAGACAGTAGAAG

AGGAGGGTAAAGTGTCCATTGGGATGGAGGAGGGTAAATTGTCCGTTGGG

ATGGAGGAGGCTGTAGTTCCAGATGATAGTGAAAGCAGAG

Since these Tos17 insertional mutations were expected to be recessive, homozygous mutants were isolated for each of them. This first required the development of a screening method to distinguish homozygotes and heterozygotes for each of the wild-type and mutant alleles, to identify plants as wild type, heterozygous or homozygous mutant. This was accomplished as follows.

Two primer pairs were designed and produced for each line, see below. The Tos17primer used in each Primer pair A had a nucleotide sequence complementary to a sequence within the Tos17 element, therefore the element had to be present for amplification to occur. A positive PCR result using Primer pair A therefore identified the plant as having a mutant allele, while a negative PCR result for Primer pair A revealed the plant to be wild-type for the PWD gene. Each Primer pair B distinguished mutant lines that were heterozygous from those that were homozygous and confirmed the status of wild-types. Each Primer pair B flanked the Tos17 insert site. A negative PCR result for Primer couple B revealed the plant as homozygous mutant as the size of the predicted amplification product in the presence of Tos17 was so large it was not expected to amplify. A combination of two positive PCR results for both primer pairs distinguished the plant as heterozygous for wild-type and mutant alleles.

| Rice Tos17 Mutant | Primer pair A | Primer pair B |
|---|---|---|
| PWDI | Tos17primer & Tos17PWDI | HomoGWDfor & Tos17PWDII |
| PWDII | Tos17primer & Tos17PWDII | HomoGWDfor & Tos17PWDII |
| PWDIII | Tos17primer& Tos17PWDIII | HomoGWDfor & Tos17PWDIII |

| Primers | Sequences from 5' to 3' | |
|---|---|---|
| Tos17primer | ATTGTTAGGTTGCAAGTTAGTT | (SEQ ID NO: 15) |
| Tos17PWDI | CTTCCTTCCTTCACTGCAC | (SEQ ID NO: 16) |
| Tos17PWDII | GCAAGGCTCACTTTCTCCAC | (SEQ ID NO: 17) |

| Primers | Sequences from 5' to 3' | |
|---|---|---|
| Tos17PWDIII | TCCATCCCAATGGACACTTT | (SEQ ID NO: 18) |
| HomoPWDfor | TACGACATGGAAGCCG | (SEQ ID NO: 19) |

Using this method, homozygous mutant plants were identified for each of the three insertion lines. Seed from these plants were analysed using the methods described above for wheat, and sown under controlled conditions to test plant phenotypes. A slight reduction in starch phosphate content was seen in one insertion mutant compared to the wild-type variety Nipponbare, but it was unclear if there was a reduction compared to starch from a segregant from the line lacking the insertion, due to large error bars in the analysis. There was no significant difference in starch content, swelling index, λmax, chain length distribution or the level of α-amylase in flour samples from the grain of the insertional lines compared to the segregants lacking the insertion or wild type. These data suggested that there was no more than a slight effect from inactivating PWD alone, in rice. However, data from Baunsgaard et al. (2005) suggest that the combination of GWD and PWD in *Arabidopsis* shows increased effect compared to GWD alone.

Several other rice insertion lines were identified in the Origene database (orygenesdb.cirad.fr) which appeared to contain T-DNA insertions in a rice GWD gene. These were as follows:

3A-51160 corresponding to the FST A29424
3A-07997 corresponding to the FST A16348
2A-40470 corresponding to the FST A07158
3A-17981 corresponding to the FST A27803

These lines may be obtained from posTECH (Republic of Korea). Additionally, two lines were identified which appeared to have inserts in the rice SEX4 gene which encodes a starch phosphorylase: 1B-06142 corresponding to FST A3204, and 2D41347 corresponding to FST D08500. These will be analysed for the same properties as described above.

EXAMPLE 8

Further Mutants in GWD in Cereals

Genome Specific Primers for Wheat GWD Genes.

Genome specific primers were designed to amplify GWD gene fragments specifically from the A, B and D genomes, and thereby distinguish the three homologous genes in hexaploid wheat. This was achieved as follows. Several intron regions from the GWD gene from hexaploid wheat were amplified by PCR and the fragments cloned and sequenced. In most cases, three sequence variants could be identified, corresponding to the GWD genes from the A, B and D genomes, but not allowing the allocation of each variant to a particular genome. To achieve this allocation, the same PCR reactions were also carried out using, as template, genomic DNA from defined chromosome deletion lines, and the amplified fragments similarly cloned and sequenced. These lines contained GWD genes for only two of the genomes while the third was missing. For example, the chromosome deletion line N7At7B was null for chromosome 7A and therefore lacked the A genome GWD gene, but had 2 copies of the chromosome 7D GWD gene and 4 copies of the chromosome 7B GWD gene. Therefore, amplification of intron sequences from N7AT7B, N7BT7D and N7DT7A deletion lines allowed allocation of the sequence variants with each particular genome.

Fifteen cloned fragments were sequenced from each amplification, and unique genome specific modifications were thereby identified that correlated with the A, B and D genomes. For example the substitution of a C by a T was observed in the deletion line where the A genome was present but not in the A null line. This meant that the GWD sequence variant with a T was A genome specific. Such polymorphisms were then used to design the specific primer pairs as follows:

```
A genome:
Primer GWD1ForA*
5'-GAAACACATAGTCTG-3'        (SEQ ID NO: 20)

Primer IB_GWD2rev
5'-TTGCGGTGCCTTTACC-3'       (SEQ ID NO: 21)

B genome:
Primer GWD1ForB*_HTM
5'-GAAAGAAACACATAGTCTG-3'    (SEQ ID NO: 22)

Primer IB_GWD3rev
5'-ATCTGTAAACCTGTCTTGTG-3'   (SEQ ID NO: 23)

D genome:
Primer GWD2for2
5'-TTGCGGTGCCTTTACC-3'       (SEQ ID NO: 24)

Primer IB_GWD3rev
5'-ATCTGTAAACCTGTCTTGTG-3'   (SEQ ID NO: 25)
```

When these primer pairs were used in PCR reactions with wheat genomic DNA, using the following PCR cycling conditions: 94° C. for 5 min, then 40 cycles of 94° C. for 30 sec, 53° C. for 30 sec, 72° C. for 40 sec, followed by 72° C. 5 min, and the products fractionated by gel electrophoresis, the following amplification products could be distinguished: for the GWD gene on the A genome, a unique fragment of approximately 600 bp was observed, for the GWD gene on the B genome, a fragment of approximately 1000 bp, while for the GWD gene on the D genome, a fragment of approximately 500 bp was produced. The three PCR reactions could be combined into a single, multiplex PCR reaction using all three primer pairs, to allow high throughput screening of mutagenised seed and plant populations.

When these PCR reactions were repeated on wheat deletion lines with more limited, defined chromosomal deletions lacking specific chromosome segments, the lack of amplified products from certain deletion lines indicated that the GWD genes in wheat were located on the extremity of the short arm of chromosome 7, i.e. chromosome 7S.

Mutation of GWD Gene in Wheat.

Wheat seed of cv. Chara was mutagenised by heavy ion bombardment by a method essentially the same as that of shitsukawa et al., Genes Genet. Syst. 82:167-170 (2007). The mutagenised seed was grown to produce M1 plants, and the seed obtained from individual plants was harvested and maintained, thereby providing 8000 individual mutagenised lines.

The 8000 lines were screened using the genome specific primer pairs described above to identify mutants lacking any one of the three GWD genes. Two mutants were identified lacking the gene segment corresponding to the B genome GWD gene, and one mutant was identified lacking the D genome GWD gene segment. These mutant plants, which were presumed to be null mutants for the GWD genes, were grown in the greenhouse and appeared phenotypically normal. These plants will be crossed to produce the double mutants, lacking both the B and D genome GWD genes.

Further mutagenised lines are being examined to identify null mutants for the GWD gene on the A genome. When identified, such plants can be crossed with the B and D-genome double mutant to produce a triple mutant in each of the A, B and D genomes.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Summary of sequence identifiers

| SEQUENCE ID NO: | DESCRIPTION |
|---|---|
| 1 | Wheat genetic sequence corresponding to R1(potato) and PWD (*Arabidopsis*) |
| 2 | cDNA of Wheat GWD |
| 3 | Amino acid sequence encoded by SEQ ID NO: 2 |
| 4 | EST of Barley GWD |
| 5 | cDNA of wheat GWD-like gene |
| 6 | Forward primer for GWD gene |
| 7 | Reverse primer for GWD gene |
| 8 | Partial rice PWD insertion sequences |
| 9 | Partial rice PWD insertion sequences |
| 10 | Partial rice PWD insertion sequences |
| 11 | EST of *sorghum* GWD gene (Accession No BI245998) |
| 12 | EST of *sorghum* GWD gene (Accession No CF074015) |
| 13 | EST of *sorghum* GWD gene (Accession No EH406623) |
| 14 | EST of *sorghum* GWD gene (Accession No CD423248) |
| 15 | Primer for rice PWD gene |
| 16 | Primer for rice PWD gene |
| 17 | Primer for rice PWD gene |
| 18 | Primer for rice PWD gene |
| 19 | Primer for rice PWD gene |
| 20 | Primer for wheat GWD gene |
| 21 | Primer for wheat GWD gene |
| 22 | Primer for wheat GWD gene |
| 23 | Primer for wheat GWD gene |
| 24 | Primer for wheat GWD gene |
| 25 | Primer for wheat GWD gene |

TABLE 2

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 3

Exemplary and Preferred Amino Acid Substitutions

| Original Residue | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

TABLE 4

| | Peak | Trough | Breakdown | Final Visc | Setback | Peak Time | Pasting Temp |
|---|---|---|---|---|---|---|---|
| BW26 (parent) | 398.92 | 176.25 | 222.67 | 401.67 | 225.42 | 8.53 | 78.45 |
| rsGWD1-1H (control) | 429.67 | 181.92 | 247.75 | 427.58 | 245.67 | 8.47 | 65.45 |
| rsGWD1-1G | 365.17 | 167.25 | 197.92 | 340.25 | 173 | 8.53 | 81.45 |
| rsGWD3-1L (control) | 410.67 | 198.75 | 211.92 | 402.5 | 203.75 | 8.53 | 68.95 |
| rsGWD3-1A | 330.5 | 179.67 | 150.83 | 378.08 | 198.42 | 8.6 | 78.9 |
| rsGWD4-1 (control) | 425.5 | 166.33 | 259.17 | 365.58 | 199.25 | 8.47 | 66 |
| rsGWD4-1T | 355.42 | 191.58 | 163.83 | 381.67 | 190.08 | 8.53 | 81.4 |
| rsGWD4-1Q | 365.17 | 167.25 | 197.92 | 340.25 | 173 | 8.53 | 81.45 |
| rsGWD5-9A (control) | 411.42 | 199 | 212.42 | 406.25 | 207.25 | 8.6 | 77.4 |
| rsGWD5-9X | 412.25 | 197.83 | 214.42 | 400.33 | 202.5 | 8.6 | 78.35 |

TABLE 5

Seed parameters for T2 seed from transgenic and control (wt) plants

|  | Seed Weight (mg) | | Seed production (g per plant) |
|---|---|---|---|
|  | Mean | standard deviation |  |
| BW26 (parental) | 37.54 | 2.52 | 16 |
| GWD1-1 H (wt) | 41.98 | 2.71 | 12 |
| GWD1-1 F | 46.45 | 6.68 | 27.5 |
| GWD1-1 G | 45.10 | 3.60 | 25 |
| GWD3-1 L (wt) | 44.00 | 3.96 | 14 |
| GWD3-1 A | 46.71 | 3.90 | 27.5 |
| GWD3-1 C | 46.13 | 4.57 | 24 |
| GWD3-1 D | 44.81 | 3.26 | 20 |
| GWD4-1 E (wt) | 46.51 | 3.76 |  |
| GWD4-1 A | 44.64 | 5.67 | 18.5 |
| GWD4-1 P | 42.20 | 3.65 |  |
| GWD4-1 Q | 49.89 | 3.22 | 20 |
| GWD4-1 T | 60.30 | 2.14 |  |
| GWD5-9 A (wt) | 43.83 | 4.90 | 10 |
| GWD5-9 X | 45.58 | 5.03 | 24 |

TABLE 6

|  | Leaf area (cm$^2$) | | Heads per plant | Seed production | | Seed weight | |
|---|---|---|---|---|---|---|---|
|  | 2 leaves stage | 4 leaves stage |  | g per plant | g per head | (g per 100 seeds) | Starch content (%) |
| BW26 (parent) | 4.4 ± 0.4 | 48.4 ± 6.9 | 5.8 ± 1.9 | 9.0 ± 2.1 | 1.3 ± 0.2 | 3.4 ± 0.4 | 64.4 ± 2.6 |
| rsGWD 1-1G | 6.5 ± 1.1 | 76.8 ± 10.2 | 9.8 ± 1.48 | 15.3 ± 2.7 | 1.8 ± 0.2 | 4.9 ± 0.3 | 59.6 ± 2.4 |
| rsGWD 3-1A | 6.6 ± 0.4 | 82.0 ± 5.6 | 8.2 ± 1.64 | 11.5 ± 3.7 | 1.7 ± 0.2 | 4.6 ± 0.3 | 65.6 ± 3.4 |
| rsGWD 3-1C | 7.9 ± 1.0 | 87.8 ± 6.7 | 8.4 ± 1.67 | 11.9 ± 1.5 | 1.6 ± 0.2 | 4.8 ± 0.3 | 67.4 ± 4.8 |
| rsGWD 4-1A | 6.4 ± 1.3 | 77.9 ± 13.8 | 8 ± 1.22 | 10.6 ± 2 | 1.6 ± 0.1 | 4.3 ± 0.2 | 66.2 ± 3.5 |
| rsGWD 5-9X | 7.1 ± 0.5 | 82.9 ± 12.6 | 8.2 ± 1.48 | 12.7 ± 2.8 | 1.7 ± 0.1 | 4.5 ± 0.2 | 65.7 ± 3.9 |
| rsGWD 5-9A (Ctrl) | 4.8 ± 0.6 | 58.2 ± 4.5 | 7.25 ± 1.5 | 10.9 ± 1 | 1.5 ± 0.1 | 4.0 ± 0.2 | 67.9 ± 2.3 |
| rsGWD 3-1L (control) | 5.1 ± 0.5 | 59.9 ± 5.6 | 7.2 ± 0.83 | 9.9 ± 1.4 | 1.3 ± 0.1 | 3.9 ± 0.1 | 63.9 ± 1.6 |

TABLE 7

Exon/intron structure of wheat GWD gene in comparison to rice gene.

| Wheat exon No. | Exon Wheat from nt | to nt | Wheat exon size (bp) | Rice gene exon position from nt | to nt | Rice Intron No. | Rice intron size (bp) |
|---|---|---|---|---|---|---|---|
| Exon 1 | 1 | 328 | 328 | 1713 | 2032 | Intron 1 | 89 |
| Exon 2 | 342 | 417 | 76 | 2122 | 2197 | Intron 2 | 114 |
| Exon 3 | 434 | 527 | 94 | 2312 | 2405 | Intron 3 | 81 |
| Exon 4 | 531 | 670 | 140 | 2487 | 2626 | Intron 4 | 590 |
| Exon 5 | 662 | 761 | 100 | 3217 | 3316 | Intron 5 | 78 |
| Exon 6 | 758 | 903 | 146 | 3395 | 3540 | Intron 6 | 229 |
| Exon 7 | 896 | 1059 | 164 | 3770 | 3933 | Intron 7 | 86 |
| Exon 8 | 1058 | 1150 | 93 | 4020 | 4112 | Intron 8 | 91 |
| Exon 9 | 1157 | 1336 | 180 | 4204 | 4383 | Intron 9 | 943 |
| Exon 10 | 1334 | 1399 | 66 | 5327 | 5392 | Intron 10 | 73 |
| Exon 11 | 1397 | 1462 | 66 | 5466 | 5531 | Intron 11 | 83 |
| Exon 12 | 1465 | 1522 | 58 | 5615 | 5672 | Intron 12 | 212 |
| Exon 13 | 1520 | 1674 | 155 | 5885 | 6039 | Intron 13 | 117 |
| Exon 14 | 1673 | 1759 | 87 | 6157 | 6243 | Intron 14 | 816 |
| Exon 15 | 1756 | 1934 | 179 | 7060 | 7238 | Intron 15 | 81 |
| Exon 16 | 1942 | 2042 | 101 | 7320 | 7420 | Intron 16 | 64 |
| Exon 17 | 2041 | 2258 | 218 | 7485 | 7702 | Intron 17 | 81 |
| Exon 18 | 2254 | 2361 | 108 | 7784 | 7891 | Intron 18 | 683 |
| Exon 19 | 2384 | 2501 | 118 | 8575 | 8692 | Intron 19 | 126 |
| Exon 20 | 2499 | 2626 | 128 | 8819 | 8946 | Intron 20 | 362 |
| Exon 21 | 2624 | 2738 | 115 | 9309 | 9423 | Intron 21 | 176 |
| Exon 22 | 2740 | 2837 | 98 | 9600 | 9697 | Intron 22 | 296 |
| Exon 23 | 2834 | 3105 | 272 | 9994 | 10265 | Intron 23 | 68 |
| Exon 24 | 3101 | 3218 | 118 | 10334 | 10451 | Intron 24 | 79 |
| Exon 25 | 3217 | 3435 | 219 | 10531 | 10749 |  |  |

BIBLIOGRAPHY

Abel et al., *The Plant Journal* 10: 981-991, 1996
Adams et al., *Anal. Biochem.,* 266: 77-84, 1999
Almeida and Alishire, *Trends Cell Biol* 15: 251-258, 2005
Altschul et al., *Nucl. Acids Res.* 25: 3389, 1997
An, *Methods in Enzymology,* 153: 292, 1987
Ausubel (Ed) *Current Protocols in Molecular Biology,* 5$^{th}$ Edition, John Wiley & Sons, Inc, NY, 2002
Ausubel et al. eds., *Current Protocols in Molecular Biology,* John Wiley and Sons, New York, 1990
Ausubel et al., (eds.), *Current Protocols in Molecular Biology,* John Wiley & Sons, NY, 6.3.1-6.3.6., 1989
Ausubel et al., *Current Protocols in Molecular Biology John Wiley* & Sons Inc, Chapter 15, 1994-1998
Baba et al., *Biochem Biophys Res Commun* 181: 87-94, 1991
Banks et al. *Starch/die Starke,* 23: 118-124, 1971
Barker et al., *Plant Mol. Biol.,* 2: 235-350, 1983
Batey et al., *J. Sci. Food Agric.* 74: 503-508, 1997
Baunsgaard et al., *The Plant Journal* 41, 595-605, 2005
Bechtold et al., *C.R. Acad. Sci. Paris,* 316: 1194, 1993
Bevan et al., *Nucl. Acid Res.,* 11: 369, 1983
Birch, *Ann Rev Plant Physiol Plant Mol Biol* 48: 297-326, 1997
Blennow et al., *Int. J. Biol. Macromol.* 27: 211-218, 2000a
Blennow et al., *Carbohydr. Polym.* 41: 163-174, 2000b
Bonner et al., *Eur. J. Biochem.,* 46: 83, 1974
Bourque *Plant Sci.* 105: 125-149, 1995
Bower et al., *Molec. Breed.,* 2: 239-249, 1996
Boyer and Preiss, *Carbohydrate Research* 61: 321-334, 1978
Buléon et al., *International Journal of Biological Macromolecules,* 23: 85-112, 1998
Cao et al. *Plant Cell Reporter,* 11: 586-591, 1992
Cao et al., *Archives. of Biochemistry and Biophysics.* 373: 135-146, 2000

Chamberlain et al., *Aust. J. Plant Physiol.*, 21: 95-112, 1994
Christensen et al., *Transgen. Res.*, 5: 213-218. 1996
Comai et al., *Plant J* 37: 778-786, 2004
Craig et al., *Plant Cell* 10: 413-426, 1998
De Framond, *Biotechnology*, 1: 262, 1983
Deikman et al., *EMBO J.*, 2: 3315-3320, 1998
DellaPenna et al., *Plant Cell*, 1: 53-63, 1989
Dellaporta et al., in *Chromosome Structure and Function*, pp. 263-282, 1988
Delrue et al., *Journal of Bacteriology*, 174: 3612-3620, 1992
Delvalle et al., *Plant J* 43: 398-412, 2005
Denyer et al., *Plant Physiology* 112: 779-785, 1996
Eagles et al., *Aust. J. Agric. Res.* 52: 1 349-1356, 2001
Ehrlich, *Proc. Natl. Acad. Sci. USA*, 75: 1433, 1978
Ekman and Jager, *Anal Biochem* 214: 138-141, 1993
Erickson et al., *Science*, 249: 527-533, 1990
Fergason, *Speciality Corns eds, CRC Press Inc.* pp 55-77, 1994
Fisher et al., *Plant Physiol* 102: 1045-1046, 1993
Fromm et al., *Proc. Natl. Acad. Sci., U.S.A*, 82: 5824, 1985
Gao et al., *Plant Physiol* 114: 69-78, 1997
Gao et al., *Plant Cell* 10: 399-412, 1998
Garfinkel et al., *Cell*, 27: 143-153, 1983
Gordon-Kamm, *Plant Cell*, 2: 603-618, 1990
Greve, *Mol. Appl. Genet.*, 1: 499-511, 1983
Harayama, *Trends Biotechnol* 16: 76-82, 1998
Hartmann and Endres, *Manual of Antisense Methodology*, Kluwer, 1999
Haseloff and Gerlach, *Nature* 334: 585-591, 1988
Hedman and Boyer, *Biochemical Genetics* 20: 483-492, 1982
Hendrix et al., *J. Insect Physiol.*, 47: 423-432, 2001
Henikoff et al., *Plant Physiol* 135: 630-636, 2004
Hinchee et al., *Biotech.*, 6: 915, 1988
Hodgson, *Bio/Technology*, 9: 19-21, 1991
Hoekema et al., *Nature*, 303: 179, 1983
Horsch et al., *Science*, 227: 1229, 1985
Ikuta et al., *Biotech.*, 8: 241, 1990
James et al., *Plant Cell* 7: 417-429, 1995
Jobling et al., *Plant Journal* 18: 163-171, 1999
Joshi, *Nucl. Acid Res.*, 15: 6643, 1987
Katz et al., *J. Gen. Microbiol.*, 129: 2703, 1983
Klee et al., *Annual Review of Plant Physiology*, 38: 467, 1987
Klein et al., *Nature* 327: 70, 1987
Konik-Rose et al., *Starch/die Stärke* 53: 14-20, 2001
Kotting et al., *Plant Physiology* 137 pp 242-252, 2005
Kubo et al., *Plant physiology.* 121: 399-409, 1999
Kurrek, *Eur. J. Biochem.*, 270: 1628-1644, 2003
Langridge et al., *Aust. J. Agric. Res.* 52: 1043-1077, 2001
Lee, *Plant Mol. Biol.*, 13: 21-30, 1989
Lemieux, *Current Genomics* 1: 301-311, 2000
Li et al., *Plant Physiology* 123: 613-624, 2000
Li et al., *Plant physiology.* 120: 1147-1155, 1999a
Li et al., *Theoretical and Applied Genetics* 98: 1208-1216, 1999b
Li et al., *Funct Integr Genomics* 3: 76-85, 2003
Liu et al., *J. Am. Chem. Soc.* 118: 1587-1594, 1996
Lorberth et al., *Nat. Biotechnol.* 16: 473-477, 1998
Maas et al., *Mol Breeding*, 3: 15-28, 1997
Marmur et al., *J. Mol. Biol.*, 5: 109, 1962
McPherson and Moller (Ed), BIOS Scientific Publishers Ltd, Oxford, 2000
Medberry et al., *Plant Cell* 4: 185-192, 1992
Medberry et al., *Plant J.* 3: 619-626, 1993
Millar and Waterhouse, *Funct Integr Genomics* 5: 129-135, 2005
Mizuno et al., *Journal of Biochemistry* 112: 643-651, 1992
Morrison and Laignelet, *Journal of Cereal Science* 1: 9-20, 1983
Myers et al., *Plant Physiology* 122: 989-997, 2000
Nair et al., *Plant Sci* 122: 153-163, 1997
Nakamura and Yamanouchi, *Plant Physiol* 99: 1265-1266, 1992
Needleman and Wunsch, *J. Mol. Biol.* 48: 443-453, 1970
Niedz et al., *Plant Cell Reports,* 14: 403, 1995
Ow et al., *Science,* 234: 856, 1986
Pasquinelli et al., *Curr Opin Genet Develop* 15: 200-205, 2005
Perriman et al., *Gene* 113: 157-163, 1992
Plasterk et al., *Current Opinion in Genetics and Dev.,* 10: 562-67, 2000
Potrykus et al., *Mol. Gen. Genet.,* 199: 183, 1985
Prasher et al., *Biochem. Biophys. Res. Comm.,* 126: 1259, 1985
Rahman et al., *Genome* 40: 465-474, 1997
Ral et al., *Plant Phys.* 142: 305-317, 2006
Reddy et al., *Theor. Appl. Genet.,* 85: 616-624, 1993
Remington's Pharmaceutical Sciences, $18^{th}$ Ed., Mack Publishing, Company, Easton, Pa., U.S.A., 1990
Repellin et al., *Plant Gene Reg pp.* 97-094, 1997
Ritte et al., *FEBS* pp. 4872-4876, 2006
Robinson, *The Organic Constituents of Higher Plants*, Cordus Press, North Amherst, USA, 1980
Salomon et al., *EMBO J.,* 3: 141-146, 1984
Sambrook et al *Molecular Cloning: A Laboratory Manual* (2nd ed.). Cold Spring Harbour Laboratory, Cold Spring Harbour, N.Y., 1989
Sambrook, *Molecular Cloning: A Laboratory Manual,* $3^{rd}$ Edition, CSHLP, CSH, NY, 2001
Schulman and Kammiovirta, *Starch* 43: 387-389, 1991
Schwall et al., *Nature Biotechnol.* 18: 551-554, 2000
Senior, *Biotech. Genet. Engin. Revs.* 15: 79-119, 1998
Sharp et al., *Aust J Agric Res* 52: 1357-1366, 2001
Shimamoto et al., *Nature* 338: 274-276, 1989
Shippy et al., *Mol. Biotech.* 12: 117-129, 1999
Shitsukawa et al., *Genes Genet. Syst.* 82: 167-170, 2007
Slade and Knauf, *Transgenic Res* 14: 109-115, 2005
Smith et al., *Nature* 407: 319-320, 2000
Sooknanan et al., *Biotechniques* 17: 1077-1080, 1994
Stalker et al., *Science,* 242: 419, 1988
Summerton et al., *Antisense and Nucleic acid Drug Development,* 7: 187-195, 1997
Sun et al., *The New Phytologist* 137: 215-215, 1997
Sutcliffe, *Proc. Natl. Acad. Sci. USA,* 75: 3737,
Takeda et al., *Carbohydrate Research* 240: 253-262, 1993a
Takeda et al., *Carbohydrate Research* 246: 273-281, 1993b
Thillet et al., *J. Biol. Chem.,* 263: 12500, 1988
Thompson et al., *Carbohydrate Res.,* 331: 149-161, 2001
Thorbjornsen et al., *Plant Journal* 10: 243-250, 1996
Tingay et al., *Plant J.* 11: 1369-1376, 1997
Tyagi et al., *Proc. Natl. Acad. Sci. USA,* 93: 5395-5400, 1996
Vain et al., *Plant Cell Reporter,* 12: 84-88, 1993
Vasil, *Bio/Technol.* 8: 429-434, 1990
Veronese et al., *Enz. Microbial Tech.,* 24: 263-269, 1999
Viksø-Nielsen et al., *Biomacromolcules* 3: 836-841, 2001
Viksø-Nielsen et al., *Carbohydr. Res.* 337, pp. 327-333, 2001
Vogel et al., Fermentation and Biochemical Engineering Handbook: *Principles, Process Design, and Equipment,* Noyes Publications, Park Ridge, N.J., USA, 1996
Wan and Lemaux, *Plant Physiol.* 104: 37-48, 1994

Waterhouse et al., *Proc. Natl. Acad. Sci. USA* 95: 13959-13964, 1998
Wells, *Methods Enzymol.*, 202: 2699-2705, 1991
Yu et al., *Plant Cell* 13: 1907-1918, 2001
Zeeman et al., *New Phytologist* 163: 247-261, 2004
Zeeman et al., *Plant Journal* 15: 357-365, 1998
Zukowsky et al., *Proc. Natl. Acad. Sci. USA*, 80: 1101, 1983
Zwar and Chandler, *Planta* 197: 39-48, 1995

The invention claimed is:

1. A process for producing grain comprising
(i) growing a plurality of at least 10 cereal plants, which are each homozygous for an RNA-encoding transgene inserted in their genome which reduces the level of endogenous glucan water dikinase (GWD) in the endosperm of the grain of the plants compared to endosperm of grain of corresponding wild-type plants, (ii) identifying from the plurality of at least 10 cereal plants one or more plants which produce grain which if germinated give rise to progeny plants having increased seedling vigor relative to wild-type grain, (iii) obtaining grain of the one or more plants identified in step (ii), thereby producing grain which if germinated give rise to progeny plants having increased seedling vigor.

2. The process of claim 1, wherein the plants further comprise a reduced expression of phosphoglucan, water dikinase (PWD).

3. The process of claim 1, wherein the plants are further characterized by an increased level of expression of an endogenous α-amylase in the grain of the plants compared to the corresponding wild-type grain.

4. The process of claim 1, wherein the harvested grain comprises starch which has a level of glucose-6-phosphate in the starch of less than 10ng/mg starch, has a starch phosphate content of less than 0.02%, or has a starch phosphate content reduced by at least 50% relative to starch from the corresponding wild-type grain.

5. The process of claim 1, wherein the plants are wheat.

6. The process of claim 1, wherein the plants are corn, barley, rice or sorghum.

7. The process of claim 1, wherein the plants are further characterized by increased biomass, vigor, germination, seedling vigor, growth rate, height, total leaf area, photosynthetic rate per leaf area, number of leaves per plant, number of heads per plant, number of tillers per plant, number of seeds per plant, number of seeds per head, average grain weight, grams of grain per plant, starch content of grain, stem thickness, number of internodes, number of branches, number of flowers, flower size or shape, flower color, root mass, number of roots, length of roots, and/or yield and/or delayed senescence compared to a corresponding wild-type plant.

8. The process of claim 3, wherein the level of amylase activity in flour obtained from the grain is at least 4 units/g flour.

9. The process of claim 1, wherein the level of GWD is preferentially reduced in the endosperm of the cereal plants relative to tissues or organs in the cereal plants other than the endosperm.

10. The process of claim 1, wherein the cereal plants are further characterized by a modified level of endogenous glycosylase, such that the digestibility by an animal of at least one part of the plant is increased compared to the wild-type cereal plant.

11. The process of claim 1, wherein the cereal plants identified in step (ii) are characterized by increased seedling vigor and further characterized by one or more of increased biomass, growth rate, total leaf area, number of grain per plant, average grain weight per plant, number of tillers per plant, number of heads per plant, number of grain per head, starch content of grain, and delayed senescence compared to the corresponding wild-type cereal plant.

12. The process of claim 1, wherein (a) the RNA molecule encoded by the transgene comprises at 30 contiguous nucleotides which are identical in sequence to 30 contiguous nucleotides of the complement of an mRNA encoded by a gene encoding the endogenous GWD in the plurality of at least 10 cereal plants; or (b) wherein the RNA molecule encoded by the transgene is a microRNA which comprises 21 contiguous nucleotides of the complement of the mRNA.

13. Cereal grain produced by the process of claim 1 from a plurality of at least 10 cereal plants, the grain being homozygous for an RNA-encoding transgene inserted in their genome which reduces the level of endogenous glucan water dikinase (GWD) in the endosperm of the cereal plants compared to corresponding endosperm of wild-type cereal plants, the cereal grain comprising a reduced level of endogenous glucan water dikinase (GWD) compared to corresponding wild-type cereal grain, wherein the cereal grain, if germinated, gives rise to progeny plants having increased seedling vigor relative to the corresponding wild-type cereal grain.

14. The cereal grain of claim 13, wherein the level of GWD is preferentially reduced in the endosperm of the cereal plants relative to tissues or organs in the cereal plants other than the endosperm.

15. The cereal grain of claim 13, comprising starch which has a level of glucose-6-phosphate in the starch of less than 10 ng/mg starch, has a starch phosphate content of less than 0.02%, or has a starch phosphate content reduced by at least 50% relative to starch from the cereal grain of the corresponding wild-type cereal plant.

16. The cereal grain of claim 13, wherein (a) the RNA molecule encoded by the transgene comprises 30 contiguous nucleotides which are identical in sequence to 30 contiguous nucleotides of the complement of an mRNA encoded by a gene encoding the endogenous GWD in the plurality of at least 10 cereal plants; or (b) wherein the RNA molecule encoded by the transgene is a microRNA which comprises 21 contiguous nucleotides of the complement of the mRNA.

17. Processed grain, flour, wholemeal, or at least partly purified starch produced from the grain of claim 13, wherein the processed grain, flour, wholemeal, or at least partly purified starch comprises the RNA-encoding transgene.

18. A process for producing a food product, comprising mixing the grain of claim 13 or processed grain, flour, wholemeal, or at least partly purified starch therefrom which comprises the RNA-encoding transgene with another food ingredient and optionally cooking, baking, frying, steaming, boiling, extruding or otherwise processing the mixture.

19. A process for feeding a human or animal, comprising providing the grain of claim 13 or processed grain, flour, wholemeal, or at least partly purified starch therefrom to the human or animal, wherein the processed grain, flour, wholemeal, or at least partly purified starch comprises the RNA-encoding transgene.

20. A cereal plant produced from the grain of claim 13, wherein the plant is characterized by increased seedling vigor and one or more of increased biomass, growth rate, total leaf area, number of grain per plant, average grain weight per plant, number of tillers per plant, number of heads per plant, number of grain per head, starch content of grain, and delayed senescence compared to a corresponding wild-type cereal plant.

21. A plurality of at least 10 cereal plants, which are each homozygous for an RNA-encoding transgene inserted in their genome which reduces the level of endogenous glucan water dikinase (GWD) in the endosperm of the grain of the cereal plants compared to endosperm of grain of corresponding wild-type cereal plants and wherein the grain of each cereal plant, if germinated, gives rise to progeny plants having increased seedling vigor relative to the grain of the corresponding wild-type cereal plants.

22. The plurality of cereal plants of claim 21, wherein the level of GWD is preferentially reduced in the endosperm of the cereal plants relative to tissues or organs in the cereal plants other than the endosperm.

23. The plurality of cereal plants of claim 21, wherein the plants further comprise an increased level of expression of an endogenous α-amylase in the grain of the plant compared to the corresponding wild-type cereal grain.

24. The plurality of cereal plants of claim 21, wherein grain harvested from the plants comprises starch which has a level of glucose-6-phosphate in the starch of less than 10 ng/mg starch, has a starch phosphate content of less than 0.02%, or has a starch phosphate content reduced by at least 50% relative to starch from the corresponding wild-type cereal grain.

25. The cereal plants in the plurality of cereal plants of claim 21, which are wheat.

26. The cereal plants in the plurality of cereal plants of claim 21, which are corn, barley, rice or sorghum.

27. The plurality of cereal plants of claim 21, wherein the plants are characterized by increased seedling vigor and further characterized by one or more of increased biomass, germination, growth rate, height, total leaf area, photosynthetic rate per leaf area, number of leaves per plant, number of heads per plant, number of tillers per plant, number of grain per plant, number of grain per head, average grain weight, grams of grain per plant, starch content of grain, stem thickness, number of internodes, number of branches, root mass, number of roots, length of roots, and delayed senescence compared to a corresponding wild-type plant.

28. The plurality of cereal plants of claim 21, wherein the plants further comprise a modified level of endogenous glycosylase, such that the digestibility by an animal of at least one part of each plant is increased relative to the wild-type cereal plant.

29. The plurality of cereal plants of claim 21, wherein the plants are characterized by increased seedling vigor and further characterized by one or more of increased biomass, growth rate, total leaf area, number of grain per plant, average grain weight per plant, number of tillers per plant, number of heads per plant, number of grain per head, starch content of grain, and delayed senescence compared to a corresponding wild-type cereal plant.

30. The plurality of cereal plants of claim 21, wherein (a) the RNA molecule encoded by the transgene comprises 30 contiguous nucleotides which are identical in sequence to 30 contiguous nucleotides of the complement of an mRNA encoded by a gene encoding the endogenous GWD in the plurality of at least 10 cereal plants; or (b) wherein the RNA molecule encoded by the transgene is a microRNA which comprises 21 contiguous nucleotides of the complement of the mRNA.

* * * * *

SEQUENCE LISTING

<160> NUMBER OF SEQ ID NOS: 25

<210> SEQ ID NO 1
<211> LENGTH: 2273
<212> TYPE: DNA
<213> ORGANISM: Triticum aestivum
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (771)..(775)
<223> OTHER INFORMATION: n is a, c, g, or t

<400> SEQUENCE: 1

```
ggtgaaggtt tcatggttgg tgttcaaatc aacccggtga atggtttatc atctggtttt      60
cctgatttgc ttcaatttgt gcttgaccat gttgaggata aatcagcaga gccacttctt     120 gagggttat tggaggctcg tgttgaacta cgcccttgc tcattggctc atctgaacgc      180
ttgaaggatc ttatcttttt ggacattgct cttgattcta ctttcaggac agcagttgaa     240
aggtcgtatg aggagctgaa tgatgcagca ccggagaaaa ttatgtactt catcagtctt     300
gttcttgaaa atcttgcctt gtcnactgac gacaacgaag acatcttata ttgcttaaag    360
ggatggaatc gagccatgga catggttaag caaaaggatg accaatgggc cctctacgct     420
aaagcatttc ttgacagaac cagacttgcc cttgcgagca agggcgaaca atactacaat     480
atgatgcagc cctcggctga atatcttggc tcattactca acgttgagga atgggcagtt     540
gacatcttca cagaagaagt aattcgtggt ggatcagcta ccactttatc tgctcttctg     600
aaccgatttg accctgttct cagaaatgtc gcacaccttg gaagttggca ggttattagc     660
ccagttgaag taacaggtta tattgtagtg gttgataagt tgctttctgt tcaaaacaaa     720
acttatgata aaccaacaat ccttgtggca aagagtgtca agggagagga nnnnntacca     780
gatggtgttg ttggcgtgat aacacctgat atgccagatg ttctgtctca tgtgtcagtt     840
cgagcaagga attgcaaggt gttgtttgcg acatgctttg acctgaacat cctgtctgaa     900
cttcaaggac atgaagggaa ggtgttttcc ttcaaaacta cttctgcaga tgtcacctac     960
agggaggtat cggacagtga actttcaatt tcttcagatg cacaaggtgg tgaagcaata    1020
ccatctttat cattagtcaa gaaaaagttc ctcggaaaat atgcaatatc agcggaagag    1080
ttctctgatg aaatggttgg agcaaagtcc cgcaacatag catacctgaa aggaaaagta    1140
ccttcatggg ttggtatccc aacatcagtt gccataccat ttgggacctt tgagaagata    1200
ttgtctgatg agaccaataa ggaagtagca caaaacatac agatgctgaa gggcagactt    1260
gctcaagaag attttagtgc tctaggagaa atccggaaaa ctgttcttaa tctaactgct    1320
ccaactcaac cggttaagga gctgaaggag aagatgctaa gctccggaat gccctggcct    1380
ggagatgaaa gtgaccaccg ttgggagcaa gcatggatgg caattaaaaa ggtttgggca    1440
tcaaaatgga atgaaagagc atactttagt acacgcaagg tgaagctcga tcatgagtac    1500 cttccatgg ctgttcttgt acaagaaatt gtcaacgcag actatgcctt tgtcattcat    1560
actacgaacc cgtcatctgg agattcttct gagatatatg ctgaagtggt gaaggacttg    1620
ggagagacac ttgtgggagc ttatcctggc cgtgccatga gcttcgtgtg taagaaagat    1680
```

| | |
|---|---:|
| gaccttgact ctcccaaggt actgggttac cctagcaagc caattggtct cttcataaag | 1740 |
| cggtcaatca tcttccgctc agactctaat ggtgaggatc tggaaggtta cgctggagca | 1800 |
| gggctgtatg atagtgtccc tatggatgtg aagatgaag ttgtactcga ctacacgacc | 1860 |
| gaccctctca tcactgactc tggattccgg agctcaatcc tctcaagcat tgcacgggct | 1920 |
| ggccacgcca ttgaggagct ctatgggtca ccgcaggatg ttgagggagt agtgaaggat | 1980 |
| gggaagatct acgtagtcca gacaagacca cagatgtaat atgtatgtat aggcagctca | 2040 |
| agctgtagag tagtaggata tgtggtcctt gctggcatgt atagccctac tcatagatgc | 2100 |
| acaacaaatc tacgttgtta tttatttgca tatacgctca gaataagctt tgatcacata | 2160 |
| ctgtatttcc tagagtacca gaacatgtat gcacgatcag gaatatgacc ttattaaaaa | 2220 |
| catcggggga gaacgttttg agcaatctat atttacacgt gccctataa tgt | 2273 |

<210> SEQ ID NO 2
<211> LENGTH: 3677
<212> TYPE: DNA
<213> ORGANISM: Triticum aestivum

<400> SEQUENCE: 2

| | |
|---|---:|
| ggaagaagga aggaactgca ggctgagttg ataatggag cctcagttga tcaattaagg | 60 |
| aagaaaattg tgaaaggaaa ccttgaaaag aaagtttcca agcaactgga gaagaagaag | 120 |
| tacttctcag tagaaaggat tcagcgcaga acagagata tcacgcaact tcttaataaa | 180 |
| cataagcctg tggttacaga acagcaagta aaagctgcac ccaaacagcc aactgttttg | 240 |
| gatctcttca caaagtcctt gcaagagggg gataactgtg acgtcctaag caggaagctt | 300 |
| ttcaagatcg gtgatgagga gatactggca attgccacaa atgctctagg taaaaccaga | 360 |
| gttcacttgg caacaaaccg tatggagcca cttattcttc actgggcact ggcaaaaaat | 420 |
| cccggagaat gggaggcacc tccttctagc atagtgcctt ctggctcaac agttctcgac | 480 |
| aaggcatgtg aaacttcatt cggtgagtct gaattggatg gtttgcaata ccaggttgtt | 540 |
| gagatagagc ttgatgacgg cagatacaag gggatgccct tgttctccg gcgtggtgaa | 600 |
| acatggataa agaacaacga ctctgacttc tatttggatt caacaccaa agttaccaag | 660 |
| aaatcaaagg atacgggtga tgccggtaaa ggcaccgcaa aggatttcct ggaaagaata | 720 |
| gcagatctgg aggaagatgc ccagcgatct tttatgcaca gatttaatat tgcggcggat | 780 |
| ctagttgacc aagccagaga tgctggacta ttgggtatcg ttggactttt tgtttggatt | 840 |
| agattcatgt ctaccaggca actaatatgg aacaagaact acaatgtgaa accacgtgag | 900 |
| ataagccaag cacaagacag gtttacagat gaccttgaga atatgtacaa aagttaccca | 960 |
| cagtacagag agatcttaag aatgttattg tctgctgttg gtcgtggagg tgaaggtgat | 1020 |
| gttggtcagc gtatccgtga tgagatatta gtaatccaga gaaataatga ctgcaaaggt | 1080 |
| ggaattatgg aagaatggca ccagaaactg cacaacaata caagcccaga tgatgtagtc | 1140 |
| atatgccagg cgataattga ttatatcaag agcgatttcg atatcaacgt ttactgggac | 1200 |
| accttgaaca aaaatggcat aaccaaagaa cgactgttga gctatgatcg tgcaattcat | 1260 |
| tcagaaccaa aattcaggag tgaccagaaa gaggggttac tccgtgattt gggcaactat | 1320 |
| atgagaagcc tgaaggctgt gcactctggt gctgatcttg agtctgctat tgcgacatgt | 1380 |
| atgggataca aatcagaggg tgaaggtttc atggttggtg ttcaaatcaa cccggtgaat | 1440 |
| ggtttatcat ctggttttcc tgatttgctt caatttgtgc ttgaccatgt tgaggataaa | 1500 |

```
tcagcagagc cacttcttga ggggttattg gaggctcgtg ttgaactacg ccctttgctc      1560
actggctcat ctgaacgctt gaaggatctt atcttttggg acattgctct tgattctact      1620
ttcaggacag cagttgaaag gtcgtatgag gagctgaatg atgcagcacc ggagaaaatt      1680
atgtacttca tcagtcttgt tcttgaaaat cttgccttgt ccactgacga caacgaagac      1740
atcttatatt gcttaaaggg atggaatcga gccatggaca tggttaagca aaggatgac       1800
caatgggctc tctacgctaa agcatttctt gacagaacca gacttgccct tgcgagcaag      1860
ggcgaacaat actacaatat gatgcagccc tcggctgaat atcttggctc attactcaac      1920
gttgaggaat gggctgttga catcttcaca gaagaagtaa ttcgtggtgg atcagctgcc      1980
actttatctg ctcttctgaa ccgatttgac cctgttctca gaaatgtcgc acaccttgga      2040
agttggcagg ttattagccc agttgaagta acaggttata ttgtagtggt tgataagttg      2100
ctttctgttc aaaacaaaac ttatgataaa ccaacaatcc ttgtggcaaa gagtgtcaag      2160
ggagaggaag aaataccaga tggtgttgtt ggcgtgataa cacctgatat gccagatgtt      2220
ctgtctcatg tgtcagttcg agcaaggaat tgcaaggtgt tgtttgcgac atgctttgac      2280
ccgaataccc tgtctgaatt caaggacat gaagggaagg tgttttcctt caaaactact       2340
tctgcagatg tcacctacag ggaggtatcg gacagtgaac ttatgcagtc aagttcttca      2400
gatgcacaag gtggtgaagc aataccatct ttatcattag tcaagaaaaa gttccttgga      2460
aaatatgcaa tatcagcgga agagttctct gatgaaatgg ttggagcaaa gtcccgcaac      2520
atagcatacc tgaaaggaaa agtaccttca tgggttggta tcccaacatc agttgcgata      2580
ccatttggga cctttgagaa gatattgtct gatgagacca ataaggaagt agcacaaaac      2640
atacagatgc tgaagggcag acttgctcaa gaagatttta gtgctctagg agaaatccgg      2700
aaaactgttc ttaatctaac tgctccaact caaccggtta aggagctgaa ggagaagatg      2760
ctaagctccg gaatgccctg gcctggagat gaaagtgacc accgttggga gcaagcatgg      2820
atggcaatta aaaaggtttg gcatcaaaa tggaatgaaa gagcatactt tagtacacgc        2880
aaggtgaagc tcgatcatga gtacctttcc atggctgttc ttgtacaaga aattgtcaac      2940
gcagactatg cctttgtcat tcatactacg aacccgtcat ctggagattc ttctgagata      3000
tatgctgaag tggtgaaagg acttggagag acacttgtgg gagcttatcc tggccgtgcc      3060
atgagcttcg tgtgtaagaa agatgacctt gactctccca aggtactggg ttaccctagc      3120
aagccaattg gtctcttcat aaagcggtca atcatcttcc gctcagactc taatggtgag      3180
gatctggaag gttacgctgg agcagggctg tatgatagtg tccctatgga tgtggaagat      3240
gaagttgtac tcgactacac gaccgaccct ctcatcactg actctggatt ccggaactca      3300
atcctctcaa gcattgcacg ggctggccac gccatcgagg agctctatgg gtcaccacag      3360
gatgttgagg gagtagtgaa ggatgggaag atctacgtag tccagacatg accacagatg      3420
taatatgtat gtatacgcgg ctcaagttgt agagtagtag gatatgtggt ccttgctggc      3480
atgtatagtt ctactcatag atgcacaaca catctacgtt gttatttatt tgcatatacg      3540
ctcagaataa gctttgatca catactgtat ttcctagagt accagaacat gtatgcacga      3600
tcaggaatat gaccttatta aaaacatcgg gggagaacgt tttgagcaat ctatatttac      3660
acgtgcccct ataatgt                                                     3677

<210> SEQ ID NO 3
<211> LENGTH: 1009
<212> TYPE: PRT
<213> ORGANISM: Triticum aestivum
```

<400> SEQUENCE: 3

```
Met Glu Pro Leu Ile Leu His Trp Ala Leu Ala Lys Asn Pro Gly Glu
1               5                   10                  15

Trp Glu Ala Pro Pro Ser Ser Ile Val Pro Ser Gly Ser Thr Val Leu
            20                  25                  30

Asp Lys Ala Cys Glu Thr Ser Phe Gly Glu Ser Glu Leu Asp Gly Leu
        35                  40                  45

Gln Tyr Gln Val Val Glu Ile Glu Leu Asp Asp Gly Arg Tyr Lys Gly
    50                  55                  60

Met Pro Phe Val Leu Arg Arg Gly Glu Thr Trp Ile Lys Asn Asn Asp
65                  70                  75                  80

Ser Asp Phe Tyr Leu Asp Phe Asn Thr Lys Val Thr Lys Ser Lys
                85                  90                  95

Asp Thr Gly Asp Ala Gly Lys Gly Thr Ala Lys Asp Phe Leu Glu Arg
            100                 105                 110

Ile Ala Asp Leu Glu Glu Asp Ala Gln Arg Ser Phe Met His Arg Phe
        115                 120                 125

Asn Ile Ala Ala Asp Leu Val Asp Gln Ala Arg Asp Ala Gly Leu Leu
    130                 135                 140

Gly Ile Val Gly Leu Phe Val Trp Ile Arg Phe Met Ser Thr Arg Gln
145                 150                 155                 160

Leu Ile Trp Asn Lys Asn Tyr Asn Val Lys Pro Arg Glu Ile Ser Gln
                165                 170                 175

Ala Gln Asp Arg Phe Thr Asp Asp Leu Glu Asn Met Tyr Lys Ser Tyr
            180                 185                 190

Pro Gln Tyr Arg Glu Ile Leu Arg Met Leu Leu Ser Ala Val Gly Arg
        195                 200                 205

Gly Gly Glu Gly Asp Val Gly Gln Arg Ile Arg Asp Glu Ile Leu Val
    210                 215                 220

Ile Gln Arg Asn Asn Asp Cys Lys Gly Gly Ile Met Glu Glu Trp His
225                 230                 235                 240

Gln Lys Leu His Asn Asn Thr Ser Pro Asp Asp Val Val Ile Cys Gln
                245                 250                 255

Ala Ile Ile Asp Tyr Ile Lys Ser Asp Phe Asp Ile Asn Val Tyr Trp
            260                 265                 270

Asp Thr Leu Asn Lys Asn Gly Ile Thr Lys Glu Arg Leu Leu Ser Tyr
        275                 280                 285

Asp Arg Ala Ile His Ser Glu Pro Lys Phe Arg Ser Asp Gln Lys Glu
    290                 295                 300

Gly Leu Leu Arg Asp Leu Gly Asn Tyr Met Arg Ser Leu Lys Ala Val
305                 310                 315                 320

His Ser Gly Ala Asp Leu Glu Ser Ala Ile Ala Thr Cys Met Gly Tyr
                325                 330                 335

Lys Ser Glu Gly Glu Gly Phe Met Val Gly Val Gln Ile Asn Pro Val
            340                 345                 350

Asn Gly Leu Ser Ser Gly Phe Pro Asp Leu Leu Gln Phe Val Leu Asp
        355                 360                 365

His Val Glu Asp Lys Ser Ala Glu Pro Leu Leu Glu Gly Leu Leu Glu
    370                 375                 380

Ala Arg Val Glu Leu Arg Pro Leu Leu Thr Gly Ser Ser Glu Arg Leu
385                 390                 395                 400

Lys Asp Leu Ile Phe Leu Asp Ile Ala Leu Asp Ser Thr Phe Arg Thr
```

```
                405                 410                 415
Ala Val Glu Arg Ser Tyr Glu Glu Leu Asn Asp Ala Ala Pro Glu Lys
            420                 425                 430

Ile Met Tyr Phe Ile Ser Leu Val Leu Glu Asn Leu Ala Leu Ser Thr
            435                 440                 445

Asp Asp Asn Glu Asp Ile Leu Tyr Cys Leu Lys Gly Trp Asn Arg Ala
    450                 455                 460

Met Asp Met Val Lys Gln Lys Asp Asp Gln Trp Ala Leu Tyr Ala Lys
465                 470                 475                 480

Ala Phe Leu Asp Arg Thr Arg Leu Ala Leu Ala Ser Lys Gly Glu Gln
                485                 490                 495

Tyr Tyr Asn Met Met Gln Pro Ser Ala Glu Tyr Leu Gly Ser Leu Leu
            500                 505                 510

Asn Val Glu Glu Trp Ala Val Asp Ile Phe Thr Glu Glu Val Ile Arg
            515                 520                 525

Gly Gly Ser Ala Ala Thr Leu Ser Ala Leu Leu Asn Arg Phe Asp Pro
    530                 535                 540

Val Leu Arg Asn Val Ala His Leu Gly Ser Trp Gln Val Ile Ser Pro
545                 550                 555                 560

Val Glu Val Thr Gly Tyr Ile Val Val Asp Lys Leu Leu Ser Val
                565                 570                 575

Gln Asn Lys Thr Tyr Asp Lys Pro Thr Ile Leu Val Ala Lys Ser Val
            580                 585                 590

Lys Gly Glu Glu Glu Ile Pro Asp Gly Val Val Gly Val Ile Thr Pro
            595                 600                 605

Asp Met Pro Asp Val Leu Ser His Val Ser Val Arg Ala Arg Asn Cys
    610                 615                 620

Lys Val Leu Phe Ala Thr Cys Phe Asp Pro Asn Thr Leu Ser Glu Phe
625                 630                 635                 640

Gln Gly His Glu Gly Lys Val Phe Ser Phe Lys Thr Thr Ser Ala Asp
                645                 650                 655

Val Thr Tyr Arg Glu Val Ser Asp Ser Glu Leu Met Gln Ser Ser Ser
            660                 665                 670

Ser Asp Ala Gln Gly Gly Glu Ala Ile Pro Ser Leu Ser Leu Val Lys
    675                 680                 685

Lys Lys Phe Leu Gly Lys Tyr Ala Ile Ser Ala Glu Glu Phe Ser Asp
            690                 695                 700

Glu Met Val Gly Ala Lys Ser Arg Asn Ile Ala Tyr Leu Lys Gly Lys
705                 710                 715                 720

Val Pro Ser Trp Val Gly Ile Pro Thr Ser Val Ala Ile Pro Phe Gly
                725                 730                 735

Thr Phe Glu Lys Ile Leu Ser Asp Glu Thr Asn Lys Glu Val Ala Gln
            740                 745                 750

Asn Ile Gln Met Leu Lys Gly Arg Leu Ala Gln Glu Asp Phe Ser Ala
            755                 760                 765

Leu Gly Glu Ile Arg Lys Thr Val Leu Asn Leu Thr Ala Pro Thr Gln
    770                 775                 780

Pro Val Lys Glu Leu Lys Glu Lys Met Leu Ser Ser Gly Met Pro Trp
785                 790                 795                 800

Pro Gly Asp Glu Ser Asp His Arg Trp Glu Gln Ala Trp Met Ala Ile
                805                 810                 815

Lys Lys Val Trp Ala Ser Lys Trp Asn Glu Arg Ala Tyr Phe Ser Thr
            820                 825                 830
```

Arg Lys Val Lys Leu Asp His Glu Tyr Leu Ser Met Ala Val Leu Val
            835                 840                 845

Gln Glu Ile Val Asn Ala Asp Tyr Ala Phe Val Ile His Thr Thr Asn
    850                 855                 860

Pro Ser Ser Gly Asp Ser Ser Glu Ile Tyr Ala Glu Val Val Lys Gly
865                 870                 875                 880

Leu Gly Glu Thr Leu Val Gly Ala Tyr Pro Gly Arg Ala Met Ser Phe
                885                 890                 895

Val Cys Lys Lys Asp Asp Leu Asp Ser Pro Lys Val Leu Gly Tyr Pro
                900                 905                 910

Ser Lys Pro Ile Gly Leu Phe Ile Lys Arg Ser Ile Ile Phe Arg Ser
            915                 920                 925

Asp Ser Asn Gly Glu Asp Leu Glu Gly Tyr Ala Gly Ala Gly Leu Tyr
        930                 935                 940

Asp Ser Val Pro Met Asp Val Glu Asp Glu Val Val Leu Asp Tyr Thr
945                 950                 955                 960

Thr Asp Pro Leu Ile Thr Asp Ser Gly Phe Arg Asn Ser Ile Leu Ser
                965                 970                 975

Ser Ile Ala Arg Ala Gly His Ala Ile Glu Glu Leu Tyr Gly Ser Pro
            980                 985                 990

Gln Asp Val Glu Gly Val Val Lys Asp Gly Lys Ile Tyr Val Val Gln
        995                 1000                1005

Thr

<210> SEQ ID NO 4
<211> LENGTH: 663
<212> TYPE: DNA
<213> ORGANISM: Hordeum vulgare

<400> SEQUENCE: 4
cggcacgagg gctaagaaga ttttagcgct ctaggagaaa tgcggaaaac tgtacttaat     60
ctaactgctc caactcaact ggtcaaggag ctgaaggaga agatgctaag ctctggaatg    120
ccctggcctg gggatgaaag tgaccaccgc tgggagcaag catggatggc aattaaaaag    180
gtttgggcat caaaatggaa tgaaagagca tattttagca cacgcaaggt gaagctcgat    240
catgattacc tttccatggc tgttcttgta caagaaattg tcaacgcaga ctatgccttt    300
gttattcata ctacaaaccc gtcatctgga gattcttccg agatatatgc tgaagtggta    360
aaaggacttg gagagacact tgtgggagct tatcctggcc gtgccatgag cttcgtgtgt    420
aagaaaaatg gccttgactc tcccaagact ctaatggtga ggatctggaa ggttatgctg    480
gagcagggct gtatgatagt gtccctatgg atgtggaaga cgaggttgta cttgactaca    540
ccactgaccc tctcatcact gactcgggat tccggaactc aatcctctca gcattgcac     600 gggctggcca cgccatcgag gagctctatg ggtcaccgca ggacgttgag ggagtagtga    660
agg                                                                  663

<210> SEQ ID NO 5
<211> LENGTH: 4302
<212> TYPE: DNA
<213> ORGANISM: Triticum aestivum

<400> SEQUENCE: 5
atggcgctaa ggaaggagag atatccatcc ggatcccgga agccgaatcc atccatccat     60
ccatcccata ctgcccttac gatcgagctg tttgatattc gtgcagatga gcggattctc    120

```
cgcggcagct gctgcggccg agcgcttgtc ggaaggttca ccctggatgc caactccgag    180
cttaaggtga cattgaaccc agcaccgcag ggttcggtgg tggagatcaa tctagaggca    240
actaacacca gcggctccct gatactgcat tggggcgccc ttcgcccgga tagaggagaa    300
tggctcctac catcccggaa accagatggc acgacagtgt acaagaacag ggctcttagg    360
acgcctttta taaagtcagg tgataactcc acgctgaaaa ttgagataga tgatcctgca    420
gtgcaagcca ttgagttcct catatttgat gaggcacgga ataattggtc agttcttttt    480
gggttaccca tcctaccctg tttcttggaa tgcagaagat atcaaataac aacactctac    540
tttggacagg aggagtatga agcagcacga actgagttga tagaggaatt aaacaagggt    600
gtttctttgg agaagctacg agcgaaactg acaaagacac ctgaggcaac tgatagtaat    660
gctcctgcat ctgaaagcac tgtgactact aaagtcccag aggaacttgt acaagtccag    720
gcttacataa ggtgggagaa agcaggcaag ccaaattatg ccccagagaa gcaattggtc    780
gagtttgagg aagcaaggaa ggaactgcag tctgagttgg ataaggggac ctcagttgag    840
cagttgagga acaaaatttt gaaagggaac attgagacaa agtttccaa gcagctgaag    900 gacaaaaaat actttctgt ggaaagaatt cagcggaaaa aacgagatat tgtgcaacta    960
cttaaaaaac acaagcctac tgttatggaa gcgcaagtag agactcctaa caacccact   1020 gttctggatc tcttcacaaa gtcattacag gagcaggata actgtgaggt tctaagcaga   1080
aagcttttca gttcggtga caaggagata ctggaaaaac caaagttcac ttggcaacaa   1140
actatatgga gccacttata cttcactggg cgttgtcaaa agagaatgga gagtggcaga   1200
caatgtgggc ctgtactgat ggggtgcttt gtaactgtga aggcacctcc ctcaagcata   1260
ttgccatctg gttcatcatt gctagacaag gcatgtgaaa cttcattcag tgaatatgaa   1320
ttgaatggtc tgcattgtca ggatactggt gatgctggta aaggcactgc taaggccttg   1380
cttgaaagaa tagcagatct agaggaagat gcccaacgat ctcttatgca cagattcaat   1440
attgcagcag atctagttga ccaagcaaga gataatggat tattgggtat tattggaatt   1500
tttgtttgga ttaggttcat ggctacaagg caactaatat ggaacaagaa ctacaatgtg   1560
aagccacgtg agataagcaa agcacaagat aggtttacag atgatcttga gaatatgtac   1620
agaacttacc cacaatatca ggagatctta agaatgataa tgtctgctgt tggtcgggga   1680
ggtgaaggtg atgttggtca acgcattcgt gatgagatat tagtaatcca gagaaataat   1740
gactgcaaag gtggaatgat ggaggagtgg caccagaaac tgcacaacaa tacaagccca   1800
gatgatgtag tgatctgcca ggccctactt gattatatca gagtgatttt tgatattggt   1860
gtttactggg acaccttgaa aaagatggt ataacaaaag agcgtctatt gagctatgat   1920
cgaccgattc attcagagcc aaatttcagg agtgaacaga agatggctt actccgtgac   1980 ttgggcaatt atatgagaag cctcaagatg gagggtaccc tgatacaatc actgcgaatg   2040
gcagtgcatt ctggtgctga tcttgaatct gctatagcaa cttgcatggg atacaaatca   2100
gagggtgaag gtttcatggt tggtgttcag attaatccag tgaagggttt gccatctgga   2160
tttcctaaat tgcttgaatt tgtacttgac catgttgagg ataaatcagc agaaccactt   2220
cttgaggggt tattggaggc tcgagctgaa ctacacccctt tgctccttgg ctctcctgaa   2280
cgcatgaagg atcttatctt tttagacatt gctcttgatt ctactttcag gacagcagtt   2340
gaaagatcat atgaggagct caataatgta gaaccagaga aaattatgta cttcatcagt   2400
cttgtccttg aaaatcttgc tttatccacc gacgacaatg aagatatcct atattgctta   2460
```

```
aagggatgga atcaagcctt ggaaatggct aaacagaaaa acaaccaatg ggctctctat      2520
gctaaagcat ttctggacag aaccagactt gcccttgcaa gcaagggaga acaatactat      2580
aatttgatgc agccctcagc tgaatatctt ggctcgttac ttaacattga ccaatgggca      2640
gttaatatct ttacagaaga aattattcgt ggtggatcag ctgctaccct gtctgctctt      2700
ctgaatcgga ttgatcctgt tcttaggaat gttgcacagc ttggaagttg gcaggttata      2760
agcccagttg aagtatcagg ttacattgta gtggttgatg aattgcttgc tgttcaaaac      2820
aaatcctatg ataaaccaac tatccttgtg gcaaagagtg tcaagggaga ggaagaaata      2880
ccagatggag ttgttggtgt tattacacct gatatgccag atgttctctc ccatgtatca      2940
gtccgagcaa ggaattgcaa ggttttattt gcaacatgct ttgatcctaa caccttgtct      3000
gaactccaag acatgatgg gaaagtgttt tccttcaaac ctacttctgc agatatcacc       3060
tatagggaga ttccagagag tgaactgcaa tcaggttctc taaatgcaga agctggccag      3120
gcagtgccat ctgtgtcatt agtcaagaag aagtttcttg gaaaatatgc aatatcagca      3180
gaagaattct ctgaggaaat gggtgtccct acatcagttg cgattccatt tgggacctttg    3240 gagaaggttt tgtctgatga aatcaataag gaagtcgcgc aaaccataca aatgctgaag      3300
ggaaaacttg ctcaagatga ttttagtgct ctaggcgaaa tacggaaaac tgttctcaat      3360
ttaactgctc ctactcaact gatcaaggaa ctgaaggaga agatgctagg ctctggaatg      3420
ccctggcctg gagatgaagg tgaccaacgt tgggagcaag catggatggc aattaaaaag      3480
gtttgggcgt caaaatggaa tgaaagagca tattttagca ctcgtaaggt gaagcttgat      3540
catgactacc tttccatggc tgtacttgta caagaaattg tcaatgcaga ctatgccttt      3600
gtcattcata ctactaaccc atcatcggga gattcgtctg agatatatgc tgaagtggtg      3660
aaagggcttg gagaaacact tgtaggagcc tatcctggtc gcgccatgag ctttgtatgt      3720
aagaaaaacg accttgactc tcccaaggta ctgggtttcc caagcaagcc aattggtctc      3780
ttcataaaga gatcaatcat ctttcgttca gattccaacg gtgaggattt agaagggtat      3840
gctggagcag gactgtatga tagttcgctc aagaatttat ttggcattac aactaagctg      3900
actgcttgtt tcagtgtccc tatggatgag gaagatgaag tcatactcga ctacaccacc      3960
gaccccctca ttacagatca gggattccaa aaatctatcc tctcgagcat tgcacgggct      4020
ggtcatgcca ttgaggagct ttatgggtcc ccacaggatg ttgagggtgc agtgaaggaa      4080
gggaagctat acgtagtaca gacaagacca cagatgggaa aagccaggga ggactactac      4140
caagtgctgg gagtgacggt taattcaacg cctcaggaga tcaaggaggc ttacaggaag      4200
ctccagaaac gacaccatat cctgatattg ctggctacaa gggtcatgca tgactacacc      4260
ctactgctga atgaggcata caaggtattg atgaggaatt aa                        4302
```

<210> SEQ ID NO 6
<211> LENGTH: 36
<212> TYPE: DNA
<213> ORGANISM: Triticum aestivum

<400> SEQUENCE: 6
aaaaggatcc ggtaccgcct tctggctcaa cagttc                               36

<210> SEQ ID NO 7
<211> LENGTH: 36
<212> TYPE: DNA
<213> ORGANISM: Triticum aestivum

<400> SEQUENCE: 7

```
aaaagaattc actagtatca ccttcacctc cacgac                                    36
```

<210> SEQ ID NO 8
<211> LENGTH: 413
<212> TYPE: DNA
<213> ORGANISM: Oryza spp.

<400> SEQUENCE: 8

```
tgctggagca gcagtatatg ataggttaga gaaagtccgc cataattttt gtagtttgct          60
caagaattta tttggcatta caactaagct gactgcttgt ttcagtgtcc ctatggatga         120
ggaagatgaa gtcgtactcg actacaccac agaccccctc attacagatc agggatccaa         180
aaatcaatcc tctcgagcat tgcacgggct ggtcatgcca ttgaggattt ctatgggtca         240
ccacagggca caggatgttg agggtgcagt gaaggaaggg aagctataag tagtacagac         300
aagaccacaa atgtaatcta tatgtatatt ttatagccaa gtcaatcagg aaatgttgta         360
gagtaagata tacgggccgt gggacatgta taacacgtta tgctcctttt ttt               413
```

<210> SEQ ID NO 9
<211> LENGTH: 462
<212> TYPE: DNA
<213> ORGANISM: Oryza spp.
<220> FEATURE:
<221> NAME/KEY: misc_feature
<222> LOCATION: (408)..(408)
<223> OTHER INFORMATION: n is a, c, g, or t

<400> SEQUENCE: 9

```
tctacaacta caacttttta gaatctggac caaaagctgg actgtttgag ggagcttctg          60
attctgagag aagctgcagc agctagaagc tcccccaaac aggcccttag gtagctggtt         120
acaagtctga tcacactgtt ttaggtttgt ctgttgttgt atatcagata gctaaatgca         180
tagctgtgag ctagagttgt gataaactgg aaataggtca gggaacgtct ttttttgcca         240
aagtatgggt aaagataaac ttggtgagct cagctgggga caaaatcatc agattttgta         300
ttctcccagc agagcaaata gggatttgcc tgtgagtgca tgcctgactt gtctgttggt         360
ctatgaaatg ggccgtgaag tgtgcttcta tgggccttgt cactactnac caggcggtat         420
tgcagagcag atttcttggc ccatttttgtc cttttctct ct                           462
```

<210> SEQ ID NO 10
<211> LENGTH: 490
<212> TYPE: DNA
<213> ORGANISM: Oryza spp.

<400> SEQUENCE: 10

```
cttgggaaga cggtgcgtgt tagatttgtg ctgaagaggg aatgcacgtt cggccagagc          60
ttccaccttg tcggcgacga cccggcgctc ggcctctggg atccgtcgaa ggcagtgcct         120
ttggattggt cagaaggaca cgactggact gtggagaaag tgagccttgc atcgtgcgca         180
ttgtttgatg tactctccctt ttgaggtaat catcacccct tttcttctgt acaggacttg        240
ccagccaaca agttgattga gtacaagttc gtgctgcaag atttgtcggg caagttgcat         300
tggcagaatg gtcgtaatag aagcgtacag acaggtgaaa ctgcaaacat tctagtcgta         360
tatgaagatt ggggtaatgc aaatagtcag acagtagaag aggagggtaa agtgtccatt         420
gggatggagg agggtaaatt gtccgttggg atggaggagg ctgtagttcc agatgatagt         480
gaaagcagag                                                               490
```

<210> SEQ ID NO 11
<211> LENGTH: 492
<212> TYPE: DNA
<213> ORGANISM: Sorghum bicolor
<220> FEATURE:
<221> NAME/KEY: misc_feature
<222> LOCATION: (484)..(484)
<223> OTHER INFORMATION: n is a, c, g, or t

<400> SEQUENCE: 11

| | | | | | |
|---|---|---|---|---|---|
| gcacgaggcc | cagttgaagt | atcaggttat | gtggttgtgg | ttgatgagtt | acttgctgtc | 60 |
| cagaacaaat | cttatgataa | accaaccatc | cttgtggcaa | agagtgtcaa | gggagaggaa | 120 |
| gaaataccag | atggagtagt | tggtgtaatt | acacctgata | tgccagatgt | tctgtcccat | 180 |
| gtgtcagtcc | gagcaaggaa | tagcaaggta | ctgttttgcaa | cctgttttga | ccataccact | 240 |
| ctgtctgaac | ttgaaggata | tgatcagaaa | ctgctttcct | tcaagcctac | ttctgcagat | 300 |
| ataacctata | gggagatcac | agagagtgag | cttcagcaat | caagttctcc | aaatgcagaa | 360 |
| gttggccatg | cagtaccatc | tatttcattg | gccaagaaga | aatttcttgg | aaaatatgca | 420 |
| atatcagctg | aagaattcac | cgaggaaatg | gttggggcca | agtctcggaa | atagcatacc | 480 |
| tcanaggaaa | ag | | | | | 492 |

<210> SEQ ID NO 12
<211> LENGTH: 704
<212> TYPE: DNA
<213> ORGANISM: Sorghum bicolor

<400> SEQUENCE: 12

| | | | | | |
|---|---|---|---|---|---|
| aagaactata | atgtgaagcc | acgtgagata | agcaaagcac | aggataggtt | tacagatgat | 60 |
| cttgagaata | tgtacagaac | ttatcctcag | tacagagaga | tactaagaat | gataatggct | 120 |
| gctgttggtc | gtggaggtga | aggtgacgtt | ggtcaacgca | ttcgtgatga | gatattagta | 180 |
| atacagagaa | ataatgactg | caaaggtgga | atgatgaaag | aatggcacca | gaaattgcac | 240 |
| aacaatacaa | gcccagatga | tgtagtgata | tgccaggcat | taattgatta | tataaaaaat | 300 |
| tttgatataa | gcgtttactg | ggacacctgg | aacaaaaatg | gcataaccaa | agagcgtctc | 360 |
| ttgagctatg | atcgtgctat | tcattcagaa | ccaaatttca | gaagtgaaca | gaaggagggt | 420 |
| ttactccgtg | acctgggaaa | ttacatgaga | agcctaaagg | ctgtgcattc | tggtgctgat | 480 |
| cttgaatctg | ctatagcaac | ttgtatggga | tacaaatcag | agggtgaagg | tttcatggtt | 540 |
| ggcgttcaga | tcaatccagt | gaagggtttg | ccatctggat | ttcctgagtt | gcttgaattt | 600 |
| gtgcttgacc | atgttgagga | taaatcagca | gaaccacttc | ttgagggggct | attggaagct | 660 |
| cgagttgatc | tgcgcccttt | gcttcttgat | tcgcctgaac | gcat | | 704 |

<210> SEQ ID NO 13
<211> LENGTH: 563
<212> TYPE: DNA
<213> ORGANISM: Sorghum bicolor

<400> SEQUENCE: 13

| | | | | | |
|---|---|---|---|---|---|
| gagaagccta | aaggctgtgc | attctggtgc | tgatcttgaa | tctgctatag | caacttgtat | 60 |
| gggatacaaa | tcagagggtg | aaggtttcat | ggttggcgtt | cagatcaatc | cagtgaaggg | 120 |
| tttgccatct | ggatttcctg | agttgcttga | atttgtgctt | gaccatgttg | aggataaatc | 180 |
| agcagaacca | cttcttgagg | ggctattgga | agctcgagtt | gatctgcgcc | ctttgcttct | 240 |
| tgattcacct | gaacgcatga | agatcttat | attttttggac | attgctcttg | attctacctt | 300 |

```
caggacagca attgaaaggt catatgagga gctcaatgat gcagcccag agaaaataat    360 gtacttcatc agtcttgtcc ttgaaaatct tgcgttttca attgacgaca atgaagacat    420
cctgtattgc ttaaagggat ggaaccaagc cttggaaatg gctaagcaaa agacgacca     480 atgggctctt tacgctaaag catttcttga cagaatcaga cttgcccttg cgagcaaggg    540
agaacagtac cataatatga tgc                                            563

<210> SEQ ID NO 14
<211> LENGTH: 705
<212> TYPE: DNA
<213> ORGANISM: Sorghum bicolor

<400> SEQUENCE: 14
gttcttgtgc aagaagttgt gaatgcagat tatgcttttg tcattcatac tacaaaccca     60
tcgtctggag attcttctga gatatatgct gaagtcgtga aagggctcgg agagactctc    120
gtgggagcct atcctggtcg tgctatgagc tttgtttgca aaaaagatga ccttgactct    180
cccaagttac ttggttaccc gagcaagcca attggtctct tcataaggcg atcgatcatc    240
tttcgttctg actccaacgg cgaggatctg gaaggttatg ccggagcagg attatatgat    300
agtgtaccga tggatgagga ggatgaagtc gtacttgatt acacaactga ccctcttata    360
gtagatcgtg gattccgaaa ttcaatactc tcaagcatcg cacgggctgg ccatgccatt    420
gaagagctat atggttctcc tcaggacgtc gagggtgtag tgaaggatgg aaaaatctat    480
gtagtccaga caagaccaca gatgtagcat gtatgtatta gctagctcaa taagcactgt    540
tgtacgcttg tatggttggg acatatgggt gttatggcat gtatagttta tgcctagatg    600
tacaacacgt gtaaactctt atatatgtat atatgctgaa acaagcattg gtcctgcaat    660
ttcattgtga ccagtctttg aaaatgaaca tgccgactta ttggc                   705

<210> SEQ ID NO 15
<211> LENGTH: 22
<212> TYPE: DNA
<213> ORGANISM: Oryza spp.

<400> SEQUENCE: 15
attgttaggt tgcaagttag tt                                              22

<210> SEQ ID NO 16
<211> LENGTH: 20
<212> TYPE: DNA
<213> ORGANISM: Oryza spp.

<400> SEQUENCE: 16
cttcccttcc ttcactgcac                                                 20

<210> SEQ ID NO 17
<211> LENGTH: 20
<212> TYPE: DNA
<213> ORGANISM: Oryza spp.

<400> SEQUENCE: 17
gcaaggctca ctttctccac                                                 20

<210> SEQ ID NO 18
<211> LENGTH: 20
<212> TYPE: DNA
<213> ORGANISM: Oryza spp.
```

-continued

```
<400> SEQUENCE: 18
tccatcccaa tggacacttt                                                  20

<210> SEQ ID NO 19
<211> LENGTH: 16
<212> TYPE: DNA
<213> ORGANISM: Oryza spp.

<400> SEQUENCE: 19
tacgacatgg aagccg                                                      16

<210> SEQ ID NO 20
<211> LENGTH: 15
<212> TYPE: DNA
<213> ORGANISM: Triticum spp.

<400> SEQUENCE: 20
gaaacacata gtctg                                                       15

<210> SEQ ID NO 21
<211> LENGTH: 16
<212> TYPE: DNA
<213> ORGANISM: Triticum spp.

<400> SEQUENCE: 21
ttgcggtgcc tttacc                                                      16

<210> SEQ ID NO 22
<211> LENGTH: 19
<212> TYPE: DNA
<213> ORGANISM: Triticum spp.

<400> SEQUENCE: 22
gaaagaaaca catagtctg                                                   19

<210> SEQ ID NO 23
<211> LENGTH: 20
<212> TYPE: DNA
<213> ORGANISM: Triticum spp.

<400> SEQUENCE: 23
atctgtaaac ctgtcttgtg                                                  20

<210> SEQ ID NO 24
<211> LENGTH: 16
<212> TYPE: DNA
<213> ORGANISM: Triticum spp.

<400> SEQUENCE: 24
ttgcggtgcc tttacc                                                      16

<210> SEQ ID NO 25
<211> LENGTH: 20
<212> TYPE: DNA
<213> ORGANISM: Triticum spp.

<400> SEQUENCE: 25
atctgtaaac ctgtcttgtg                                                  20
```